(12) United States Patent
Zucherman et al.

(10) Patent No.: US 8,048,117 B2
(45) Date of Patent: *Nov. 1, 2011

(54) INTERSPINOUS PROCESS IMPLANT AND METHOD OF IMPLANTATION

(75) Inventors: James F. Zucherman, San Francisco, CA (US); Ken Y. Hsu, San Francisco, CA (US); Henry A. Klyce, Piedmont, CA (US); Charles J. Winslow, Walnut Creek, CA (US); Scott A. Yerby, Montara, CA (US); John J. Flynn, Concord, CA (US); Steven T. Mitchell, Pleasant Hill, CA (US); John A. Markwart, Castro Valley, CA (US)

(73) Assignee: Kyphon Sarl, Neuchatel (CH)

( * ) Notice: Subject to any disclaimer, the term of this patent is extended or adjusted under 35 U.S.C. 154(b) by 320 days.

This patent is subject to a terminal disclaimer.

(21) Appl. No.: 11/234,555

(22) Filed: Sep. 23, 2005

(65) Prior Publication Data
US 2006/0089718 A1    Apr. 27, 2006

Related U.S. Application Data

(63) Continuation-in-part of application No. 10/850,267, filed on May 20, 2004, now Pat. No. 7,695,513.

(60) Provisional application No. 60/472,817, filed on May 22, 2003, provisional application No. 60/612,582, filed on Sep. 23, 2004.

(51) Int. Cl.
*A61B 17/70* (2006.01)

(52) U.S. Cl. ........................................ 606/248

(58) Field of Classification Search .... 623/17.11–17.16; 606/246–249
See application file for complete search history.

(56) References Cited

U.S. PATENT DOCUMENTS

| | | | |
|---|---|---|---|
| 278,097 A | 5/1883 | Collins |
| 624,969 A | 5/1899 | Peterson |
| 1,153,797 A | 9/1915 | Kegreisz |
| 1,516,347 A | 11/1924 | Pataky |
| 1,706,431 A | 3/1929 | Whitliff |
| 1,870,942 A | 8/1932 | Beatty |

(Continued)

FOREIGN PATENT DOCUMENTS

CA    2015507    1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, (c) 1997, Lippincott-Raven Publishers.

(Continued)

*Primary Examiner* — Anu Ramana

(57) ABSTRACT

Systems and method in accordance with embodiments of the present invention can includes an implant having a spacer with an expandable portion. An insert can be positioned within a groove of the spacer to distract the expandable portion away from the main portion of the spacer. The expandable portion can optionally include a grip that can at least partially deform to conform to a contour of a spinous process to provide a frictional grip to prevent the implant from shifting position. Implants in accordance with the present invention can also include a binder that can be arranged around the adjacent spinous processes to limit flexion movement.

16 Claims, 43 Drawing Sheets

U.S. PATENT DOCUMENTS

| | | | |
|---|---|---|---|
| 2,077,804 A | 4/1937 | Morrison | |
| 2,299,308 A | 10/1942 | Creighton | |
| 2,456,806 A | 12/1948 | Wolffe | 33/174 |
| 2,485,531 A | 10/1949 | Dzus et al. | |
| 2,502,902 A | 4/1950 | Tofflemire | |
| 2,607,370 A | 8/1952 | Anderson | |
| 2,677,369 A | 5/1954 | Knowles | 128/92 |
| 2,685,877 A | 8/1954 | Dobelle | |
| 3,065,659 A | 11/1962 | Eriksson et al. | |
| 3,108,595 A | 10/1963 | Overment | |
| 3,123,077 A | 3/1964 | Alcamo | |
| 3,397,699 A | 8/1968 | Kohl | |
| 3,426,364 A | 2/1969 | Lumb | 3/1 |
| 3,643,658 A | 2/1972 | Steinemenan | 128/920 |
| 3,648,691 A | 3/1972 | Lumb | 128/920 |
| 3,654,668 A | 4/1972 | Appleton | |
| 3,678,542 A | 7/1972 | Prete, Jr. | |
| 3,779,239 A | 12/1973 | Fischer et al. | |
| 3,867,728 A | 2/1975 | Stubstad | 3/1 |
| 3,875,595 A | 4/1975 | Froning | 3/1 |
| 4,003,376 A | 1/1977 | McKay et al. | |
| 4,011,602 A | 3/1977 | Rybicki et al. | |
| 4,034,418 A | 7/1977 | Jackson | 3/1.911 |
| 4,047,523 A | 9/1977 | Hall | |
| 4,219,015 A | 8/1980 | Steinemann | 128/92 D |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,309,777 A | 1/1982 | Patil | 3/1.91 |
| 4,327,736 A | 5/1982 | Inoue | |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |
| 4,448,191 A | 5/1984 | Rodnyansky et al. | |
| 4,455,690 A | 6/1984 | Homsy | 3/1 |
| 4,479,491 A | 10/1984 | Martin | 128/92 B |
| 4,499,636 A * | 2/1985 | Tanaka | |
| 4,501,269 A | 2/1985 | Bagby | 128/96 G |
| 4,502,161 A | 3/1985 | Wall | 623/18 |
| 4,519,100 A | 5/1985 | Wills et al. | |
| 4,553,273 A | 11/1985 | Wu | 623/18 |
| 4,554,914 A | 11/1985 | Kapp | 128/92 C |
| 4,570,618 A | 2/1986 | Wu | |
| 4,573,454 A | 3/1986 | Hoffman | |
| 4,592,341 A | 6/1986 | Omagari et al. | |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,632,101 A | 12/1986 | Freedland | |
| 4,636,217 A | 1/1987 | Ogilvie | 623/17 |
| 4,643,174 A | 2/1987 | Horiuchi | |
| 4,643,178 A | 2/1987 | Nastari | 128/92 |
| 4,646,998 A | 3/1987 | Pate | |
| 4,657,550 A | 4/1987 | Daher | 623/17 |
| 4,662,808 A | 5/1987 | Camilleri | |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,704,057 A | 11/1987 | McSherry | |
| 4,714,469 A | 12/1987 | Kenna | 623/17 |
| 4,721,103 A | 1/1988 | Freedland | |
| 4,743,256 A | 5/1988 | Brantigan | 623/17 |
| 4,759,769 A | 7/1988 | Hedman et al. | |
| 4,772,287 A | 9/1988 | Ray | 623/17 |
| 4,776,851 A | 10/1988 | Bruchman et al. | |
| 4,779,816 A | 10/1988 | Varlet | |
| 4,787,378 A | 11/1988 | Sodhi | |
| 4,790,303 A | 12/1988 | Steffee | 128/924 M |
| 4,822,226 A | 4/1989 | Kennedy | |
| 4,827,918 A | 5/1989 | Olerud | |
| 4,834,600 A | 5/1989 | Lemke | |
| 4,834,757 A | 5/1989 | Brantigan | 623/17 |
| 4,841,959 A | 6/1989 | Ransford | |
| 4,863,476 A | 9/1989 | Shepperd | |
| 4,878,915 A | 11/1989 | Brantigan | 623/17 |
| 4,886,405 A | 12/1989 | Blomberg | |
| 4,892,545 A | 1/1990 | Day et al. | |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,913,144 A | 4/1990 | Del Medico | |
| 4,923,471 A | 5/1990 | Morgan | 623/16 |
| 4,931,055 A | 6/1990 | Bumpus et al. | |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,887 A | 11/1990 | Sodhi | |
| 4,969,888 A | 11/1990 | Scholten | 606/94 |
| 4,998,936 A | 3/1991 | Mehdian | |
| 5,000,166 A * | 3/1991 | Karpf | |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,030,220 A | 7/1991 | Howland | |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,098,433 A | 3/1992 | Freedland | |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,171,278 A | 12/1992 | Pisharodi | |
| 5,180,381 A | 1/1993 | Aust | 606/61 |
| 5,180,393 A | 1/1993 | Commarmond | |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,267,999 A | 12/1993 | Olerud | |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,306,310 A | 4/1994 | Siebels | |
| 5,312,405 A | 5/1994 | Korotko et al. | |
| 5,316,422 A | 5/1994 | Coffman | |
| 5,352,225 A | 10/1994 | Yuan | 606/61 |
| 5,356,412 A | 10/1994 | Golds et al. | |
| 5,356,417 A | 10/1994 | Golds | |
| 5,356,423 A | 10/1994 | Tihon et al. | |
| 5,360,430 A | 11/1994 | Lin | |
| 5,366,455 A | 11/1994 | Dove | 606/61 |
| 5,370,697 A * | 12/1994 | Baumgartner | |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,370 A | 3/1995 | Muller et al. | |
| 5,395,372 A | 3/1995 | Holt | 606/61 |
| 5,401,269 A | 3/1995 | Buttner-Janz et al. | |
| 5,403,316 A | 4/1995 | Ashman | |
| 5,415,661 A | 5/1995 | Holmes | 606/69 |
| 5,437,672 A | 8/1995 | Alleyne | 606/61 |
| 5,437,674 A | 8/1995 | Worcel et al. | |
| 5,439,463 A | 8/1995 | Lin | |
| 5,443,514 A | 8/1995 | Steffee | 623/17 |
| 5,454,812 A | 10/1995 | Lin | 606/61 |
| 5,456,689 A | 10/1995 | Kresch et al. | |
| 5,456,722 A | 10/1995 | McLeod | 623/13 |
| 5,458,638 A | 10/1995 | Kuslich | 623/17 |

| Patent No. | Date | Name | Class |
|---|---|---|---|
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,480,442 A | 1/1996 | Bertagnoli | |
| 5,491,882 A | 2/1996 | Walston | 29/419.1 |
| 5,496,318 A | 3/1996 | Howland | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,518,498 A | 5/1996 | Lindenberg et al. | |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,662 A | 10/1996 | Brumfield et al. | |
| 5,562,735 A | 10/1996 | Margulies | |
| 5,562,736 A | 10/1996 | Ray | 623/17 |
| 5,571,191 A | 11/1996 | Fitz | 623/17 |
| 5,571,192 A | 11/1996 | Schonhoffer | |
| 5,575,819 A | 11/1996 | Amis | |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,609,635 A | 3/1997 | Michelson | |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,630,816 A | 5/1997 | Kambin | |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,653,762 A | 8/1997 | Pisharodi | |
| 5,653,763 A | 8/1997 | Errico et al. | |
| 5,658,286 A | 8/1997 | Sava | 606/61 |
| 5,658,335 A | 8/1997 | Allen | |
| 5,665,096 A | 9/1997 | Yoon | |
| 5,665,122 A | 9/1997 | Kambin | |
| 5,672,177 A | 9/1997 | Seldin | 606/71 |
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,685,826 A | 11/1997 | Bonutti | |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,455 A | 12/1997 | Saggar | 623/17 |
| 5,707,390 A | 1/1998 | Bonutti | |
| 5,716,416 A | 2/1998 | Lin | |
| 5,723,013 A | 3/1998 | Jeanson et al. | |
| 5,725,341 A | 3/1998 | Hofmeister | |
| 5,725,582 A | 3/1998 | Bevan | 623/17 |
| 5,741,261 A | 4/1998 | Moskovitz | 606/79 |
| 5,746,762 A | 5/1998 | Bass | |
| 5,755,797 A | 5/1998 | Baumgartner | |
| 5,766,251 A | 6/1998 | Koshino | 623/16 |
| 5,766,252 A | 6/1998 | Henry | 623/17 |
| 5,790,697 A * | 8/1998 | McDowell | |
| 5,800,438 A | 9/1998 | Tuke | 606/90 |
| 5,800,547 A | 9/1998 | Schafer et al. | |
| 5,810,815 A | 9/1998 | Morales | |
| 5,824,098 A | 10/1998 | Stein | 623/20 |
| 5,836,948 A | 11/1998 | Zucherman | 606/61 |
| 5,849,004 A | 12/1998 | Bramlet | |
| 5,860,977 A | 1/1999 | Zucherman | 606/61 |
| 5,865,846 A | 2/1999 | Bryan | 623/17 |
| 5,876,402 A | 3/1999 | Errico | 606/61 |
| 5,876,404 A | 3/1999 | Zucherman | 606/61 |
| 5,879,396 A | 3/1999 | Walston | 623/21 |
| 5,885,290 A * | 3/1999 | Guerrero et al. | |
| 5,885,299 A | 3/1999 | Winslow | 606/99 |
| 5,888,196 A | 3/1999 | Bonutti | |
| 5,888,224 A | 3/1999 | Beckers | 627/17 |
| 5,888,226 A | 3/1999 | Rogozinski | 623/17 |
| 5,941,881 A * | 8/1999 | Barnes | |
| 5,951,555 A | 9/1999 | Rehak | 606/61 |
| 5,976,186 A | 11/1999 | Bao | 623/17 |
| 5,980,523 A | 11/1999 | Jackson | |
| 6,001,130 A | 12/1999 | Bryan | 623/17 |
| 6,022,376 A | 2/2000 | Assell | 623/17 |
| 6,030,162 A | 2/2000 | Huebner | 411/413 |
| 6,045,552 A | 4/2000 | Zucherman | 606/61 |
| 6,045,554 A | 4/2000 | Grooms | 606/73 |
| 6,048,204 A | 4/2000 | Klardie | 433/174 |
| 6,048,342 A | 4/2000 | Zucherman | 606/61 |
| 6,048,344 A | 4/2000 | Schenk | 606/73 |
| 6,068,630 A | 5/2000 | Zucherman | 606/61 |
| RE36,758 E | 6/2000 | Fitz | 623/17 |
| 6,074,390 A | 6/2000 | Zucherman | 606/61 |
| 6,090,043 A | 7/2000 | Austin et al. | |
| 6,090,112 A | 7/2000 | Zucherman | 606/61 |
| 6,099,531 A | 8/2000 | Bonutti | 606/87 |
| 6,113,639 A | 9/2000 | Ray | 623/17.16 |
| 6,126,689 A | 10/2000 | Brett | |
| 6,126,691 A | 10/2000 | Kasra et al. | |
| 6,127,597 A | 10/2000 | Beyar et al. | |
| 6,129,730 A | 10/2000 | Bono | 606/73 |
| 6,132,464 A | 10/2000 | Martin | 623/17 |
| 6,139,550 A | 10/2000 | Michelson | 606/69 |
| 6,149,652 A | 11/2000 | Zucherman | 606/61 |
| 6,152,926 A | 11/2000 | Zucherman | 606/61 |
| 6,152,927 A | 11/2000 | Farris | 606/69 |
| 6,156,038 A | 12/2000 | Zucherman | 606/61 |
| 6,156,067 A | 12/2000 | Bryan | 623/17.15 |
| 6,183,471 B1 | 2/2001 | Zucherman | 606/61 |
| 6,190,387 B1 | 2/2001 | Zucherman | 606/61 |
| 6,190,413 B1 | 2/2001 | Sutcliffe | |
| 6,190,414 B1 | 2/2001 | Young | 623/17.15 |
| 6,193,721 B1 | 2/2001 | Michelson | 606/70 |
| 6,200,322 B1 | 3/2001 | Branch | 606/96 |
| 6,206,922 B1 | 3/2001 | Zdeblick | 623/17.11 |
| 6,214,037 B1 | 4/2001 | Mitchell et al. | |
| 6,214,050 B1 | 4/2001 | Huene | |
| 6,217,580 B1 | 4/2001 | Levin | 606/71 |
| 6,224,599 B1 | 5/2001 | Baynham et al. | |
| 6,224,602 B1 | 5/2001 | Hayes | 606/69 |
| 6,224,607 B1 | 5/2001 | Michelson | 606/96 |
| 6,228,900 B1 | 5/2001 | Shen | 522/153 |
| 6,234,705 B1 | 5/2001 | Troxell | 403/237 |
| 6,235,030 B1 | 5/2001 | Zucherman | 606/61 |
| 6,238,397 B1 | 5/2001 | Zucherman | 606/61 |
| 6,245,107 B1 | 6/2001 | Ferree | |
| 6,261,296 B1 | 7/2001 | Aebi | 606/90 |
| 6,280,444 B1 | 8/2001 | Zucherman | 606/61 |
| 6,293,949 B1 | 9/2001 | Justis | 606/61 |
| 6,299,642 B1 | 10/2001 | Chan | |
| 6,306,136 B1 | 10/2001 | Baccelli | 606/61 |
| 6,312,431 B1 | 11/2001 | Asfora | |
| 6,332,882 B1 | 12/2001 | Zucherman | 606/61 |
| 6,332,883 B1 | 12/2001 | Zucherman | 606/61 |
| 6,336,930 B1 | 1/2002 | Stalcup et al. | |
| 6,348,053 B1 | 2/2002 | Cachia | |
| 6,352,537 B1 | 3/2002 | Strnad | 606/61 |
| 6,364,883 B1 | 4/2002 | Santilli | |
| 6,368,351 B1 | 4/2002 | Glenn | 623/17.15 |
| 6,371,984 B1 | 4/2002 | Van Dyke | 623/11.11 |
| 6,371,987 B1 | 4/2002 | Weiland et al. | |
| 6,375,682 B1 | 4/2002 | Fleischmann et al. | |
| 6,379,355 B1 | 4/2002 | Zucherman | 606/61 |
| 6,383,186 B1 | 5/2002 | Michelson | 606/69 |
| 6,383,191 B1 | 5/2002 | Zdeblick et al. | |
| 6,395,030 B1 | 5/2002 | Songer | 623/17.11 |
| 6,398,783 B1 | 6/2002 | Michelson | 606/70 |
| 6,402,750 B1 | 6/2002 | Atkinson et al. | |
| 6,402,751 B1 | 6/2002 | Hoeck et al. | |
| 6,402,756 B1 | 6/2002 | Ralph | 606/71 |
| 6,416,776 B1 | 7/2002 | Shamie | 424/423 |
| 6,419,676 B1 | 7/2002 | Zucherman | 606/61 |
| 6,419,677 B2 | 7/2002 | Zucherman | 606/61 |
| 6,419,703 B1 | 7/2002 | Fallin | 623/17.11 |

| | | | | | | |
|---|---|---|---|---|---|---|
| 6,419,704 B1 | 7/2002 | Ferree | | 7,063,701 B2 | 6/2006 | Michelson ............... 606/73 |
| 6,428,542 B1 | 8/2002 | Michelson ............... 606/70 | | 7,063,702 B2 | 6/2006 | Michelson ............... 606/73 |
| 6,432,130 B1 * | 8/2002 | Hanson | | 7,070,598 B2 | 7/2006 | Lim et al. |
| 6,436,145 B1 | 8/2002 | Miller ............... 623/20.34 | | 7,074,237 B2 | 7/2006 | Goble et al. ............... 623/17.11 |
| 6,440,169 B1 | 8/2002 | Elberg et al. ............... 623/17.16 | | 7,077,844 B2 | 7/2006 | Michelson ............... 606/71 |
| 6,447,513 B1 | 9/2002 | Griggs | | 7,081,120 B2 | 7/2006 | Li et al. |
| 6,451,019 B1 | 9/2002 | Zucherman ............... 606/61 | | 7,087,055 B2 | 8/2006 | Lim et al. |
| 6,451,020 B1 | 9/2002 | Zucherman ............... 606/61 | | 7,087,083 B2 | 8/2006 | Pasquet et al. |
| 6,454,771 B1 | 9/2002 | Michelson ............... 606/70 | | 7,087,084 B2 | 8/2006 | Reiley ............... 623/17.11 |
| 6,458,131 B1 | 10/2002 | Ray ............... 606/61 | | 7,090,698 B2 | 8/2006 | Goble et al. ............... 623/17.11 |
| 6,478,796 B2 | 11/2002 | Zucherman ............... 606/61 | | 7,097,645 B2 | 8/2006 | Michelson ............... 606/71 |
| 6,500,178 B2 | 12/2002 | Zucherman ............... 606/61 | | 7,097,648 B1 | 8/2006 | Globerman et al. |
| 6,511,508 B1 * | 1/2003 | Shahinpoor et al. | | 7,097,654 B1 | 8/2006 | Freedland |
| 6,514,256 B2 | 2/2003 | Zucherman ............... 606/61 | | 7,101,375 B2 | 9/2006 | Zucherman et al. ............... 606/61 |
| 6,520,991 B2 | 2/2003 | Huene | | 7,101,398 B2 | 9/2006 | Dooris et al. ............... 623/13.11 |
| 6,527,776 B1 | 3/2003 | Michelson ............... 606/70 | | 7,112,202 B2 | 9/2006 | Michelson ............... 606/71 |
| 6,554,833 B2 | 4/2003 | Levy | | 7,115,130 B2 | 10/2006 | Michelson ............... 606/71 |
| 6,558,423 B1 | 5/2003 | Michelson ............... 623/17.11 | | 7,128,760 B2 * | 10/2006 | Michelson ............... 623/17.15 |
| 6,558,686 B1 | 5/2003 | Darouiche ............... 424/423 | | 7,163,558 B2 | 1/2007 | Senegas et al. |
| 6,565,570 B2 | 5/2003 | Sterett ............... 606/69 | | 7,163,561 B2 | 1/2007 | Michelson ............... 623/17.16 |
| 6,565,605 B2 | 5/2003 | Goble ............... 623/17.11 | | 7,201,751 B2 * | 4/2007 | Zucherman et al. ............... 606/249 |
| 6,579,318 B2 | 6/2003 | Varga ............... 623/17.11 | | 7,217,293 B2 | 5/2007 | Branch, Jr. |
| 6,579,319 B2 | 6/2003 | Goble ............... 623/17.11 | | 7,238,204 B2 | 7/2007 | Le Couedic et al. |
| 6,582,433 B2 | 6/2003 | Yun ............... 606/61 | | 7,306,628 B2 * | 12/2007 | Zucherman et al. ............... 623/17.11 |
| 6,582,467 B1 | 6/2003 | Teitelbaum et al. | | 7,335,203 B2 | 2/2008 | Winslow et al. |
| 6,592,585 B2 | 7/2003 | Lee et al. | | 7,377,942 B2 | 5/2008 | Berry |
| 6,592,586 B1 | 7/2003 | Michelson ............... 606/71 | | 7,431,735 B2 | 10/2008 | Liu et al. |
| 6,610,091 B1 | 8/2003 | Reiley ............... 623/17.11 | | 7,442,208 B2 | 10/2008 | Mathieu et al. |
| 6,620,163 B1 | 9/2003 | Michelson ............... 606/61 | | 7,445,637 B2 | 11/2008 | Taylor |
| 6,626,944 B1 | 9/2003 | Taylor ............... 623/17.16 | | 7,458,981 B2 | 12/2008 | Fielding et al. |
| 6,641,585 B2 | 11/2003 | Sato et al. ............... 606/61 | | 7,476,251 B2 * | 1/2009 | Zucherman et al. ............... 623/17.15 |
| 6,645,207 B2 | 11/2003 | Dixon et al. | | 7,524,324 B2 | 4/2009 | Winslow et al. |
| 6,652,527 B2 | 11/2003 | Zucherman ............... 606/61 | | 7,582,106 B2 | 9/2009 | Teitelbaum et al. |
| 6,652,534 B2 | 11/2003 | Zucherman ............... 606/102 | | 7,604,652 B2 | 10/2009 | Arnin et al. |
| 6,669,729 B2 | 12/2003 | Chin ............... 623/17.11 | | 7,611,316 B2 | 11/2009 | Panasik et al. |
| 6,685,742 B1 | 2/2004 | Jackson | | 7,621,950 B1 * | 11/2009 | Globerman et al. |
| 6,695,842 B2 | 2/2004 | Zucherman ............... 606/61 | | 7,658,752 B2 | 2/2010 | Labrom et al. |
| 6,699,246 B2 | 3/2004 | Zucherman ............... 606/61 | | 7,749,252 B2 | 7/2010 | Zucherman et al. |
| 6,699,247 B2 | 3/2004 | Zucherman ............... 606/61 | | 7,771,456 B2 | 8/2010 | Hartmann et al. |
| 6,709,435 B2 | 3/2004 | Lin | | 7,776,091 B2 | 8/2010 | Mastrorio et al. |
| 6,712,819 B2 | 3/2004 | Zucherman ............... 606/61 | | 7,901,430 B2 | 3/2011 | Matsuura et al. |
| 6,712,852 B1 | 3/2004 | Chung ............... 623/17.11 | | 2001/0016743 A1 | 8/2001 | Zucherman et al. |
| 6,723,126 B1 | 4/2004 | Berry | | 2001/0018614 A1 | 8/2001 | Bianchi |
| 6,730,126 B2 | 5/2004 | Boehm, Jr. et al. | | 2002/0068977 A1 * | 6/2002 | Jackson ............... 623/17.15 |
| 6,730,127 B2 | 5/2004 | Michelson ............... 623/17.16 | | 2002/0133155 A1 | 9/2002 | Ferree |
| 6,733,534 B2 | 5/2004 | Sherman | | 2002/0143331 A1 | 10/2002 | Zucherman et al. |
| 6,736,818 B2 | 5/2004 | Perren et al. | | 2002/0151895 A1 | 10/2002 | Soboleski |
| 6,743,257 B2 | 6/2004 | Castro | | 2002/0183756 A1 | 12/2002 | Michelson |
| 6,746,485 B1 | 6/2004 | Zucherman ............... 623/17.16 | | 2003/0040746 A1 | 2/2003 | Mitchell |
| 6,752,831 B2 | 6/2004 | Sybert ............... 623/13.17 | | 2003/0045940 A1 | 3/2003 | Eberlein et al. |
| 6,758,863 B2 | 7/2004 | Estes et al. | | 2003/0065330 A1 | 4/2003 | Zucherman et al. |
| 6,761,720 B1 | 7/2004 | Senegas ............... 606/61 | | 2003/0153915 A1 | 8/2003 | Nekozuka et al. |
| 6,764,491 B2 | 7/2004 | Frey et al. ............... 606/85 | | 2004/0006391 A1 | 1/2004 | Reiley |
| 6,770,096 B2 | 8/2004 | Bolger et al. | | 2004/0010312 A1 | 1/2004 | Enayati |
| 6,783,527 B2 | 8/2004 | Drewry ............... 606/61 | | 2004/0010316 A1 * | 1/2004 | William et al. |
| 6,783,530 B1 | 8/2004 | Levy | | 2004/0049273 A1 | 3/2004 | Reiley |
| 6,796,983 B1 | 9/2004 | Zucherman ............... 606/61 | | 2004/0049274 A1 | 3/2004 | Reiley |
| 6,800,670 B2 | 10/2004 | Shen ............... 522/153 | | 2004/0049275 A1 | 3/2004 | Reiley |
| 6,811,567 B2 | 11/2004 | Reiley ............... 623/17.11 | | 2004/0049276 A1 | 3/2004 | Reiley |
| 6,835,205 B2 | 12/2004 | Atkinson et al. | | 2004/0049277 A1 | 3/2004 | Reiley |
| 6,902,566 B2 | 6/2005 | Zucherman ............... 606/61 | | 2004/0049278 A1 | 3/2004 | Reiley |
| 6,902,580 B2 | 6/2005 | Fallin et al. | | 2004/0049281 A1 | 3/2004 | Reiley |
| 6,905,512 B2 | 6/2005 | Paes et al. | | 2004/0087947 A1 | 5/2004 | Lim et al. |
| 6,926,728 B2 | 8/2005 | Zucherman et al. ............... 606/190 | | 2004/0087948 A1 | 5/2004 | Suddaby |
| 6,936,050 B2 | 8/2005 | Michelson ............... 606/61 | | 2004/0097931 A1 | 5/2004 | Mitchell |
| 6,936,051 B2 | 8/2005 | Michelson ............... 606/61 | | 2004/0106995 A1 | 6/2004 | Le Couedic et al. |
| 6,946,000 B2 | 9/2005 | Senegas et al. | | 2004/0116927 A1 | 6/2004 | Graf |
| 6,949,123 B2 | 9/2005 | Reiley ............... 623/17.11 | | 2004/0117017 A1 | 6/2004 | Pasquet et al. |
| 6,969,390 B2 | 11/2005 | Michelson ............... 606/61 | | 2004/0122427 A1 | 6/2004 | Holmes |
| 6,972,019 B2 | 12/2005 | Michelson ............... 606/61 | | 2004/0133204 A1 | 7/2004 | Davies |
| 6,974,478 B2 | 12/2005 | Reiley et al. ............... 623/17.11 | | 2004/0133280 A1 | 7/2004 | Trieu |
| 6,981,975 B2 | 1/2006 | Michelson | | 2004/0143268 A1 | 7/2004 | Falahee |
| 7,011,685 B2 | 3/2006 | Arnin et al. | | 2004/0167625 A1 | 8/2004 | Beyar et al. |
| 7,025,789 B2 | 4/2006 | Chow et al. ............... 623/21.11 | | 2004/0181229 A1 | 9/2004 | Michelson |
| 7,041,105 B2 | 5/2006 | Michelson ............... 606/71 | | 2004/0186475 A1 | 9/2004 | Falahee |
| 7,041,135 B2 | 5/2006 | Michelson ............... 623/17.11 | | 2004/0199255 A1 | 10/2004 | Mathieu et al. |
| 7,041,136 B2 | 5/2006 | Goble et al. ............... 623/17.11 | | 2004/0210313 A1 | 10/2004 | Michelson |
| 7,044,952 B2 | 5/2006 | Michelson ............... 606/71 | | 2004/0230201 A1 | 11/2004 | Yuan |
| 7,048,736 B2 | 5/2006 | Robinson et al. ............... 606/61 | | 2004/0230304 A1 | 11/2004 | Yuan |

| | | |
|---|---|---|
| 2004/0236334 A1 | 11/2004 | Michelson |
| 2004/0236335 A1 | 11/2004 | Michelson |
| 2004/0260397 A1 | 12/2004 | Lambrecht et al. |
| 2005/0010293 A1 | 1/2005 | Zucherman et al. |
| 2005/0027297 A1 | 2/2005 | Michelson |
| 2005/0027298 A1 | 2/2005 | Michelson |
| 2005/0033434 A1 | 2/2005 | Berry |
| 2005/0049708 A1 | 3/2005 | Atkinson et al. |
| 2005/0085814 A1 | 4/2005 | Sherman et al. |
| 2005/0143827 A1* | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0209603 A1 | 9/2005 | Zucherman et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Feree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0149242 A1 | 7/2006 | Kraus et al. |
| 2006/0149278 A1 | 7/2006 | Abdou |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235386 A1 | 10/2006 | Anderson |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241610 A1 | 10/2006 | Lim et al. |
| 2006/0241613 A1 | 10/2006 | Bruneau et al. |
| 2006/0241614 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1* | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1* | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0009866 A1 | 1/2008 | Alamin et al. |
| 2008/0015693 A1 | 1/2008 | Le Couedic |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1* | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1* | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0018658 A1* | 1/2009 | Garcia |
| 2009/0062915 A1 | 3/2009 | Kohm et al. |
| 2009/0105766 A1* | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| DE | 2821678 A1 | 11/1979 |
| DE | 2821678 A1 | 4/1980 |
| DE | 3113142 A1 | 1/1982 |
| DE | 3922044 A1 | 2/1991 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0322334 B1 | 2/1992 |

| | | | |
|---|---|---|---|
| EP | 0307241 B1 | 12/1992 |
| EP | 0677277 A2 | 10/1995 |
| EP | 0767636 B1 | 4/1997 |
| EP | 0767636 B1 | 1/1999 |
| EP | 1004276 A1 | 5/2000 |
| EP | 1011464 B1 * | 6/2000 |
| EP | 1138268 A1 | 10/2001 |
| EP | 1148850 B1 * | 10/2001 |
| EP | 1148851 B1 * | 10/2001 |
| EP | 1302169 A1 | 4/2003 |
| EP | 1330987 A1 | 7/2003 |
| EP | 1552797 A2 * | 7/2005 |
| EP | 1854433 A1 | 11/2007 |
| EP | 1905392 * | 4/2008 |
| EP | 1982664 A1 | 10/2008 |
| FR | 2623085 | 5/1989 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2717675 A1 | 9/1995 |
| FR | 2722087 A1 | 1/1996 |
| FR | 2722088 | 1/1996 |
| FR | 2722088 A1 | 1/1996 |
| FR | 2722980 A1 | 2/1996 |
| FR | 2724554 | 3/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2780269 A1 | 12/1999 |
| FR | 2782911 A1 | 3/2000 |
| FR | 2799948 A1 | 4/2001 |
| FR | 2806614 A1 | 9/2001 |
| FR | 2806616 A1 | 9/2001 |
| FR | 2816197 A1 | 5/2002 |
| GB | 780652 | 8/1957 |
| JP | 02-224660 | 9/1990 |
| JP | 09-075381 | 3/1997 |
| JP | 10-179622 | 7/1998 |
| SU | 988281 | 1/1983 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 94/26195 | 11/1994 |
| WO | WO 95/35067 | 12/1995 |
| WO | WO 96/08206 A1 | 3/1996 |
| WO | WO 96/39975 | 12/1996 |
| WO | 97/18769 | 5/1997 |
| WO | WO 98/20939 | 5/1998 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/44319 | 8/2000 |
| WO | WO 00/53126 | 9/2000 |
| WO | WO 01/26566 A1 | 4/2001 |
| WO | WO 01/28442 A1 | 4/2001 |
| WO | WO 01/54598 A1 | 8/2001 |
| WO | WO 02/34120 A2 | 5/2002 |
| WO | WO 02/051326 | 7/2002 |
| WO | WO 02/085226 A1 | 10/2002 |
| WO | WO 03/057055 A1 | 7/2003 |
| WO | WO 03/101350 A1 | 12/2003 |
| WO | WO 2004/047689 A1 | 6/2004 |
| WO | WO 2004/047691 A1 | 6/2004 |
| WO | WO 2004/071358 A1 | 8/2004 |
| WO | 2004/084768 A2 | 10/2004 |
| WO | WO 2004/098465 A1 | 11/2004 |
| WO | 2004/110300 A2 * | 12/2004 |
| WO | WO 2005/009300 A1 | 2/2005 |
| WO | WO 2005/011507 A1 | 2/2005 |
| WO | 2005/037150 A1 | 4/2005 |
| WO | WO 2005/044118 A1 | 5/2005 |
| WO | WO 2005/048856 A1 | 6/2005 |
| WO | WO 2005/110258 A1 | 11/2005 |
| WO | 2006/064356 A1 | 6/2006 |
| WO | WO 2007/034516 A1 | 3/2007 |
| WO | 2007/052975 A1 | 5/2007 |
| WO | 2009/083276 A1 | 7/2009 |
| WO | 2009/083583 A1 | 7/2009 |
| WO | 2009/098536 A1 | 8/2009 |

OTHER PUBLICATIONS

Waldemar Link, brochure entitled *Wirbelsäulen-Chirurgie: Instrumentarium Und Implantate Zur Wirbelsäulen-Chirurgie* (Spinal Surgery: Instrumentation and Implants for Spinal Surgery), Waldermar Link, Hamburg, Germany Year published: 1981.

Haruo Tsuji, et al., *Ceramic Interspinous Block (CISB) Assisted Anterior Interbody Fusion*, Journal of Spinal Disorders, vol. 3, No. 1, pp. 77-86, (c)1990 Raven Press, Ltd., New York.

Richard W. Porter, MD, FRCS, FRCSE, *Spinal Stenosis and Neurogenic Claudication*, SPINE vol. 21, No. 17, pp. 2046-2052, (c)1996, Lippincott-Raven Publishers.

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick at al., "Two-Point Fixation of the Lumbar Spine Differential Stability in Rotation," SPINE, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp,1-7.

Buric et al., "DIAM Device For Low Back Pain In Degenerative Disc Disease 24 Months Follow-up," Advances in Minimally Invasive Surgery And Therapy For Spine And Nerves, Alexandre et al., eds., 2011, pp. 177-182, Spinger-Verlat/Wien.

Phillips et al., "Biomechanics of Posterior Dynamic Stabilizing Device (DIAM) After Facetectomy and Discectomy," The Spine Journal, 2006, vol. 6, pp. 714-722.

Taylor et al., "Device For Intervertebral Assisted Motion: Technique and Initial Results," Neurosurg. Focus, Jan. 2007, vol, 22, No. 1, pp. 1-6.

Wilke et al., "Biomechanical Effect of Different Lumbar Interspinous Implants on Flexibility and Intradiscal Pressure," Eur. Spine J., vol, 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J, 2010, vol. 123, No. 21, pp. 2974-2977.

* cited by examiner

INTERSPINOUS PROCESS IMPLANT AND METHOD OF IMPLANTATION

CLAIM OF PRIORITY

The present application claims the benefit of priority to:

This application is a continuation-in-part of U.S. patent application, entitled DISTRACTIBLE INTERSPINOUS PROCESS IMPLANT AND METHOD OF IMPLANTATION, filed May 20, 2004, Ser. No. 10/850,267, and, U.S. Provisional Patent application entitled INTERSPINOUS PROCESS IMPLANT AND METHOD OF IMPLANTATION, Patent Application No. 60/612,582, filed on Sep. 23, 2004, which applications are incorporated herein by reference.

CROSS-REFERENCE TO RELATED APPLICATIONS

This U.S. Patent Application incorporates by reference all of the following co-pending applications and issued patents:

U.S. Patent Application, entitled "Interspinous Process Implant Including a Binder and Method of Implantation," filed concurrently;

U.S. Patent Application, entitled "Interspinous Process Implant Having Deployable Wing and Method of Implantation," filed concurrently;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al;

U.S. Pat. No. 6,695,842, entitled "Interspinous Process Distraction System and Method with Positionable Wing and Method," issued Feb. 24, 2004 to Zucherman, et al;

U.S. Pat. No. 6,699,246, entitled "Spine Distraction Implant," issued Mar. 2, 2004 to Zucherman, et al; and U.S. Pat. No. 6,712,819, entitled "Mating Insertion Instruments for Spinal Implants and Methods of Use," issued Mar. 30, 2004 to Zucherman, et al.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space,* Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine,* Spine, vol. 17 at 1131 (Nov. 10, 1992). In contrast, neck flexion increases the foraminal area. Humpreys, S.C. et al., at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the cervical spine. Such implants would distract, or increase the space between, the vertebrae to increase the foraminal area and reduce pressure on the nerves and blood vessels of the cervical spine.

A further need exists for development of a minimally invasive surgical implantation method for cervical spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

BRIEF DESCRIPTION OF THE DRAWINGS

Further details of embodiments of the present invention are explained with the help of the attached drawings in which.

DETAILED DESCRIPTION

Interspinous Implants

Figure 1:
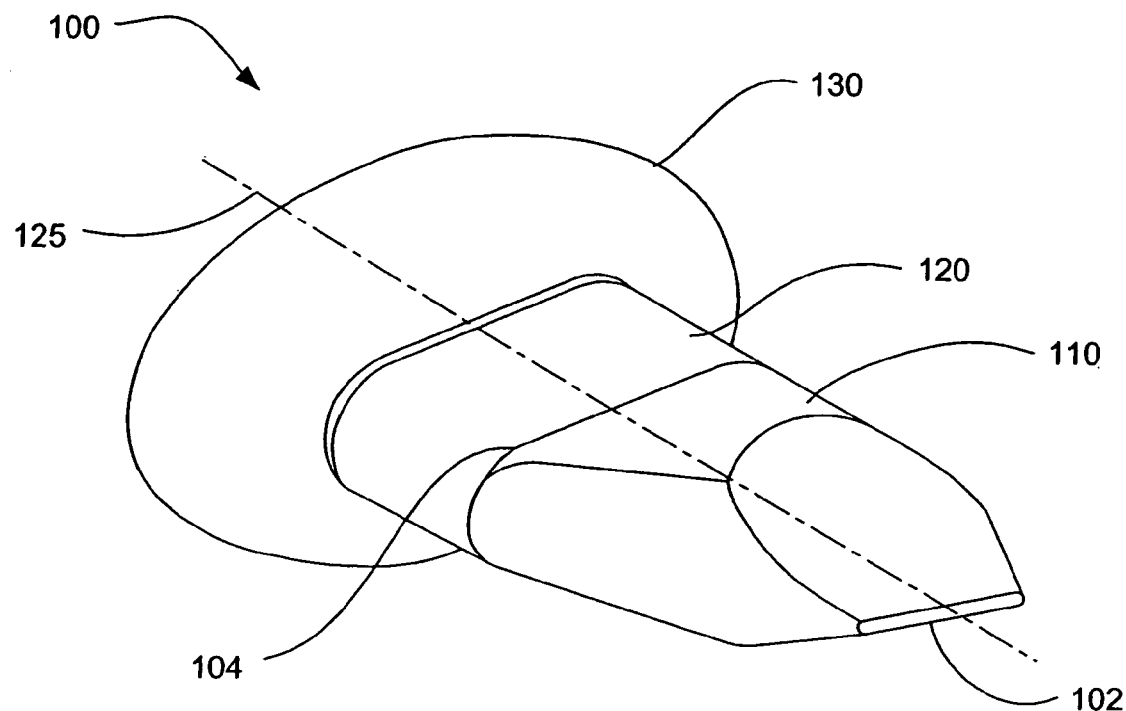
FIG. 1 is a perspective view of an embodiment of an implant in accordance with the present invention having a spacer, a distraction guide, and a wing with an elliptical cross-section.
Figure 2:
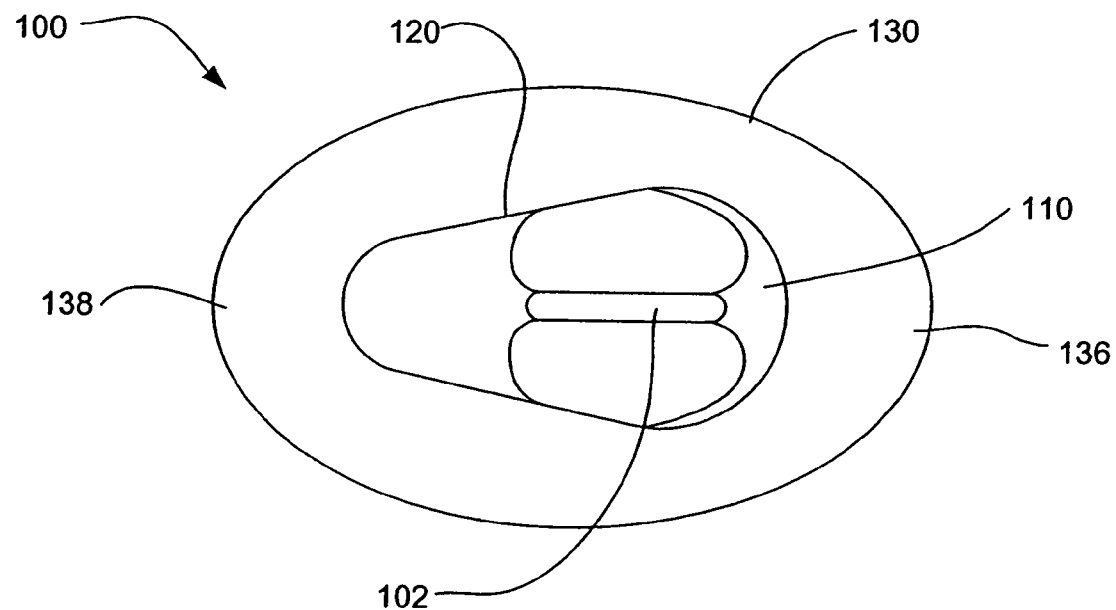
FIG. 2 is an end view of the implant of FIG. 1.

FIGS. 1 and 2 illustrate an implant 100 in accordance with an embodiment of the present invention. The implant 100 comprises a wing 130, a spacer 120, and a lead-in tissue expander (also referred to herein as a distraction guide) 110. The distraction guide 110 in this particular embodiment is wedge-shaped, i.e., the implant has an expanding cross-section from a distal end of the implant 102 to a region 104 where the guide 110 joins with the spacer 120 (referencing for the figures is based on the point of insertion of the implant between spinous processes). As such, the distraction guide functions to initiate distraction of the soft tissue and the spinous processes when the implant 100 is surgically inserted between the spinous processes. It is to be understood that the distraction guide 110 can be pointed and the like, in order to facilitate insertion of the implant 100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 1 and 2, there is no requirement to remove any of the bone of the spinous processes and no requirement to sever or remove from the body ligaments and tissues immediately associated with the spinous processes. For example, it is unnecessary to sever the *ligamentum nuchae* (supraspinous ligament), which partially cushions the spinous processes of the upper cervical vertebrae.

Figure 3:
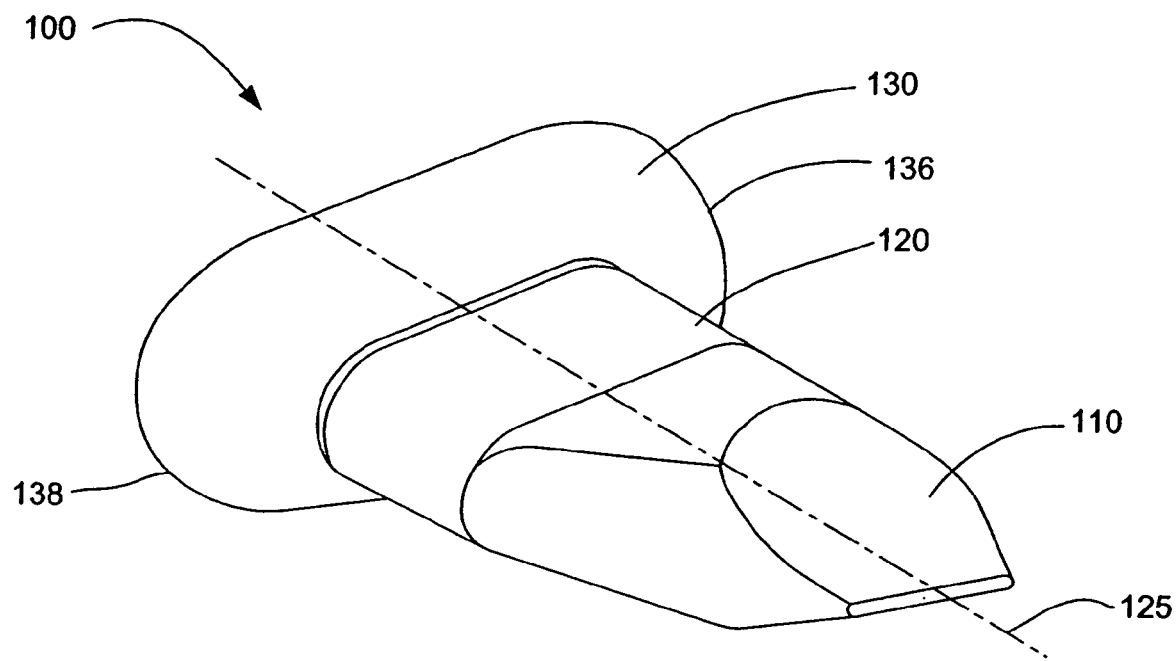
FIG. 3 is a perspective view of another embodiment of an implant in accordance with the present invention having a wing with a teardrop-shaped cross-section.

As can be seen in FIGS. 1-3, the spacer 120 can be teardrop-shaped in cross-section perpendicular to a longitudinal axis 125 of the implant 100. In this way, the shape of the spacer 120 can roughly conform to a wedge-shaped space, or a portion of the space, between adjacent spinous processes within which the implant 100 is to be positioned. In other embodiments, the spacer 120, can have alternative shapes such as circular, wedge, elliptical, ovoid, football-shaped, and rectangular-shaped with rounded corners and other shapes, and be within the spirit and scope of the invention. The shape of the spacer 120 can be selected for a particular patient so that the physician can position the implant 100 as close as possible to the anterior portion of the surface of the spinous process. The shape selected for the spacer 120 can affect the contact surface area of the implant 100 and the spinous processes that are to be subject to distraction. Increasing the contact surface area between the implant 100 and the spinous processes can distribute the force and load between the spinous frame and the implant 100.

As can be seen in FIGS. 1 and 2, the wing 130 in an embodiment can be elliptically shaped in cross-section perpendicular to the longitudinal axis 125. The dimensions of the wing 130 can be larger than that of the spacer 120, particularly along the axis of the spine, and can limit or block lateral displacement of the implant 100 in the direction of insertion along the longitudinal axis 125. As illustrated in the embodiment of FIG. 3, the wing 130 can alternatively have other cross-sectional shapes, such as teardrop, wedge, circular, ovoid, football-shaped, and rectangular-shaped with rounded corners and other shapes, and be within the spirit and scope of the invention. The wing 130 has an anterior portion 138 and a posterior portion 136.

In other embodiments, the implant 100 can include two wings, with a second wing 160 (shown in FIG. 4) separate from the distraction guide 110, spacer 120 and first wing 130. The second wing 160 can be connected to the distal end of the spacer 120. The second wing 160, similar to the first wing 130, can limit or block lateral displacement of the implant 100, however displacement is limited or blocked in the direction along the longitudinal axis 125 opposite insertion. When both the first wing 130 and the second wing 160 are connected with the implant 100 and the implant 100 is positioned between adjacent spinous processes, a portion of the spinous processes can be sandwiched between the first wing 130 and the second wing 160, limiting any displacement along the longitudinal axis 125.

Figure 4:
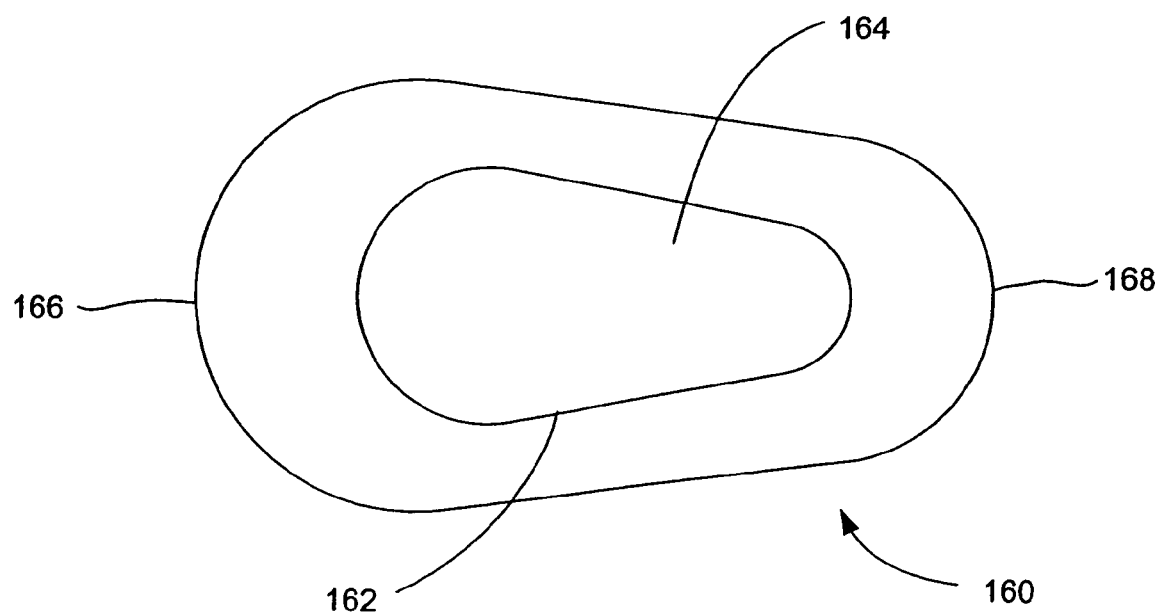
FIG. 4 is an end view of a second wing for use with the implant of FIG. 3.

As can be seen in FIG. 4, the second wing 160 can be teardrop-shaped in cross-section. The wider end 166 of the second wing 160 is the posterior end and the narrower end 168 of the second wing 160 is the anterior end. Unlike the first wing 130, however, an opening 164 is defined within the second wing 160, the opening 164 being at least partially circumscribed by a lip 162 that allows the second wing 160 to pass over the distraction guide 110 to meet and connect with the spacer 120. The second wing 160 can be secured to the spacer 120 once the second wing 160 is properly positioned. The second wing 160 can be connected with the implant after the implant 100 is positioned between the spinous processes.

It is to be understood that the implant can be made in two pieces. The first piece can include the first wing 130, the spacer 120, and the distraction guide 110. The second piece can include the second wing 160. Each piece can be manufactured using technique known in the art (e.g., machining, molding, extrusion). Each piece, as will be more fully discussed below, can be made of a material that is bio-compatible with the body of the patient. An implant can be formed with multiple pieces and with the pieces appropriately joined together, or alternatively, an implant can be formed as one piece or joined together as one piece.

Figure 5:
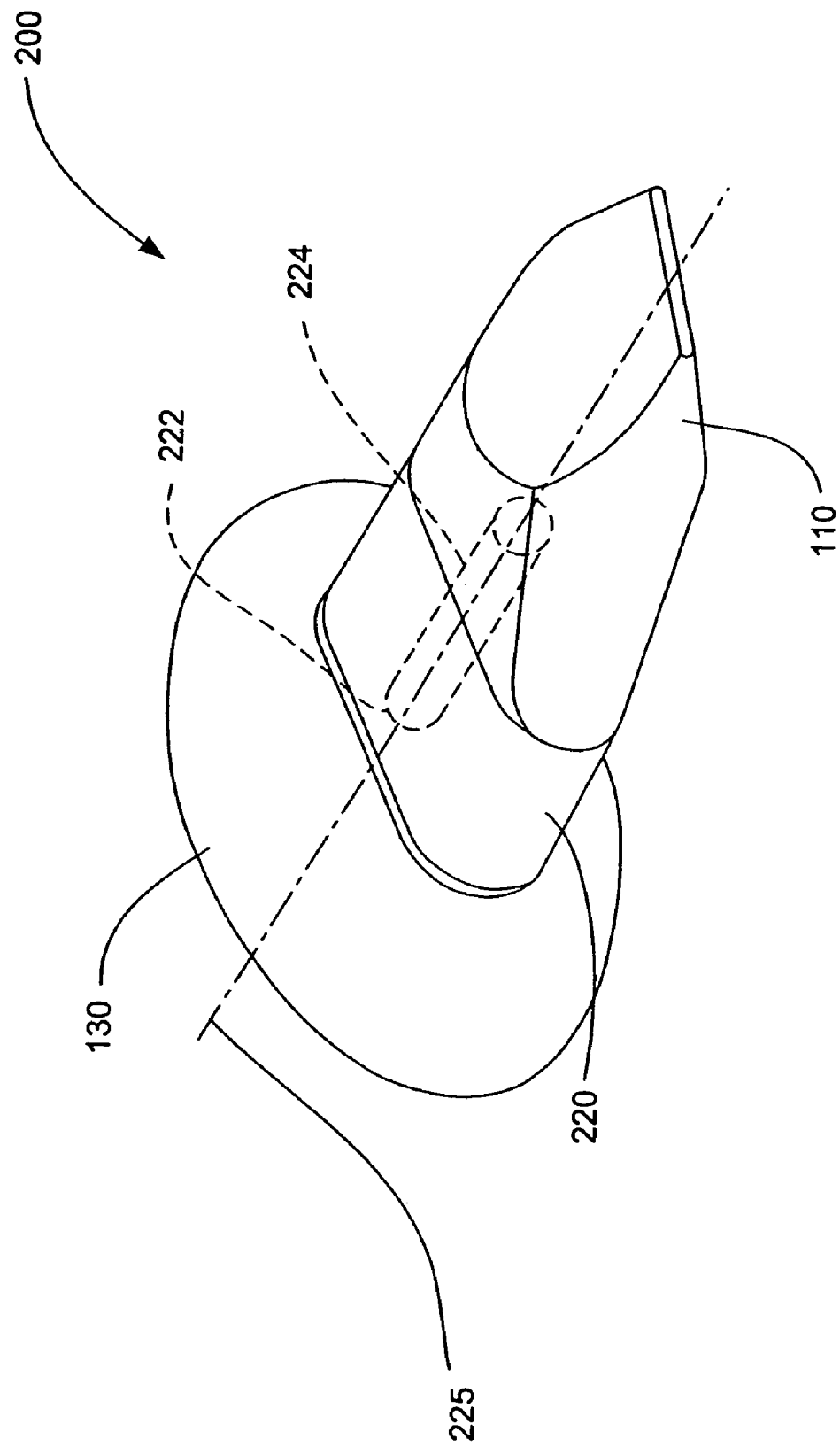
FIG. 5 is a perspective view of an embodiment of an implant in accordance with the present invention having a rotatable spacer and a wing with an elliptical cross-section.
Figure 6:
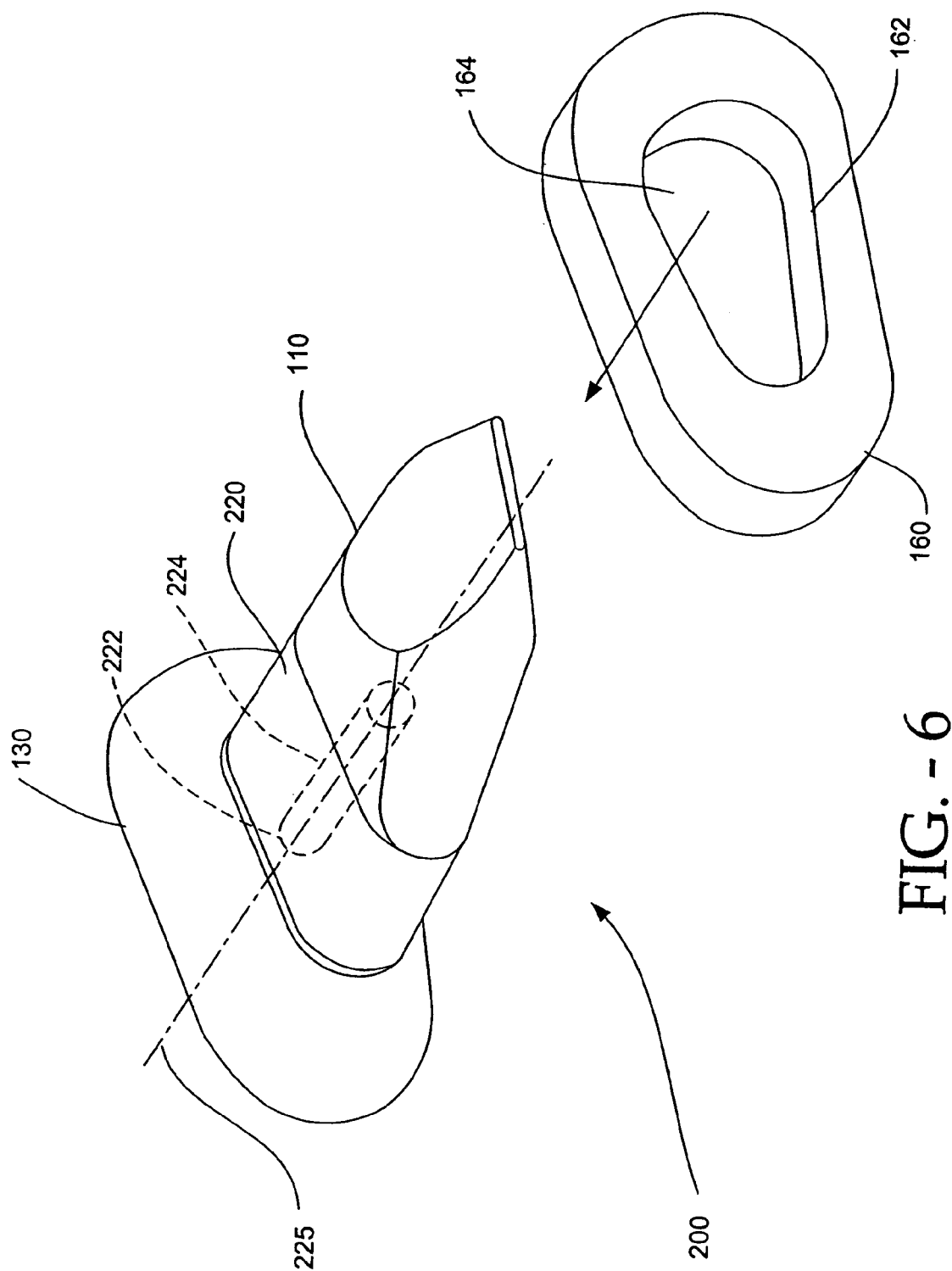
FIG. 6 is a perspective view of an embodiment of an implant in accordance with the present invention having a rotatable spacer with two wings that are teardrop-shaped in cross-section.
Figure 7:
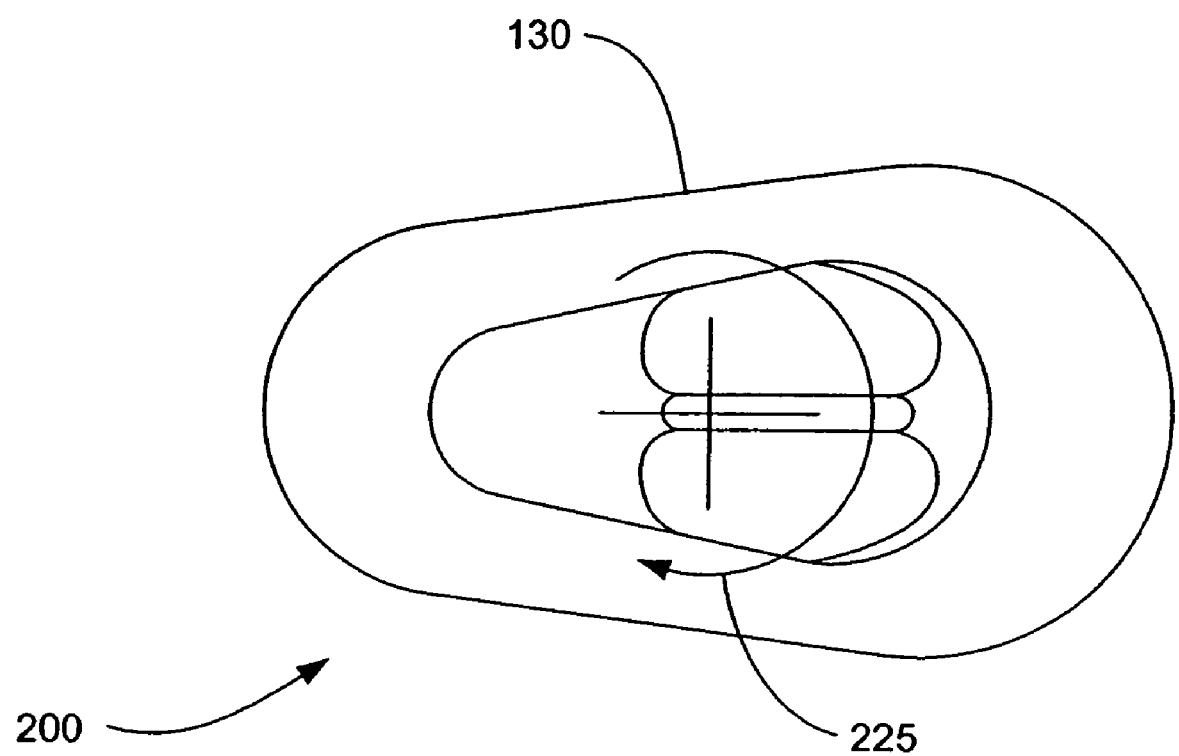
FIG. 7 depicts the axis of rotation of the implant of FIG. 6 as seen from an end view.

Further embodiments of implants in accordance with the present invention are depicted in FIGS. 5-7. In such embodiments, the spacer 220 can be rotatable about the longitudinal axis 225 relative to the first wing 130, or relative to the first wing 130 and a second wing 160 where two wings are used. The spacer 220 can be rotatable or fixed relative to the distraction guide 110. Where the spacer 220 is rotatable relative to the distraction guide 110, the spacer 220 can include a bore 222 running the length of the longitudinal axis 225, and a shaft 224 inserted through the bore 222 and connecting the distraction guide 110 with the first wing 130. It can be advantageous to position any of the implants taught herein as close as possible to the vertebral bodies. The rotatable spacer 220 can rotate to conform to or settle between adjacent spinous processes as the implant 200 is inserted and positioned during implantation, so that on average the contact surface area between the spacer 220 and the spinous processes can be increased over the contact surface area between a fixed spacer 120 and the spinous processes. Thus, the rotatable spacer 220 can improve the positioning of the spacer 220 independent of the wings 130,160 relative to the spinous processes. The embodiment of FIG. 6 includes a teardrop-shaped first wing 130, and a teardrop-shaped second wing 160, similar to the second wing 160 depicted in the embodiment of FIG. 3. As discussed below, the shape of the wings 130,160 in FIGS. 3 and 6 is such that the implants 100,200 accommodate the twisting of the cervical spine along its axis, for example, as the head of a patient turns from side to side.

Figure 8:
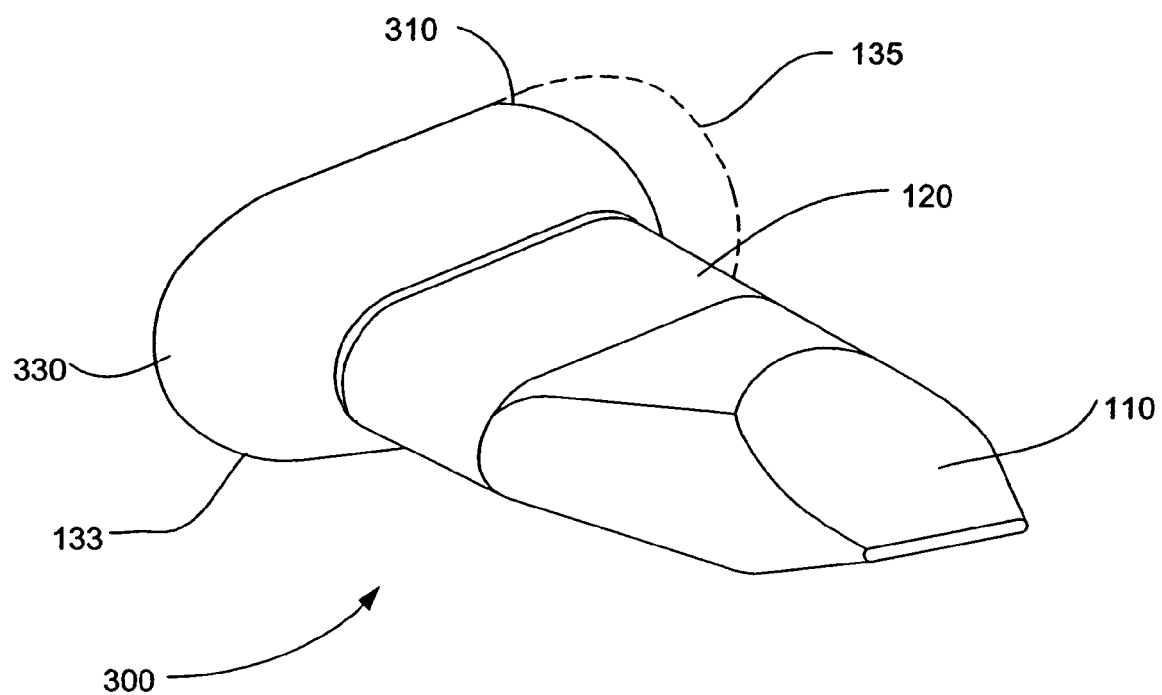
FIG. 8 is a perspective view of an embodiment of an implant in accordance with the present invention having a wing that is truncated at a posterior end.
Figure 9A:
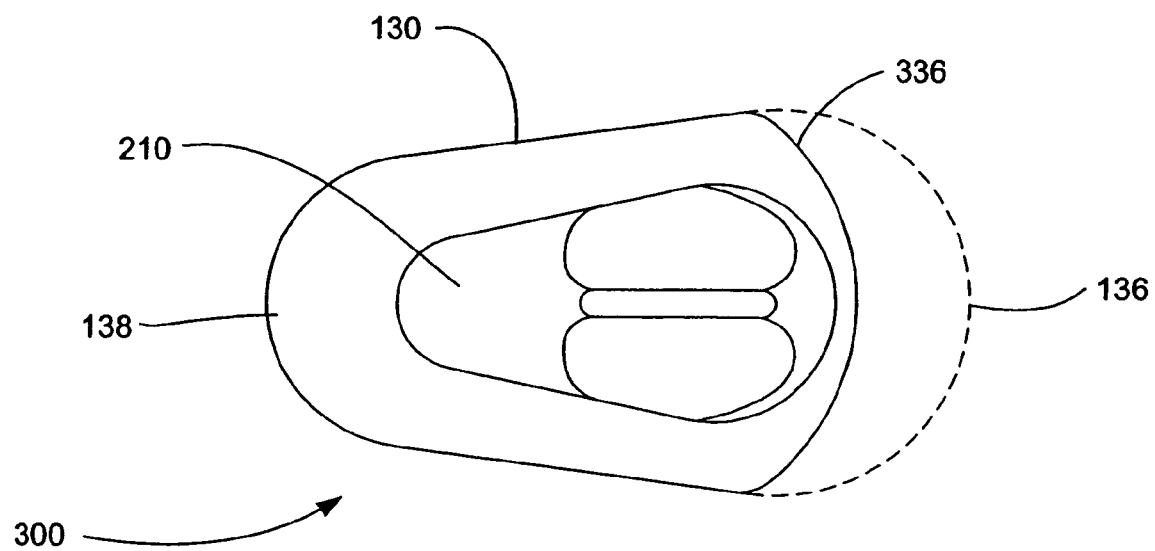
FIG. 9A is an end view of the implant of FIG. 8.
Figure 9B:
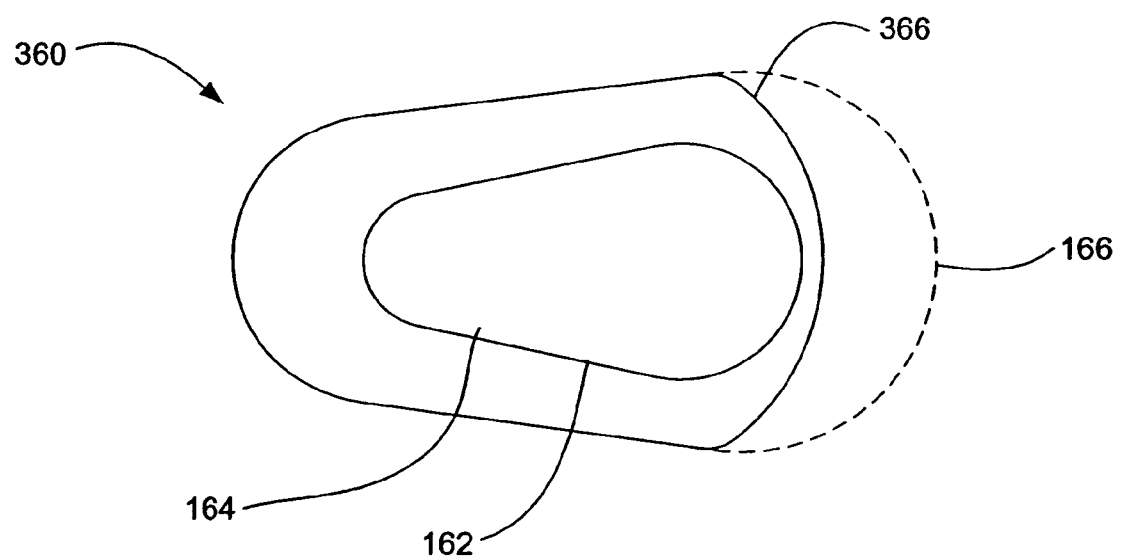
FIG. 9B is a truncated second wing for use with the implant of FIG. 9A.

FIG. 8 is a perspective view and FIG. 9A is an end view of still another embodiment of an implant in accordance with the present invention, wherein the posterior portion 336 of the teardrop-shaped first wing 330 is truncated, making the first wing 330 more ovoid in shape. In this configuration, the anterior portion 138 of the first wing 330 can be longer than the truncated posterior end 336 of the first wing 330. As in previous embodiments, the spacer 120 can alternatively be a rotatable spacer rather than a fixed spacer. FIG. 9B illustrates a second wing 360 for use with such implants 300, the second wing 360 having a truncated posterior end 366. Truncation of the posterior ends 336,366 of the first and second wings 330,360 can reduce the possibility of interference of implants 300 having such first and second wings 330,360 positioned between spinous processes of adjacent pairs of cervical vertebrae, e.g., implants between cervical vertebrae five and six, and between cervical vertebrae six and seven. During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

Figure 10:
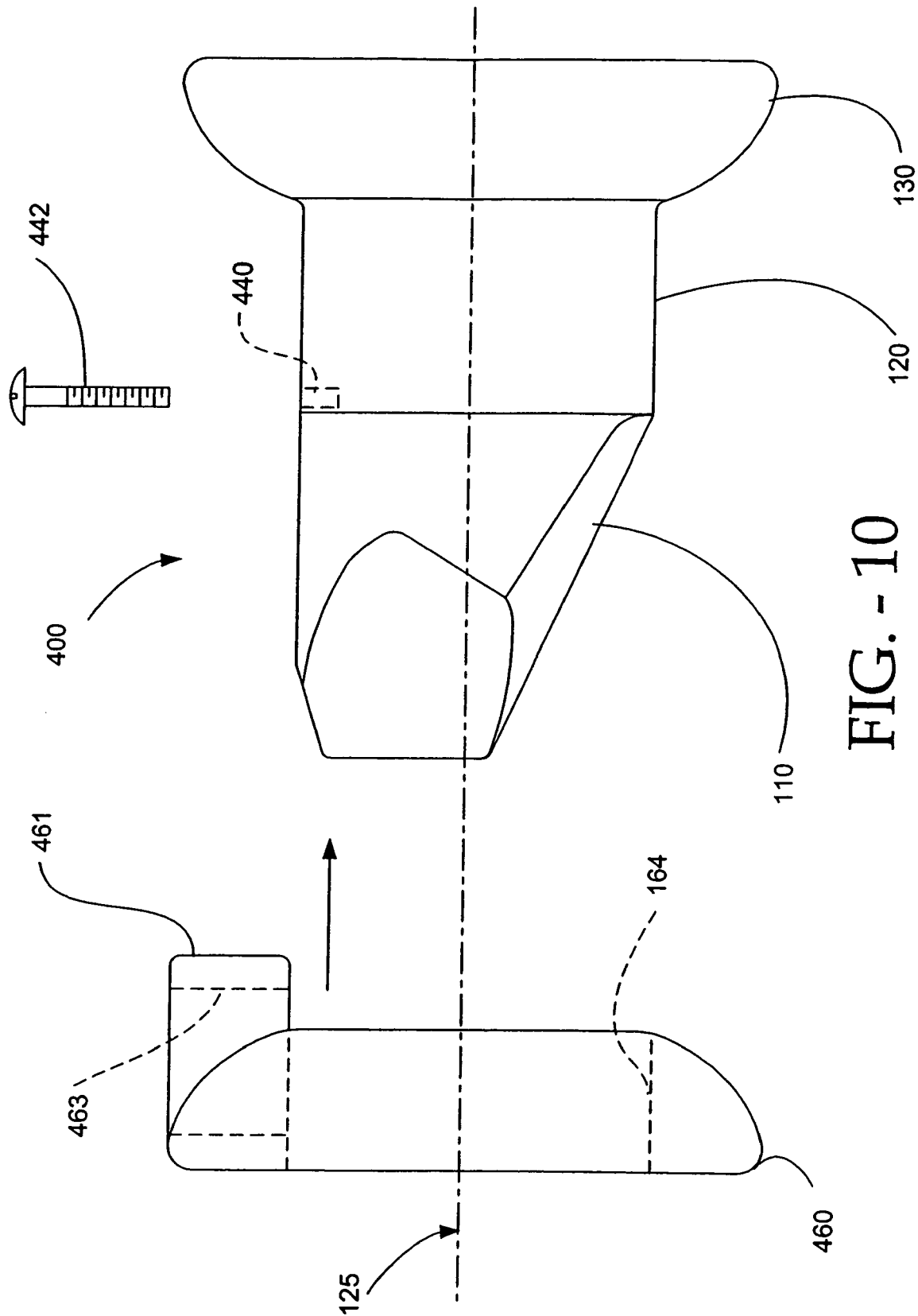
FIG. 10 is a plan view of an embodiment of an implant in accordance with the present invention wherein a screw is used to secure a second wing to the spacer.
Figure 11:
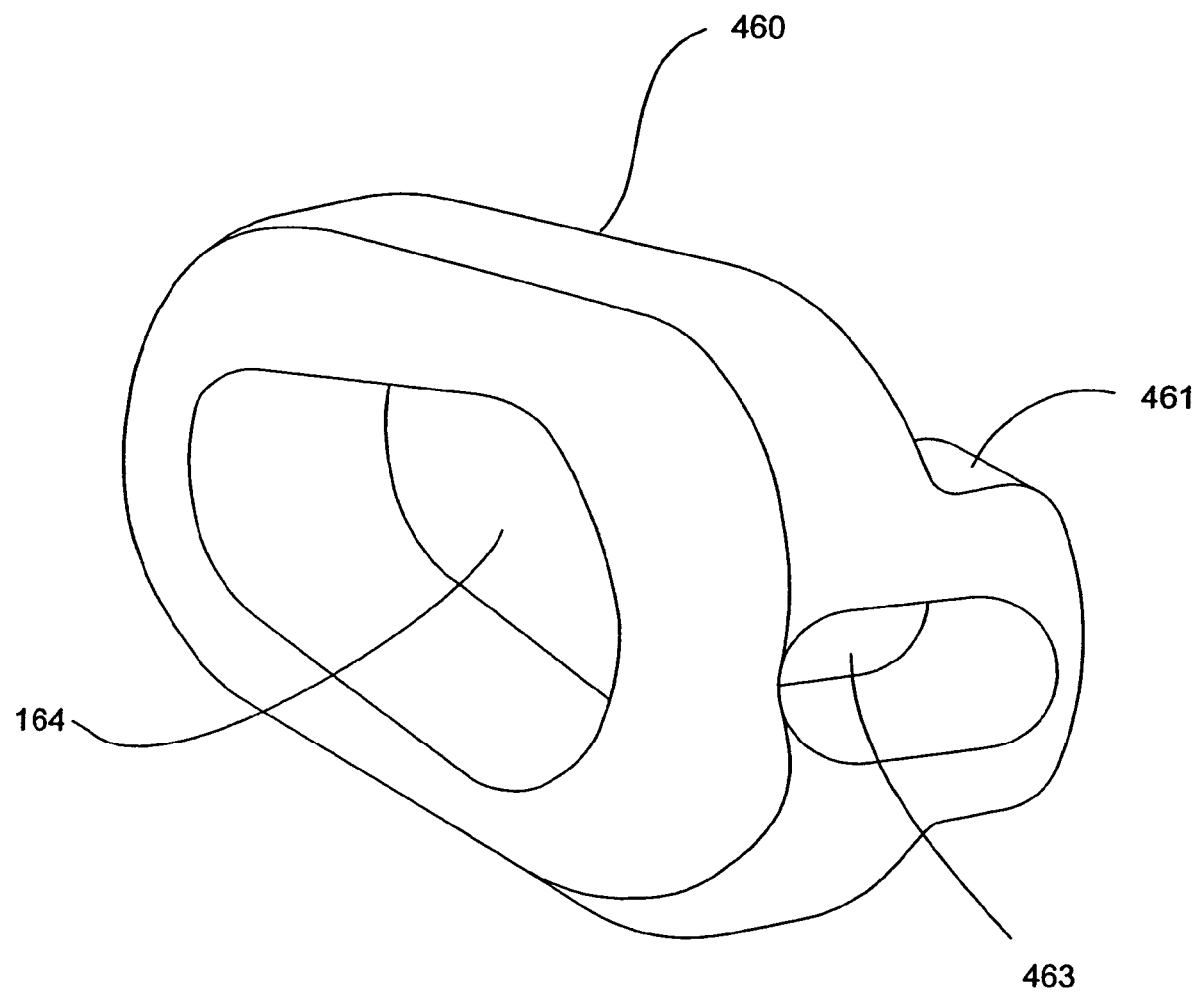
FIG. 11 is a perspective view of the second wing of FIG. 10.
Figure 12:
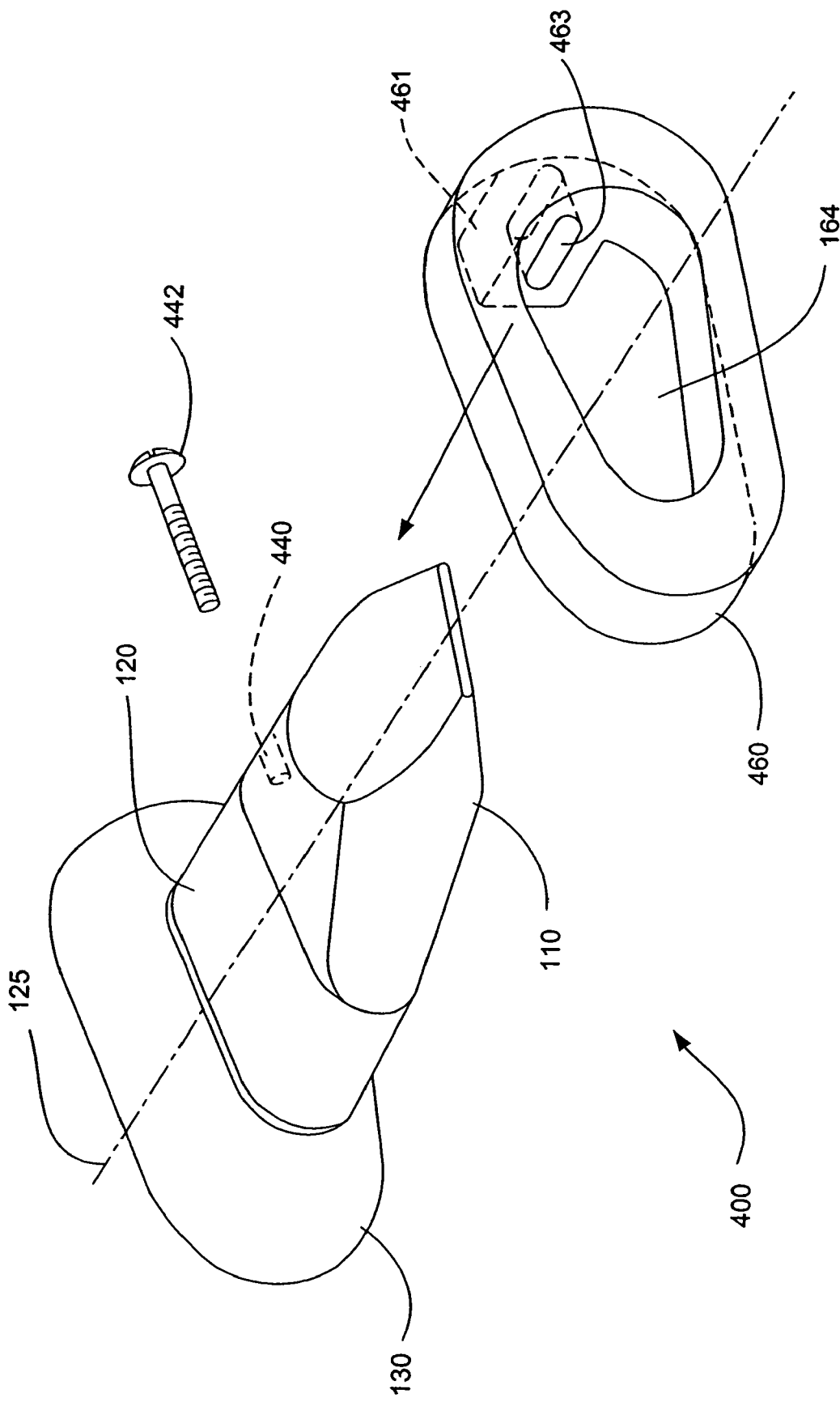
FIG. 12 is a perspective view of the implant of FIG. 10.
Figure 13A:
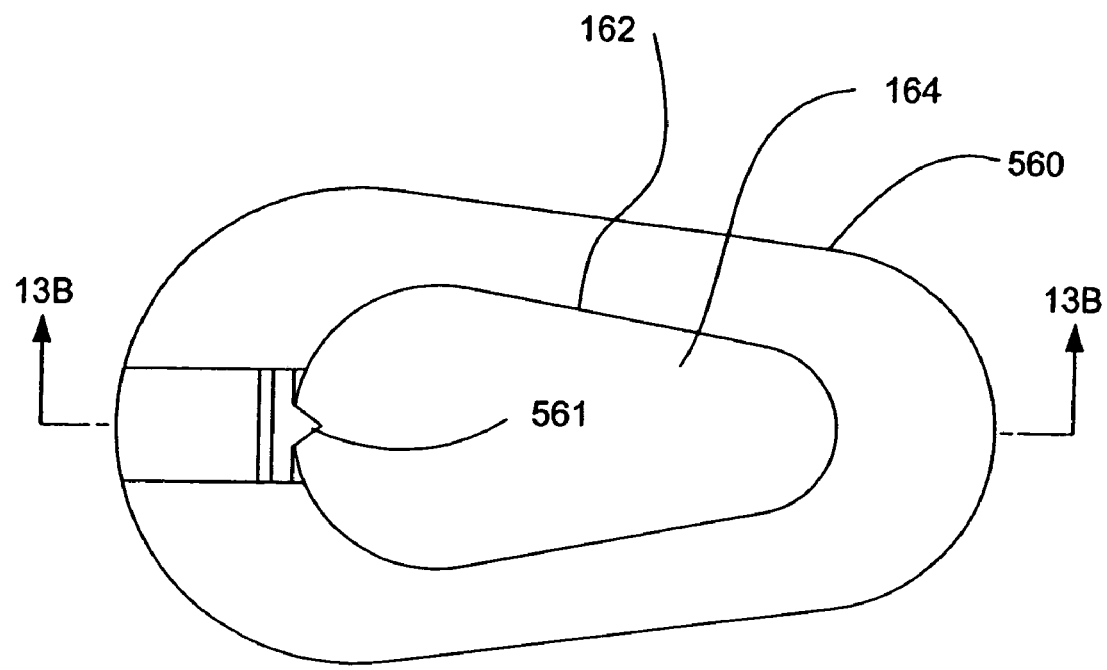
FIG. 13A is a front view of a second wing for use with some embodiments of implants of the present invention having a flexible hinge mechanism for securing the second wing to an implant.
Figure 13B:
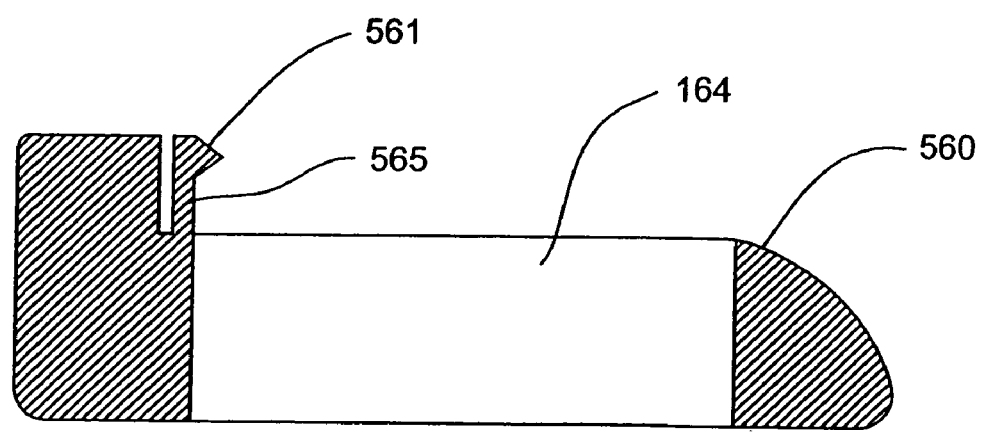
FIG. 13B is a side-sectional view of the second wing of FIG. 13A.
Figure 14A:
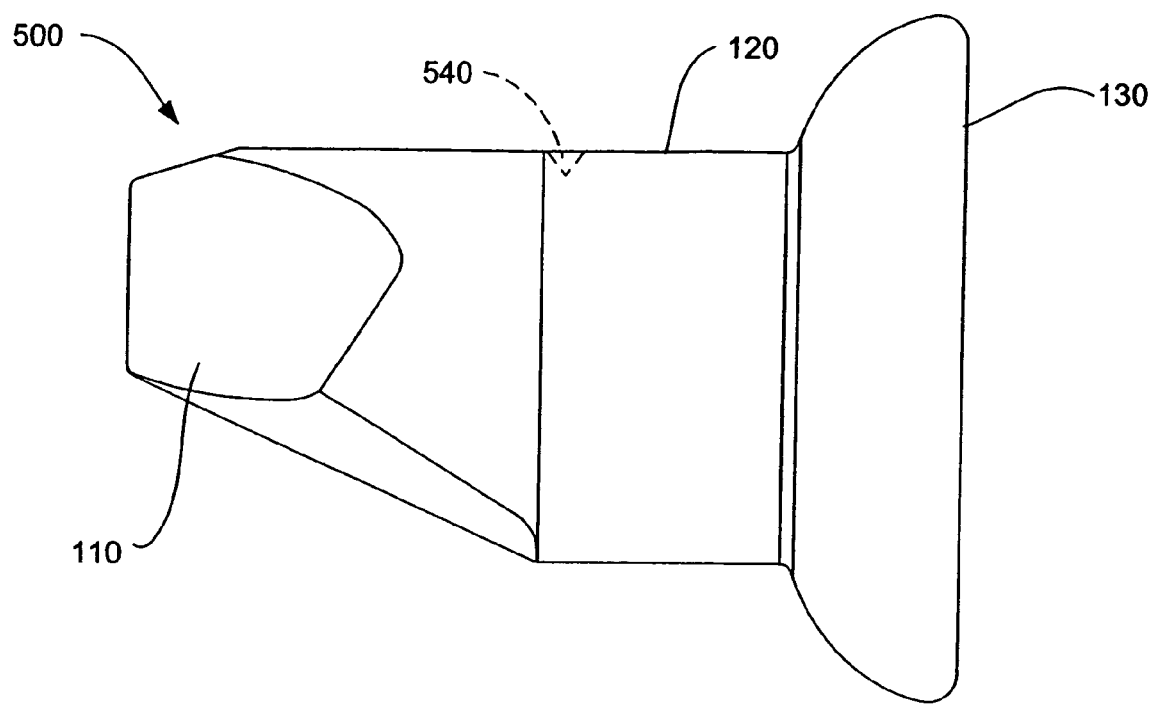
FIG. 14A is a plan view of an embodiment of an implant for use with the second wing of FIGS. 13A and 13B.
Figure 14B:
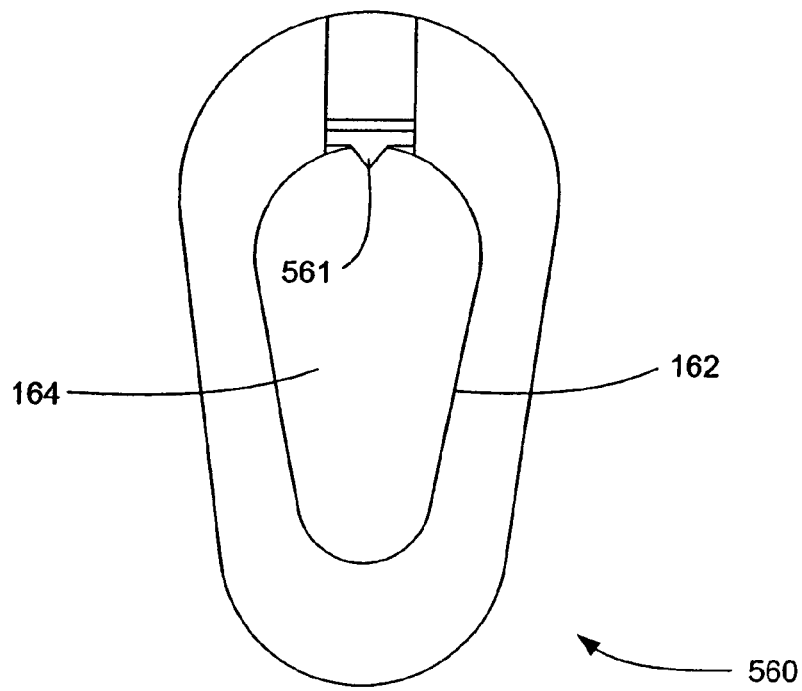
FIG. 14B is a front view of the second wing of FIGS. 13A and 13B.

With respect to the prior embodiments which have first and second wings 130,160, the second wing 160, can be designed to be interference-fit onto the spacer 120 (where the spacer is fixed) or a portion of the distraction guide 110 adjacent to the spacer 120 (where the spacer is rotatable). Where the second wing 160 is interference-fit, there is no additional attachment device to fasten the second wing 160 relative to the remainder of the implant. Alternatively, various fasteners can be used to secure the second wing relative to the remainder of the implant. For example, FIGS. 10-12 illustrate an embodiment of an implant 400 including a teardrop-shaped second wing 460 having a bore 463 through a tongue 461 at the posterior end of the second wing 460. The bore 463 is brought into alignment with a corresponding bore 440 on the spacer 120 when the second wing 460 is brought into position by surgical insertion relative to the rest of the implant 400. A threaded screw 442 can be inserted through the aligned bores 463,440 in a posterior-anterior direction to secure the second wing 460 to the spacer 120. The direction of insertion from a posterior to an anterior direction has the screw 442 engaging the bores 463,440 and the rest of the implant 400 along a direction that is generally perpendicular to the longitudinal axis 125. This orientation is most convenient when the surgeon is required to use a screw 442 to secure the second wing 460 to the rest of the implant 400. Other securing mechanisms using a member inserted into corresponding bores 463,440 on the spacer 120 and second wing 460 are within the spirit of the invention. It should be understood that a rotatable spacer 220 also can be accommodated by this embodiment. With a rotatable spacer 220, the second wing 460 would be attached to a portion of the distraction guide 110 that is located adjacent to the rotatable spacer 220.

FIGS. 13A-14B depict a further embodiment 500 wherein the second wing 560 is secured to the spacer 120 by a mechanism including a flexible hinge 565, with a protrusion 561 on the end of the hinge 565 adjacent to the lip 562 of the opening 564 defined by portions of the second wing 560. The securing mechanism also encompasses an indentation 540 on the spacer 120, wherein the indentation 540 accommodates the protrusion 561 on the end of the flexible hinge 565. During surgery, after insertion of the distraction guide 110, spacer 120, and first wing 130, the second wing 560 is received over the distraction guide 110 and the spacer 120. As the second wing 560 is received by the spacer 120, the flexible hinge 565 and its protrusion 561 deflect until the protrusion 561 meets and joins with the indentation 540 in the spacer 120, securing the second wing 560 to the spacer 120. Again in embodiments where the spacer can rotate, the indentation 540 is located on an end of the distraction guide 110 that is adjacent to the rotatable spacer 220. With respect to the flexible hinge 565, this hinge is in a preferred embodiment formed with the second wing 560 and designed in such a way that it can flex as the hinge 565 is urged over the distraction guide 110 and the spacer 120 and then allow the protrusion 561 to be deposited into the indentation 540. Alternatively, it can be appreciated that the indentation 540 can exist in the second wing 560 and the flexible hinge 565 and the protrusion 561 can exist on the spacer 120 in order to mate the second wing 560 to the spacer 120. Still alternatively, the flexible hinge 565 can be replaced with a flexible protrusion that can be flexed into engagement with the indentation 540 in the embodiment with the indentation 540 in the spacer 120 or in the embodiment with the indentation 540 in the second wing 560. One of ordinary skill in the art will appreciate the myriad different ways with which the second wing can be mated with the implant.

Figure 15A:
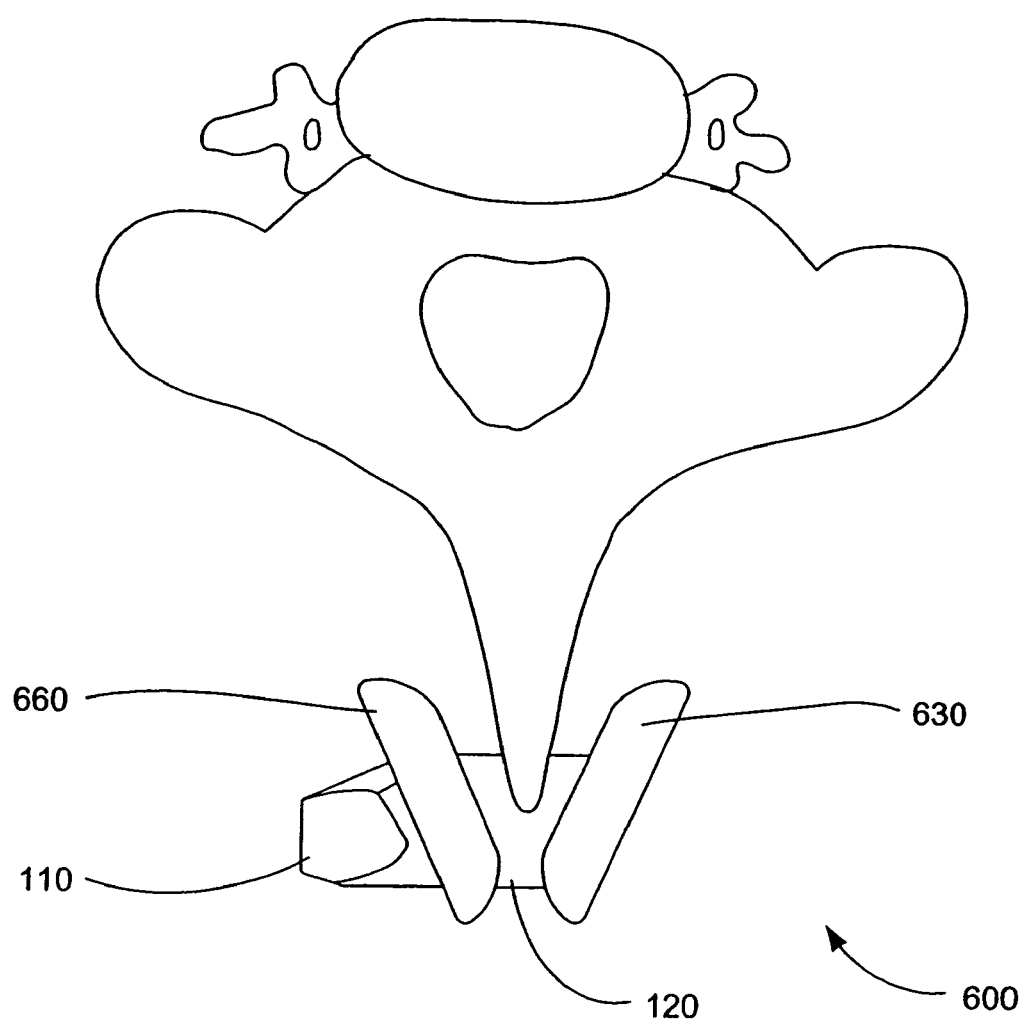
FIG. 15A is a top view of an embodiment of an implant in accordance with the present invention positioned between spinous processes of adjacent cervical vertebrae.
Figure 15B:
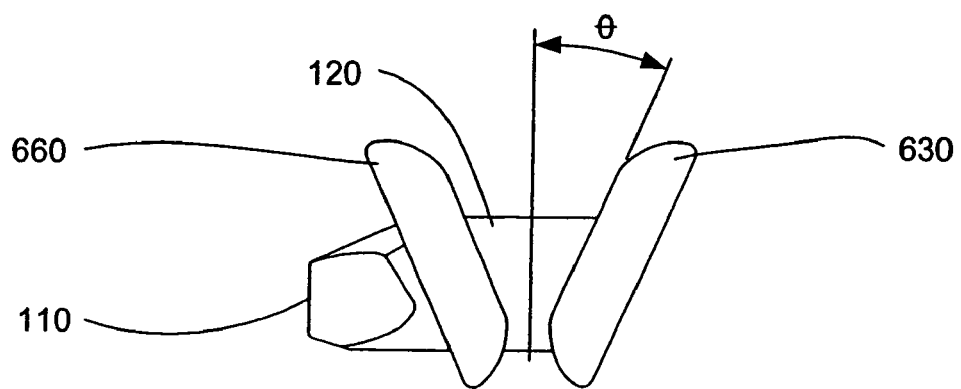
FIG. 15B is a top view of the implant of FIG. 15A showing wing orientation.
Figure 16:
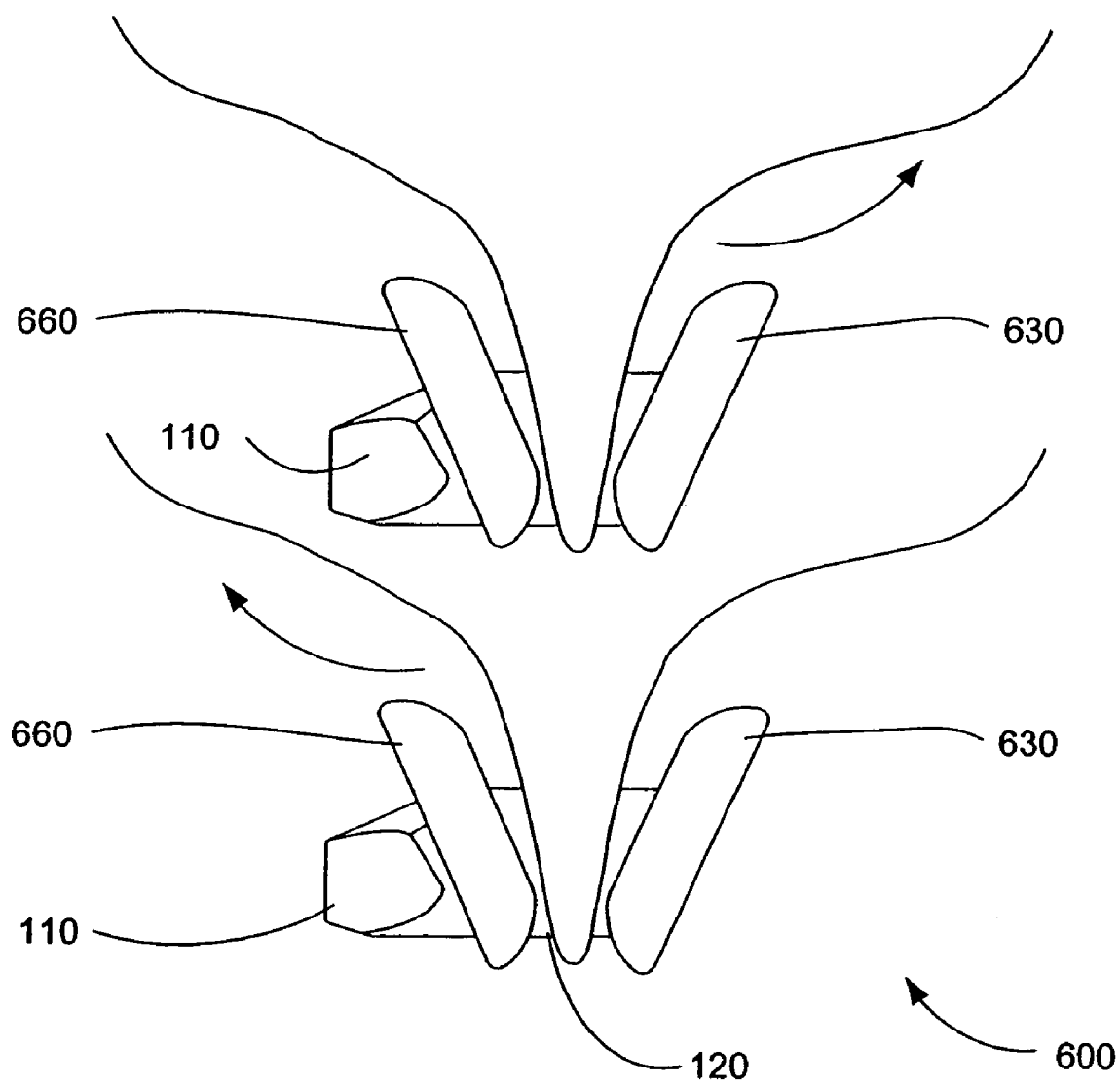
FIG. 16 is a top view of two such implants of the invention of FIGS. 15A and 15B, positioned in the cervical spine.

FIGS. 15A-16 illustrate an embodiment of an implant 600 wherein anterior ends of a first wing 630 and second wing 660 flare out at an angle away from the spacer 120 and away from each other. The cervical spinous processes are themselves wedge-shaped when seen from a top view. The first wing 630 and second wing 660 flare out so that the implant 600 can roughly conform with the wedge shape of the spinous processes, allowing the implant 600 to be positioned as close as possible to the vertebral bodies of the spine where the load of the spine is carried. The first and second wings 630,660 are positioned relative to the spacer, whether the spacer is fixed 120 or rotatable 220, so that the wings flare out as the wings approach the vertebral body of the spine. FIG. 15B is a top view of the implant 600 of FIG. 15A removed from proximity with the spinous processes. The first wing 630 is aligned at an angle with respect to an axis along the spinous processes perpendicular to the longitudinal axis (also referred to herein as the plane of symmetry). In one embodiment, the angle is about 30°, however, the angle θ can range from about 15° to about 45°. In other embodiments, other angles outside of this range are contemplated and in accordance with the invention. Likewise, the second wing 660 can be aligned along a similar, but oppositely varying range of angles relative to the plane of symmetry.

As described above in reference to FIG. 4, the second wing 660 defines an opening which is outlined by a lip. As is evident, the lip can be provided at an angle relative to the rest of the second wing 660 so that when the lip is urged into contact with the spacer 120, the second wing 660 has the desired angle relative to the spacer 120. As discussed above, there are various ways that the second wing 660 is secured to the spacer 120. FIG. 15A depicts a top view of one such implant 600 placed between the spinous processes of adjacent cervical vertebrae. FIG. 16 is a top view illustrating two layers of distracting implants 600 with flared wings 630,660.

Figure 17:
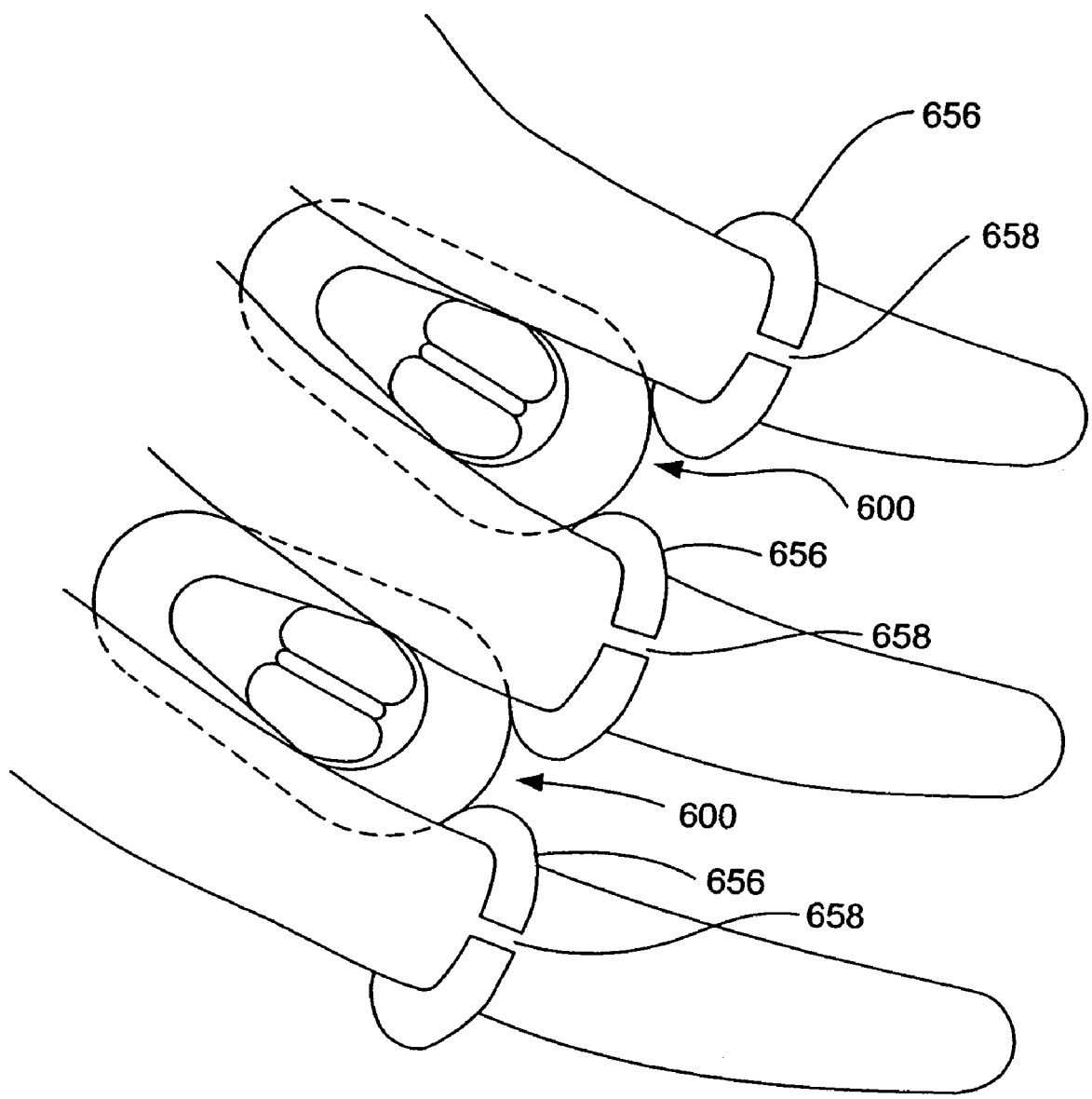
FIG. 17 is a side view of two implants of the invention positioned in the cervical spine, with stops or keeps at the proximal ends of the spinous processes.

Systems and methods in accordance with the present invention can include devices that can be used in cooperation with implants of the present invention. FIG. 17 illustrates "stops" (also referred to herein as "keeps") 656, which are rings of flexible biocompatible material, which can be positioned around the spinous processes of adjacent cervical vertebrae and located posteriorly to the implant 600. The keeps 656 can prevent posterior displacement of implants. In one embodiment, the keeps can include a ring having a slit 658. The keeps 656 can be somewhat sprung apart, so that the keep 656 can be fit over the end of the spinous process and then allowed to spring back together in order to hold a position on the spinous process. The keep 656 can act as a block to the spacer 120 in order to prevent the implant 600 from movement in a posterior direction.

Interspinous Implant with Binder

Figure 18:
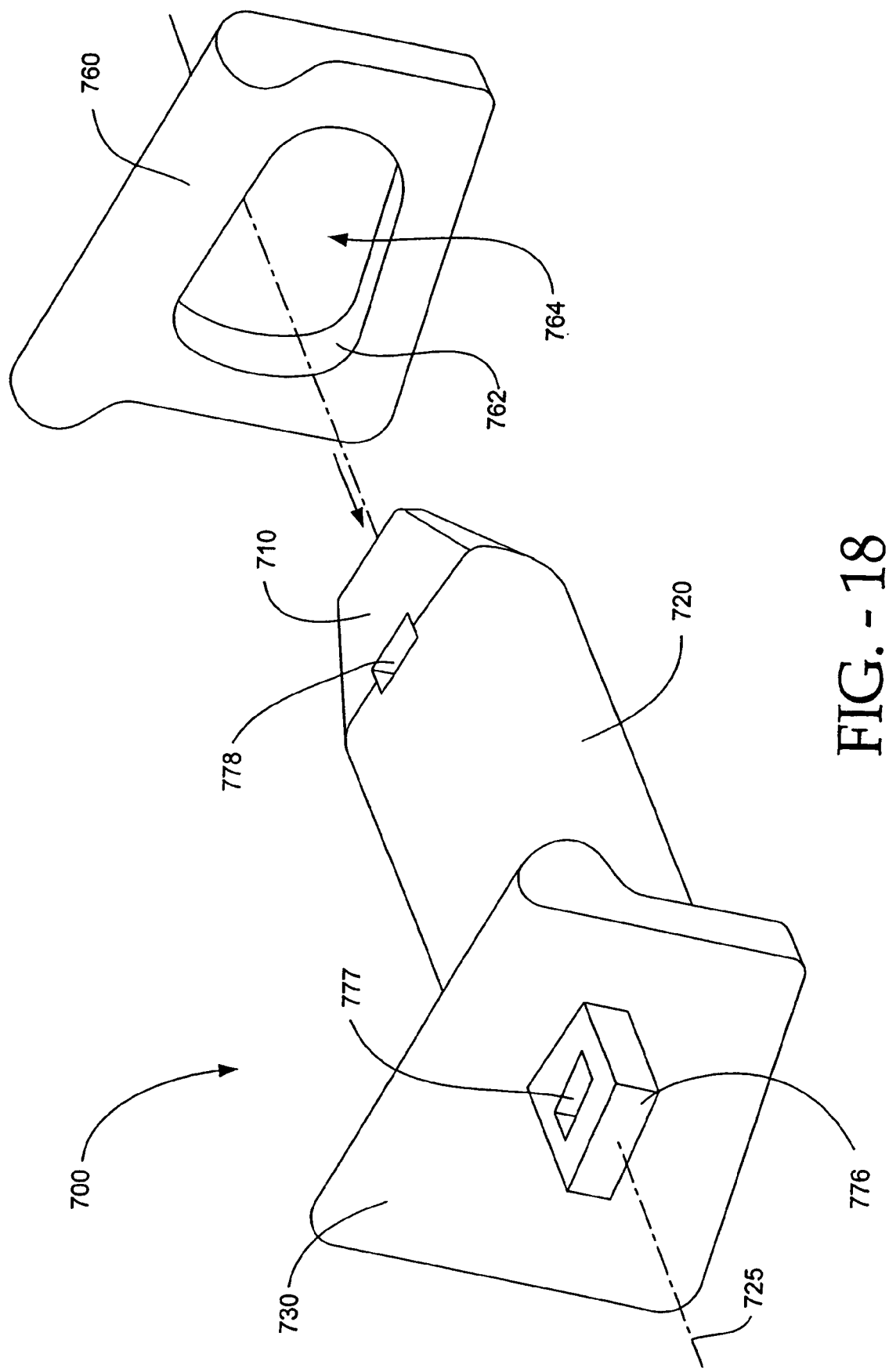
FIG. 18 is a perspective view of an alternative embodiment of an implant for use with systems and methods of the present invention, the implant including a slot formed in a portion of the distraction guide and a slotted anchor associated with the wing.

In other embodiments, implants in accordance with the present invention can include a binder for engaging adjacent spinous processes, thereby limiting relative movement of the associated cervical vertebrae due to flexion. FIG. 18 is a perspective view of one such implant. The implant 700 resembles implants described above in reference to FIGS. 1-17. In other embodiments, the implant 700 can have a shape different from those implants shown in FIGS. 1-17. As with embodiments described above, the implant 700 can include a wing 730, a spacer 720, and a distraction guide 710. As above, the distraction guide 710 as shown is wedge-shaped, and can be pointed and the like, in order to facilitate insertion of the implant between the spinous processes of adjacent cervical vertebrae.

As above, the spacer 720 is shaped to roughly conform to a wedge-like space, or a portion of the space, between adjacent spinous processes, for example as between the spinous processes of the sixth and seventh cervical vertebrae. The spacer 720 includes a cross-section perpendicular to the spacer's longitudinal axis 725 that is roughly trapezoidal in shape and having rounded edges. The spacer 720 of FIG. 18 is merely exemplary and as described above need not be shaped as shown. The shape of the spacer 720 can be selected for a particular patient, and/or a particular pair of adjacent spinous processes, and can vary substantially. Thus, in other embodiments, the spacer 720 can have alternative cross-sectional shapes, such as teardrop, circular, wedge, elliptical, ovoid, football-shaped, rectangular-shaped with rounded corners, and other cross-sectional shapes and/or can be custom fabricated for a particular patient and an anatomy of the particular spinal processes between which the implant 700 is to be placed. Thus, the spacer 720 can have a nonsymmetrical cross-sectional shape, for example where a space between adjacent spinous processes is nonsymmetrical. The ability to select a size and shape of the spacer 720 to suit a patient allows the physician to choose an implant 700 that can be placed closer to the vertebral bodies for additional support, rather than farther away from the vertebral bodies. The shape selected for the spacer 720 can define the contact surface area between the implant 700 and the spinous processes that are subject to distraction. Increasing the contact surface area between the implant 700 and the spinous processes distributes the force and load between the spinal frame and the implant 700. Generally (though not as a rule) a teardrop, trapezoidal, or wedge-shaped spacer 720 can allow for more load-bearing contact between the spacer 720 and the spinous processes of the cervical vertebrae, and embodiments having such shapes will be more particularly described.

Figure 19A:
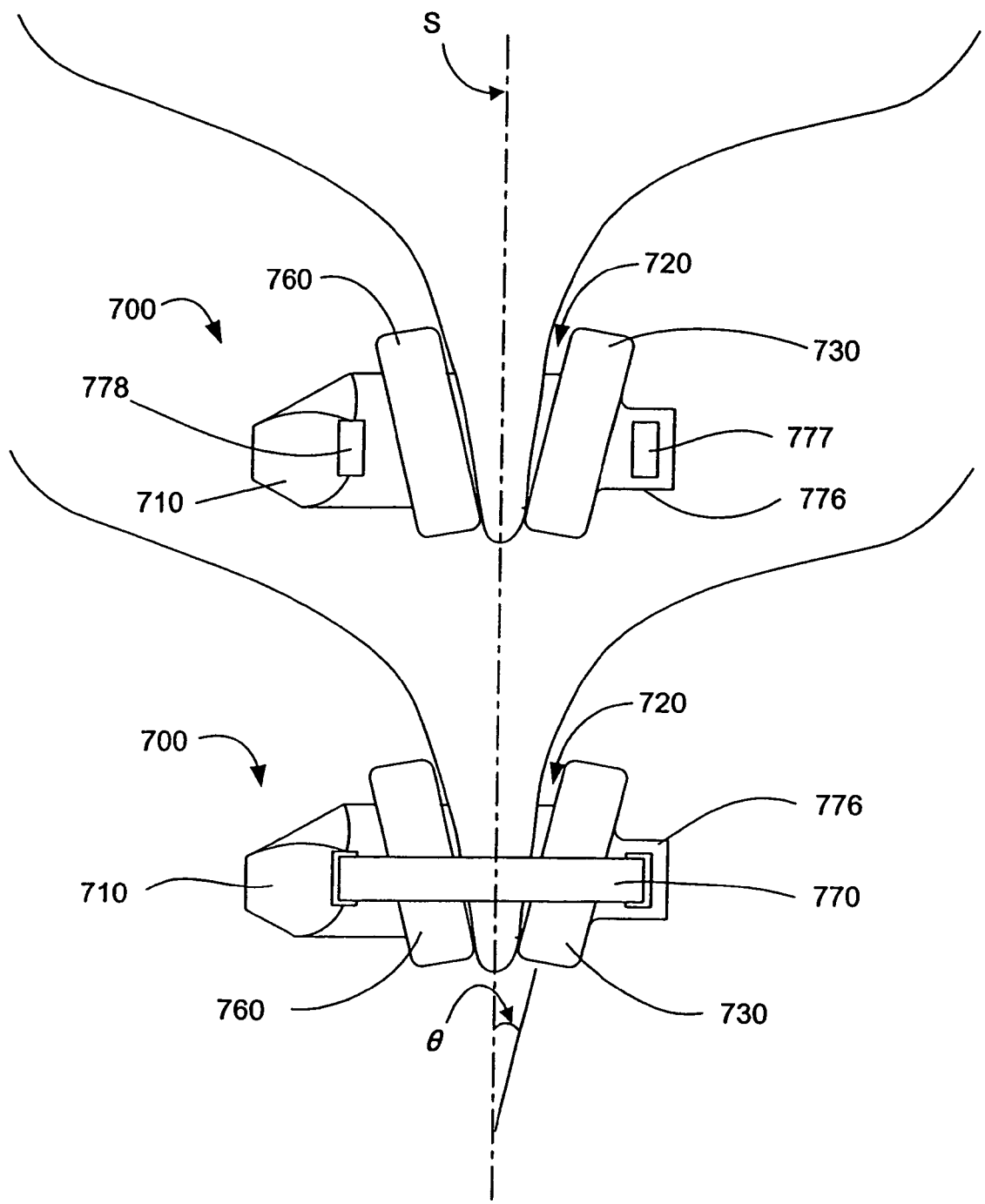
FIG. 19A is a top view of two such implants of the invention as seen in FIG. 18, positioned between corresponding adjacent spinous processes, a strap being associated with one of the implants and being positioned around adjacent spinous processes.

The implant 700 of FIG. 18 can include a wing 730 having a dimension, at least along the spine, that is larger than the distracted space between the spinous processes, thereby limiting or blocking lateral displacement of the implant 700 in the direction of insertion along the longitudinal axis 725. The wing 730 as shown has a roughly trapezoidal shape with an upper edge that bulges so that the inner surface of the wing 730 arcs slightly. The variation in thickness of the wing 730 can correspond, for example, with an estimated variation in width of the spinous process. However, the wing 730 need not be shaped as shown. In other embodiments the wing 730 can have some other shape, for example the wing 730 can be teardrop, elliptical, wedge, circular, ovoid, football-shaped, rectangular-shaped with rounded corners and other shapes, and be within the spirit and scope of the invention. As with the spacer 720, the wing 730 can alternatively have a nonsymmetrical cross-sectional shape. The shape of the wing 730 can be chosen to most easily fit into place while avoiding obstructions, such as soft tissue or bone, or implants positioned between adjacent pairs of spinous processes, while still blocking or limiting lateral displacement. As shown in FIG. 18, and further in FIGS. 19A and 19D, the wing 730 can be arranged at an angle relative to one or both of an axis along the spine and a plane of symmetry S (also referred to herein as and axis along the spinous processes) so that the wing 730 roughly corresponds to a general shape of the spinous processes. As can be seen in FIG. 19A, the adjacent spinous processes can generally have a wedge shape. Such a general shape can commonly be found in spinous processes extending from vertebrae of the cervical and thoracic region, for example. In an embodiment, the wing 730 can be arranged at an angle θ that is about 30° relative to the plane of symmetry S; however, the angle θ can range from about 15° to about 45°. In other embodiments, other angles of the first wing 730 relative to the spacer 720 outside of this range are contemplated and in accordance with the invention.

Identical implants 700, one above the other, are shown. The lower implant 700 includes a binder 770 arranged around adjacent spinous processes (only the upper spinous process is shown). The distraction guide 710 and/or the spacer 720 can include a slot 778 through which the binder 770 can be positioned. In other embodiments the distraction guide 710 and/or the spacer 720 can include a bore 878, or other cavity through which the binder 770 can be positioned (see FIG. 19D). The slot 778 is arranged so that the slot 778 is unobstructed by the spinous processes and so that the slot 778 is accessible to the binder 770, when the binder 770 is surgically implanted. The slot 778 can be included to limit shifting of the distal end of the implant 700 relative to the binder 770, and to assist in keeping the binder 770 arranged as desired and as implanted. The implant 700 can include an anchor 776 extending from the first wing 730 at a proximal end of the implant 700. The anchor 776 can include or form a slot 777 for receiving the binder 770. The anchor 776 as shown includes only a slot 777. In such embodiments, the binder 770 can be knotted, sutured, clasped, or otherwise fixed in length to place the binder 770 in tension. In other embodiments not shown, the anchor 776 can include a capture device such as a rotatable cam or clip for fixing the binder 770 in position. Such capture devices are described in greater detailed in U.S. patent application Ser. No. 11/095,680, entitled "Interspinous Process Implant Including a Binder and Method of Implantation," filed concurrently, and incorporated herein by reference. The binder 770 can be threaded or passed through the slot 777, and can be threaded through the interspinous ligaments of the adjacent spinous processes in order to engage the adjacent spinous processes.

Figure 19B:
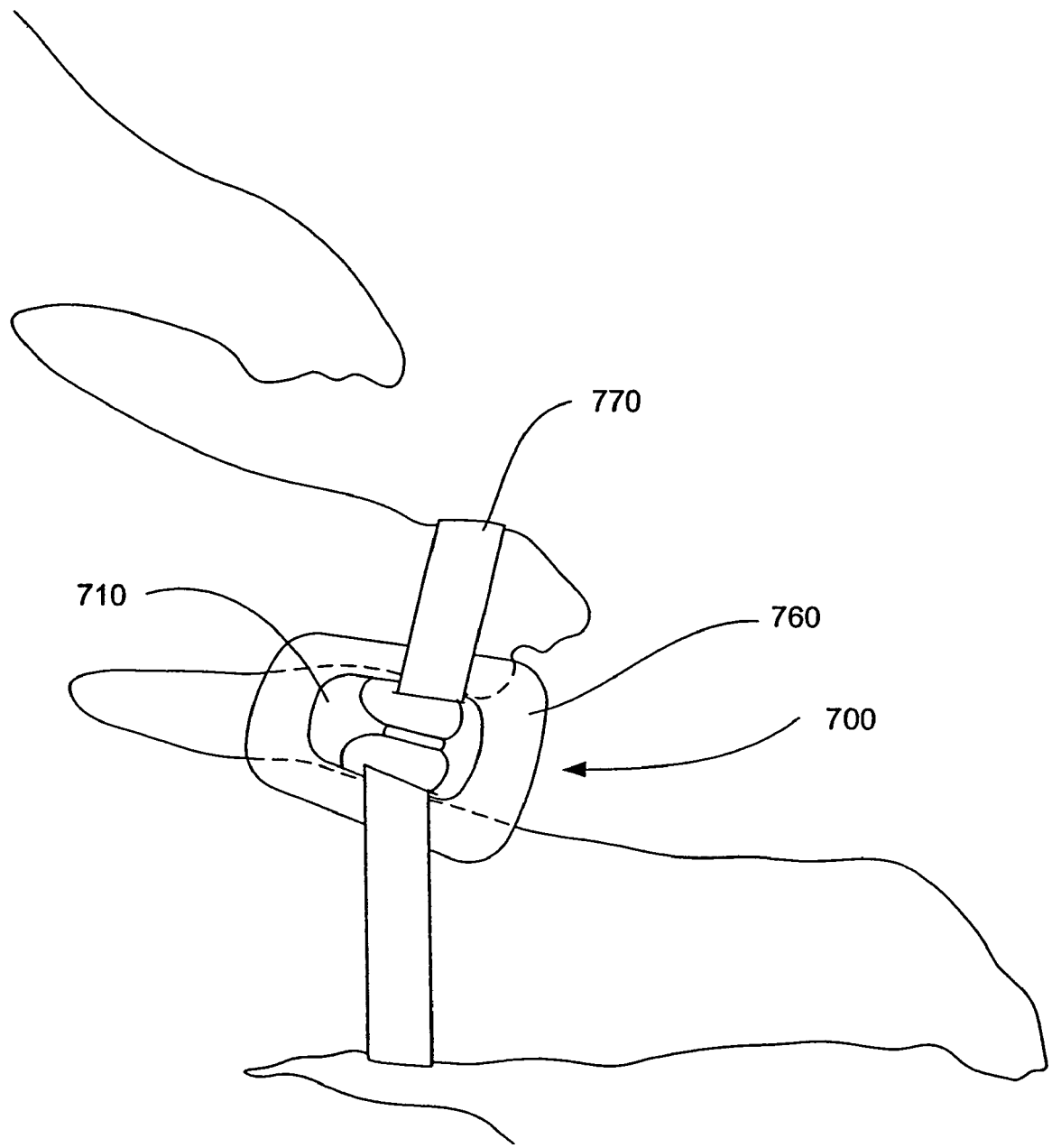
FIG. 19B is an end view of the implant of FIG. 18 positioned between adjacent spinous processes extending from respective cervical vertebrae.

In other embodiments, the implant 700 can have two wings, with a second wing 760 separate from the distraction guide 710, the spacer 720 and the first wing 730. The second wing 760 can be connected to the distal end of the spacer 720. Similar to the first wing 730, the second wing 760 can limit or block lateral displacement of the implant 700, however displacement is limited or blocked in the direction opposite insertion. When both the first wing 730 and the second wing 760 are connected with the implant 700 and the implant 700 is positioned between adjacent spinous processes, as shown in FIGS. 19A and 19B, a portion of the spinous processes can be sandwiched between the first wing 730 and the second wing 760, limiting any displacement along the longitudinal axis 725.

The second wing 760 can be shaped roughly similar to the first wing 730, but having a mirror-image orientation to accommodate a corresponding contour of the adjacent spinous processes. (Note that where the contour of the adjacent spinous processes is not symmetrical, the orientation may not be "mirror-image".) In this way, the first wing 730 and second wing 760 form a wedge shape similar to the wedge shape formed by the spinous processes. Unlike the first wing 730 the sides of the second wing 760 defines an opening 764 which is circumscribed by a lip 762 that allows the second wing 760 to pass over the distraction guide 710 to meet and connect with the spacer 720. The second wing 760 is passed over the slot 778 formed in the distraction guide 710 and/or the spacer 720 so that the slot 778 is accessible when implanting the binder 770. The second wing 760 is then optionally secured to the spacer 720 toward the end of the spacer 720 located proximally from the first wing 730. The second wing 760 is connected with the implant 700 after the implant 700 is positioned between the spinous processes.

As with the first wing 730, the second wing 760 can be aligned along a similar, but oppositely varying range of angles relative to the plane of symmetry S. The lip 762 of the opening 764 can be provided at an angle relative to the rest of the second wing 760 so that when the lip 762 is urged into contact with the spacer 720, the second wing 760 has the desired angle relative to the spacer 720. In some embodiments, the second wing 760 need not be secured where a binder 770 passes through the slot 778, as the binder 770 can prevent the second wing 760 from shifting in position. Alternatively, the second wing 760 can be secured to the spacer 720, as discussed above in reference to FIGS. 10-14B.

As with embodiments described above, the implant 700 can be made in two pieces. The first piece can include the first wing 730, the spacer 720, and the distraction guide 710. The second piece can include the second wing 760. Each piece can be manufactured using technique known in the art (e.g., machining, molding, extrusion). Each piece, as will be more fully discussed below, can be made of a material that is bio-compatible with the body of the patient. An implant can be formed with multiple pieces and with the pieces appropriately joined together, or alternatively, an implant can be formed as one piece or joined together as one piece.

FIG. 19B is an end view of an interspinous implant 700 positioned between adjacent spinous processes associated with the sixth and seventh cervical vertebrae. As can be seen, the implant 700 is arranged so that the spacer 720 roughly fills a wedge-like space between the spinous processes. The second wing 760 overlaps a portion of the spinous processes. A binder 770 is positioned around the upper surface of the spinous process associated with the sixth vertebrae and positioned around the lower surface of the spinous process associated with the seventh vertebrae and placed in tension so that the binder 770 engages the adjacent spinous processes during flexion. By engaging the adjacent spinous processes, the binder 770 limits flexion.

Figure 19C:
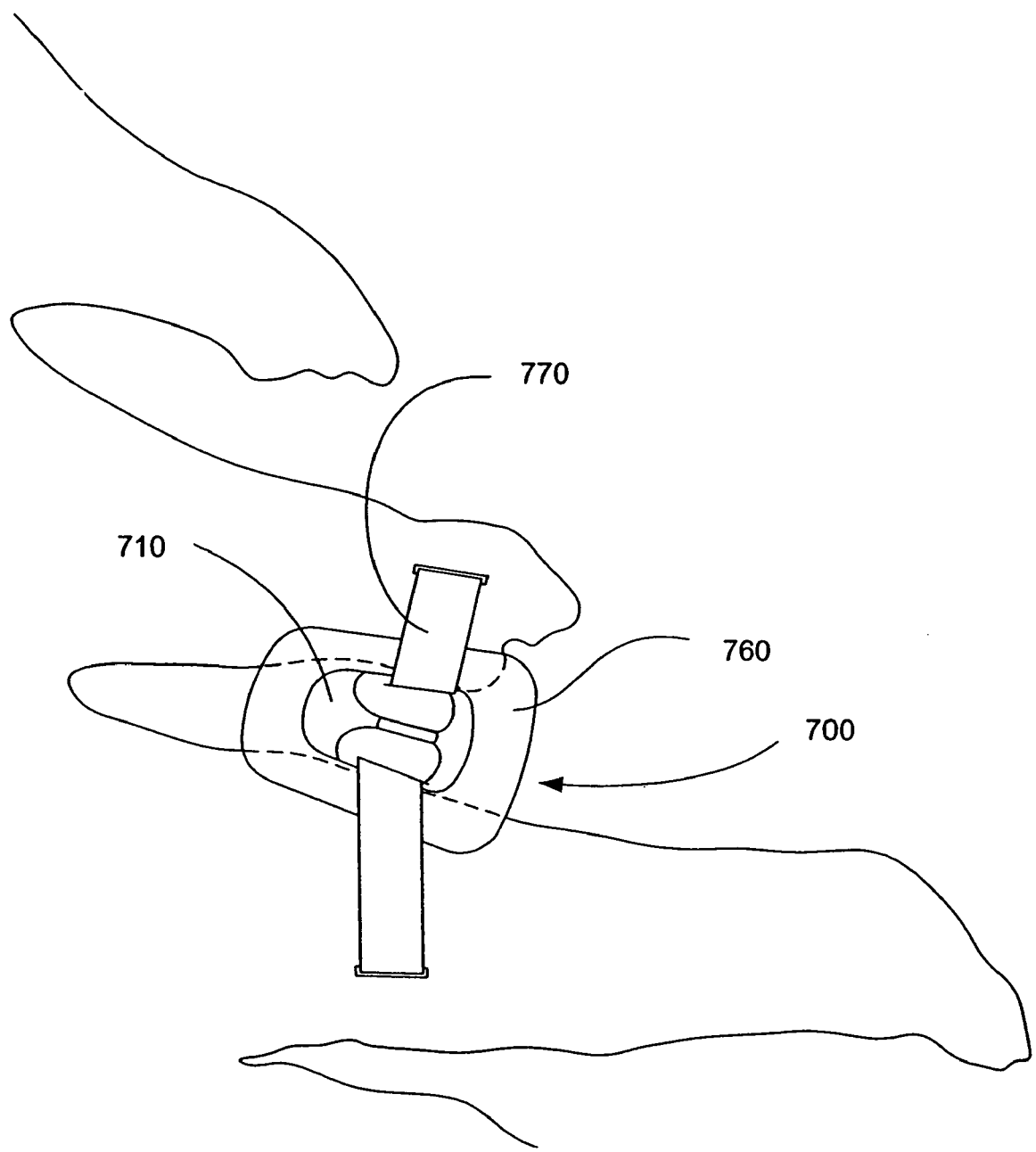
FIG. 19C is an end view of the implant of FIG. 18 positioned between adjacent spinous processes extending from respective cervical vertebrae having a strap associated with the implant positioned through a portion of each of the spinous processes.

Although in each of the embodiments described above, there is no requirement to alter any of the bone of the spinous processes, in other embodiments a physician can, if desired, alter a portion of bone from one or both of the adjacent spinous processes to receive the binder 770, thereby ensuring that the adjacent spinous processes are engaged precisely during flexion of the spine. As shown in FIG. 19C, a slot has been cut or bored in each of the adjacent spinous processes, and a binder 770 is threaded through the spinous processes and the distraction guide 710.

Figure 19D:
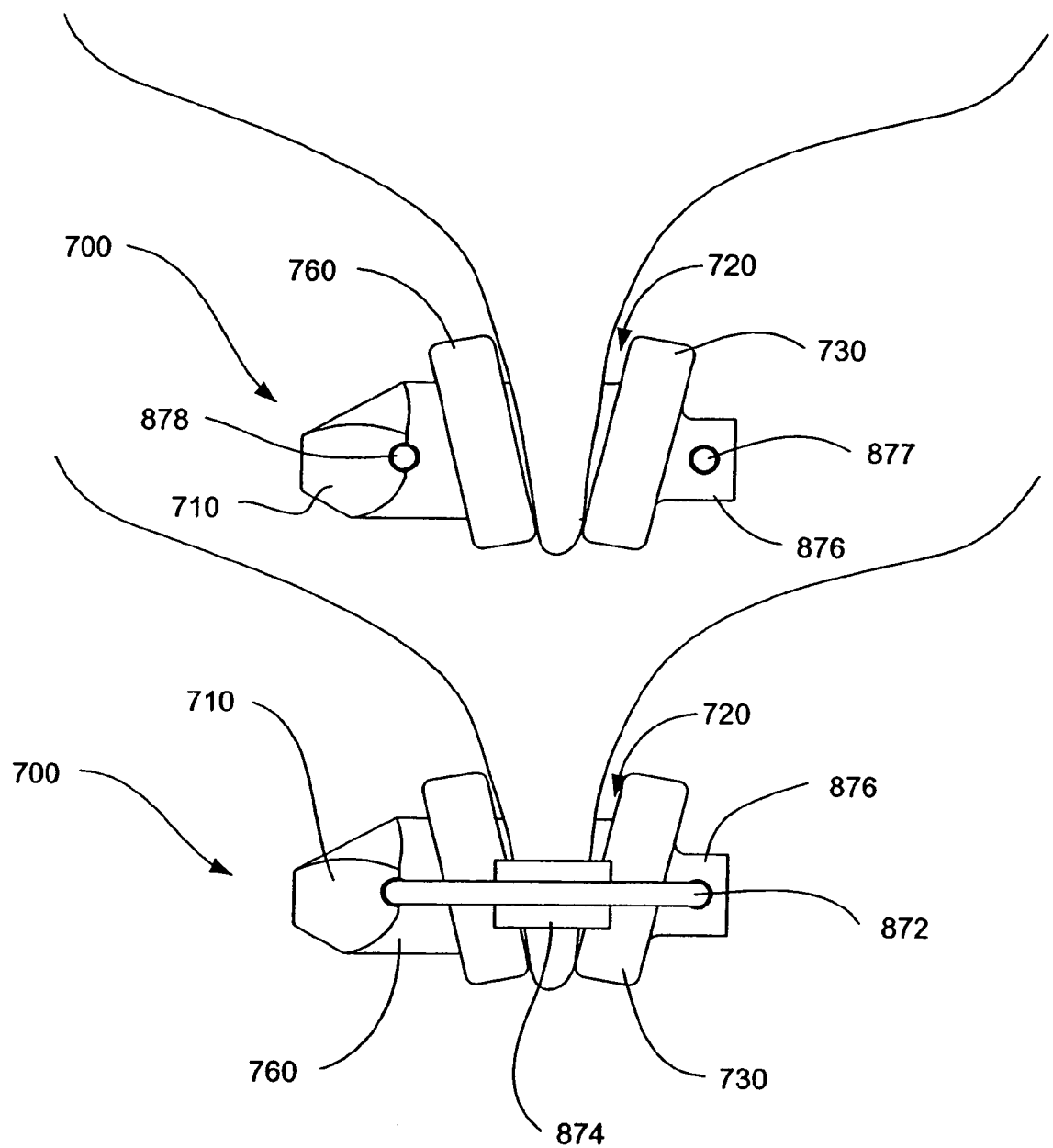
FIG. 19D is a top view of alternative implants having a bore formed in a portion of the distraction guide and in an anchor, a tether being associated with one of the implants and being positioned around adjacent spinous processes.
Figure 19E:
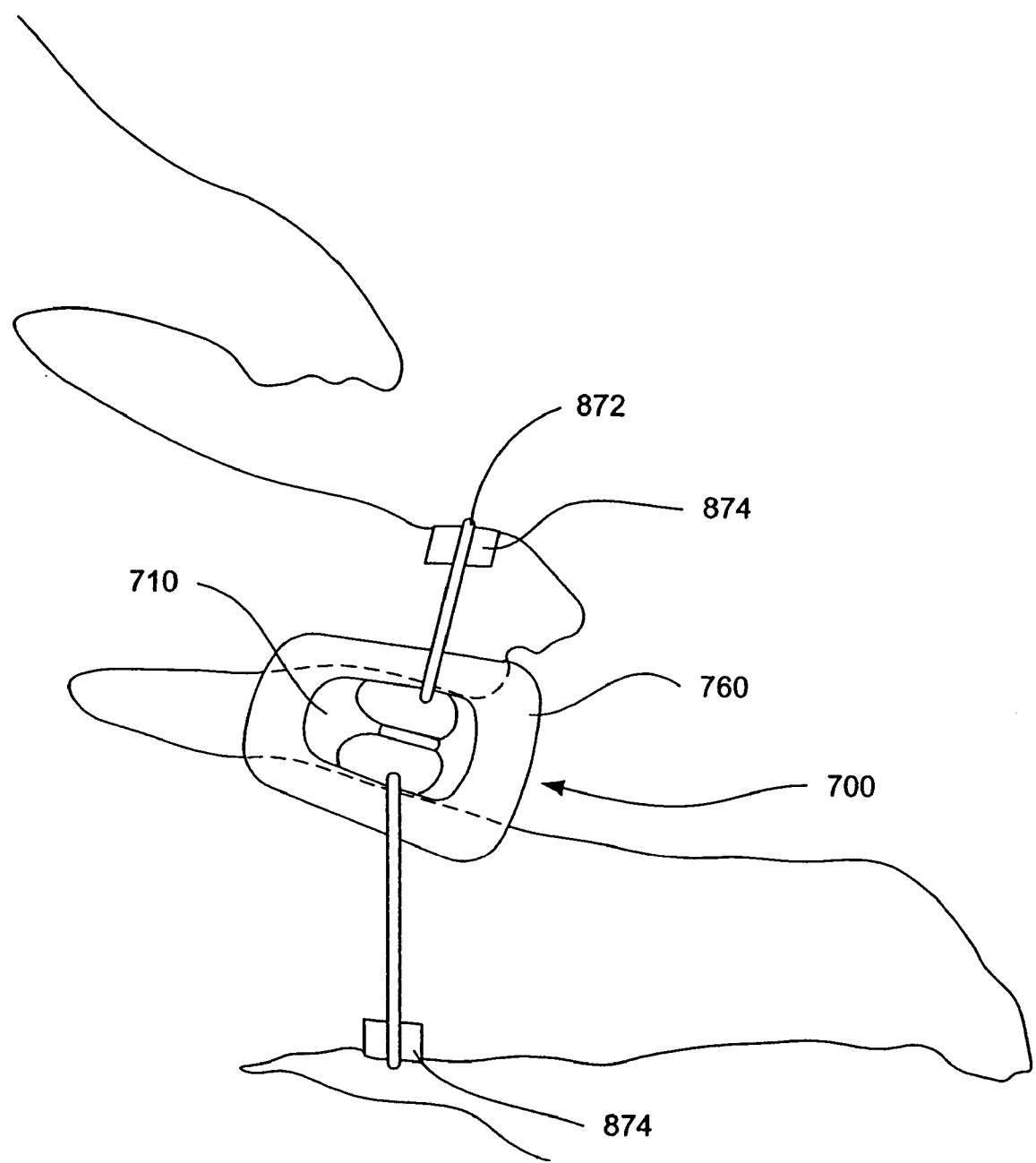
FIG. 19E is an end view of an implant, as shown in FIG. 19D.

Referring to FIGS. 19D and 19E, in alternative embodiments the binder can comprise a tether 872. In such embodiments, the anchor 876 can include either a bore, a slot, or some other cavity through which the tether can pass and preferably (though not necessarily) be captured. Likewise, the distraction guide 710 and/or the spacer 720 can include either a bore 878, a slot or some other cavity through which the tether 872 can pass and preferably be captured. Because the tether 872 engages a smaller surface area of the spinous processes, stress can be increased at points of contact. A load spreader 874 (also referred to herein as a pad) made from a biologically compatible material can be associated with the tether 872, and can protect the spinous processes from damage when the tether 872 restrains relative motion between the adjacent spinous processes. As can be seen in FIG. 19E, the load spreader 874 engages the upper surface and distributes the load applied by the tether 872 across a surface area roughly similar to the surface area contacted by the strap 870 of FIGS. 19A and 19B.

In various embodiments, the binder can comprise a strap, ribbon, tether, cord, or some other flexible (or semi-flexible), and preferably threadable structure. The binder 770,870,872 and load spreader 874 can be made from a biocompatible material. In an embodiment, the binder 770,870,872 and load spreader 874 can be made from a braided polyester suture material. Braided polyester suture materials include, for example, Ethibond, Ethiflex, Mersilene, and Dacron, and are nonabsorbable, have high tensile strength, low tissue reactivity and improved handling. In other embodiments, the binder 770,870,872 and load spreader 874 can comprise stainless steel (i.e., surgical steel), which can be braided into a tether or woven into a strap, for example. In still other embodiments, the binder 770,870,872 and load spreader 874 can made from some other material having similar desired properties.

Expandable Interspinous Implants

Figure 20:
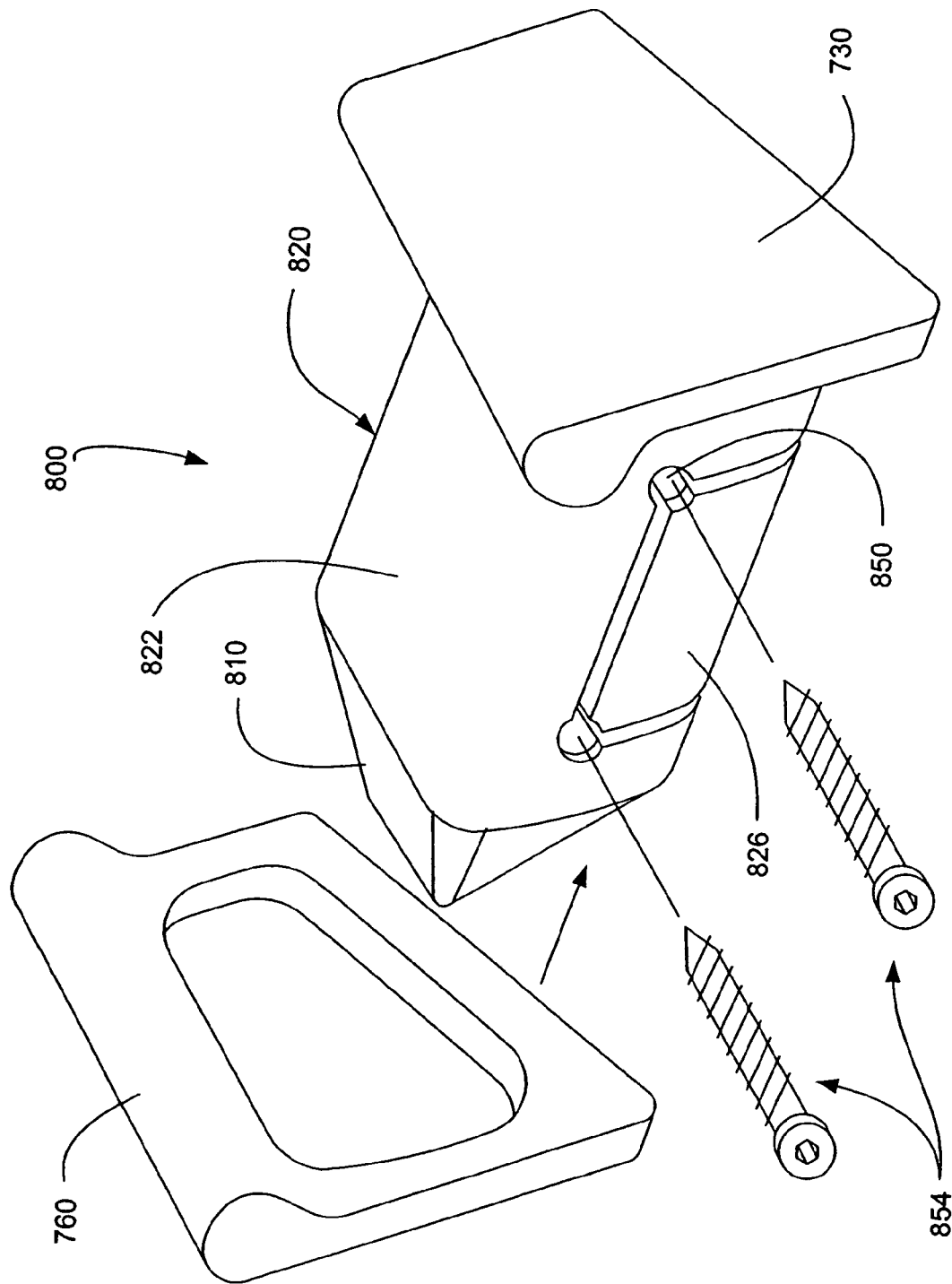
FIG. 20 is a perspective view of still another embodiment of an implant for use with systems and methods of the present invention.

In still other embodiments, implants in accordance with the present invention can be expandable in situ. FIG. 20 is a perspective view of one such implant 800. The implant 800 can include a spacer 820, a first wing 730, and a distraction guide 810. As above, the implant 800 can further include a second wing 760. The first wing 730 and the second wing 760 are as described above in reference to FIG. 18 and can likewise vary in shape and arrangement. The spacer 820 can include a main portion 822 and an expansion portion 826 that can be urged away from the main portion 822 by one or more inserts 854 (e.g., screws, wedges). The spacer 820 can have an unexpanded cross-sectional shape resembling spacers described above in reference to FIGS. 1-18. In other embodiments, the spacer 820 can have an unexpanded cross-sectional shape different from spacers described in reference to FIGS. 1-18. In some embodiments the main portion 822 and the expansion portion 826 can include contact surfaces (i.e., surfaces that contact and support a corresponding surface of a spinous process) having different shapes, thereby allowing the spacer to accommodate a geometry of the adjacent spinous processes between which the implant is to be placed.

Figure 21A:
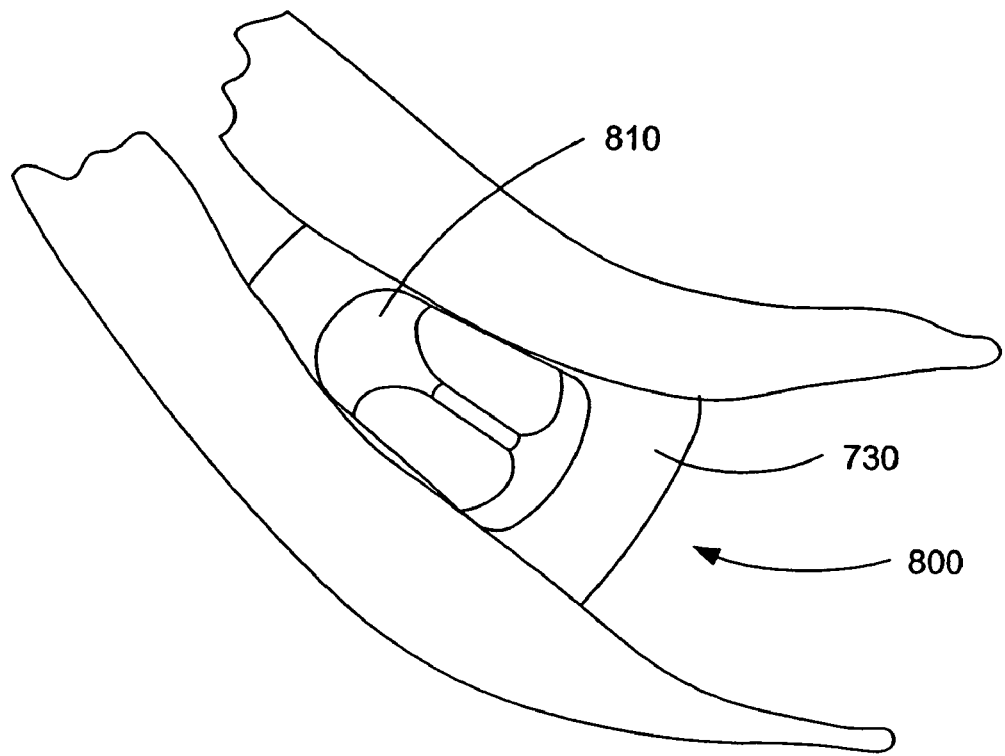
FIG. 21A is an end view of the implant of FIG. 20 positioned between adjacent spinous processes.
Figure 21B:
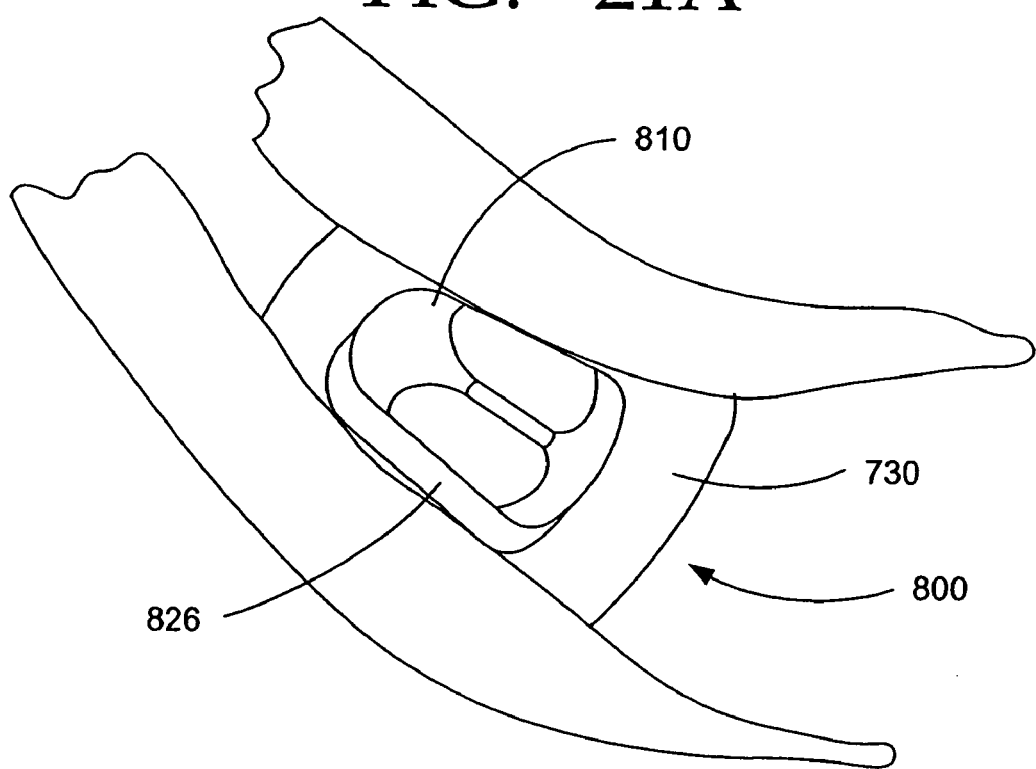
FIG. 21B is an end view of the implant of FIG. 20 showing an expansion portion of the spacer distracted.

As described in greater detail below, the expansion portion 826 is positioned within a channel of the main portion 822, and extends the depth of the spacer 820 along the spinous processes as well as across a substantial portion of the length of the spacer 820 so that the contact surface of one of the spinous processes contacts the expansion portion 826. When unexpanded, the contact surface of the expansion portion 826 should not impede movement of the implant 800 into position between the adjacent spinous processes during surgery. As shown, the contact surface of the expansion portion 826 is substantially aligned with a surface of the main portion 822 so that the expansion portion 826 does not protrude in such a way as to impede positioning of the implant 800 between spinous processes. The expansion portion 826 is separatably connected with the main portion 822 by a stem, a hinge, or some other device. One or more grooves 850 (or other cavities) are disposed between the expansion portion 826 and the main portion 822. When expanded, the grooves 850 are shaped to receive inserts 854. For example, where the inserts 854 are threaded screws, the expanded grooves 850 are shaped as threaded screw holes. However, the grooves 850 do not have a continuous inner surface and when the spacer 820 is unexpanded, the grooves are at least partially collapsed. In the embodiment of FIG. 20, two inserts 854 are associated with the implant 800. Each of the inserts 854 is a threaded screw. In other embodiments, the inserts 854 can be any rigid structure capable of applying a force between the main portion 822 and the expansion portion 826 to urge the main portion 822 and expansion portion 826 apart. For example, the insert 854 can be a pin or a clip. As shown, the spacer 820 includes a pair of threaded grooves 850—one groove 850 formed at each corner where the expansion portion 826 meets the main portion 822. The grooves 850 are counter-sunk to receive a distal end of a corresponding threaded screw 854, thereby allowing the threaded screw 854 to initiate distraction of the expansion portion 826 from the main portion 822. As the threaded screw 854 is seated within the groove 850, the groove expands to accommodate the threaded screw 854. Each groove 850 must expand so that the expansion portion 826 is urged away from the main portion 822. As shown in FIGS. 21A and 21B, the overall height of the spacer 820 between the adjacent spinous process is expanded, distracting the adjacent spinous processes, and/or gripping the contact surface of the spinous process.

Figure 22A:
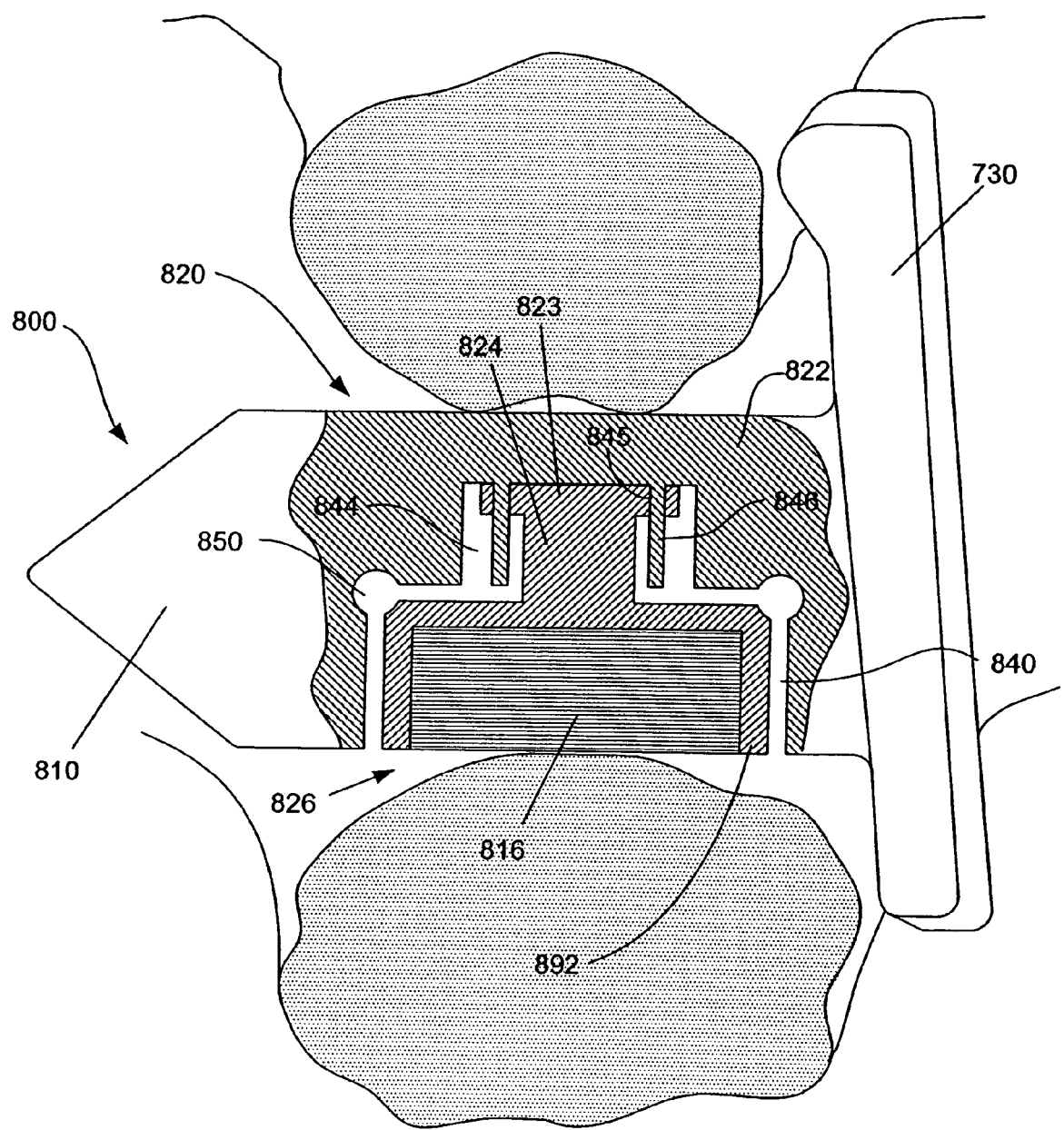
FIG. 22A is a partial cross-sectional posterior view of an embodiment of an implant for use with systems and methods of the present invention positioned between spinous processes, the implant having a spacer including an expansion portion.
Figure 22B:
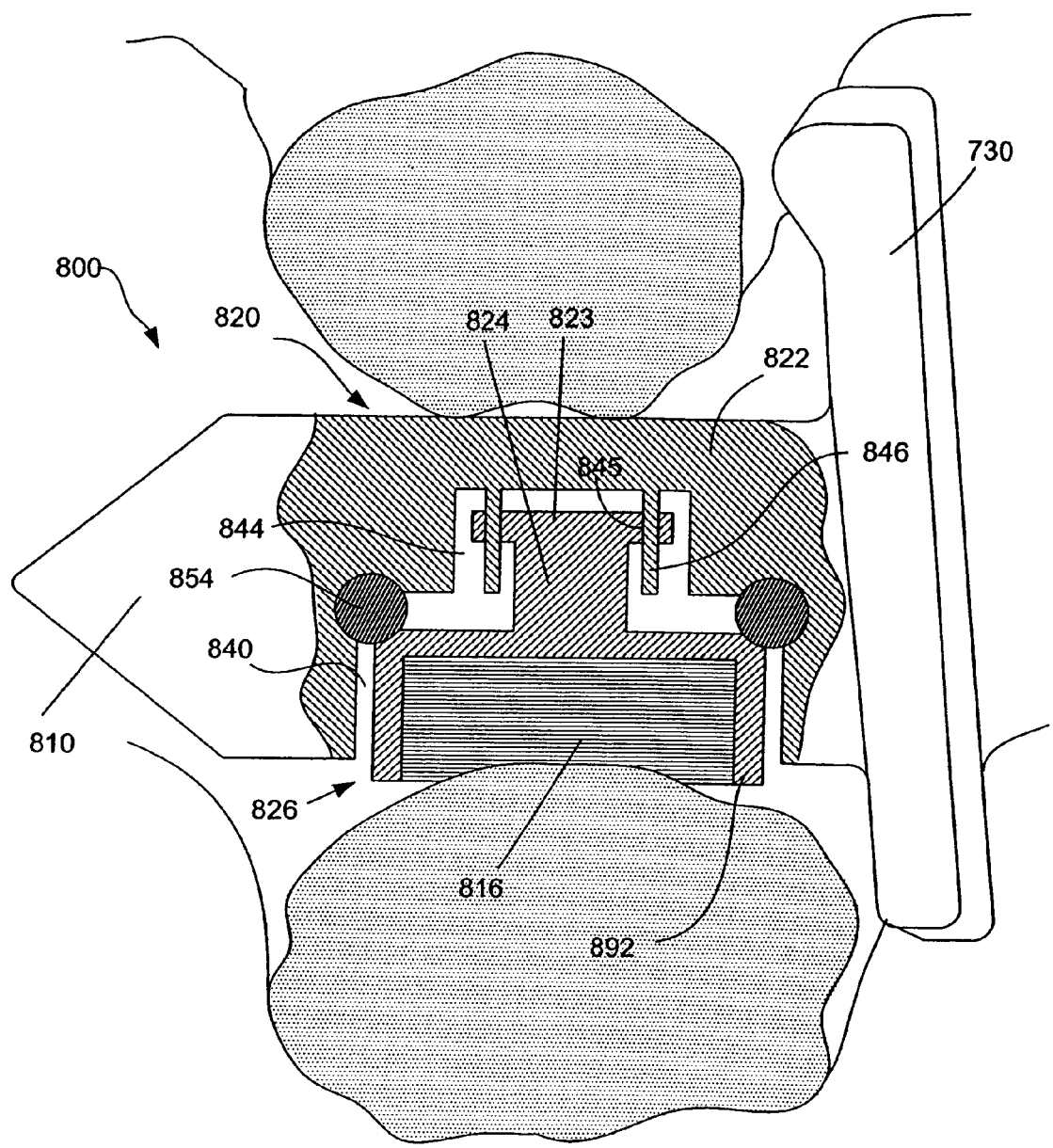
FIG. 22B is a partial cross-sectional posterior view of the implant of FIG. 22A wherein the expansion portion is urged away from a main portion of the spacer.
Figure 22C:
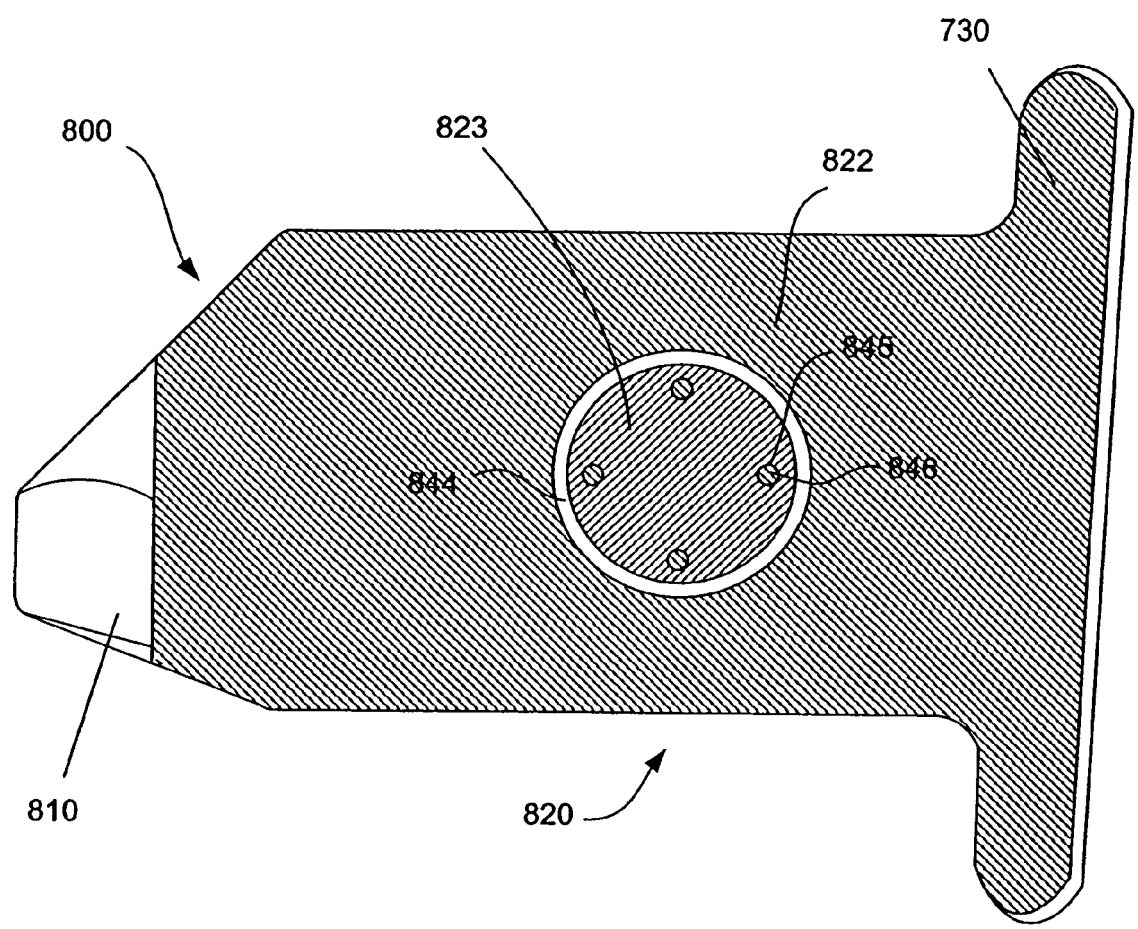
FIG. 22C is a cross-sectional top view of the implant of FIGS. 22A and 22B.
Figure 22D:
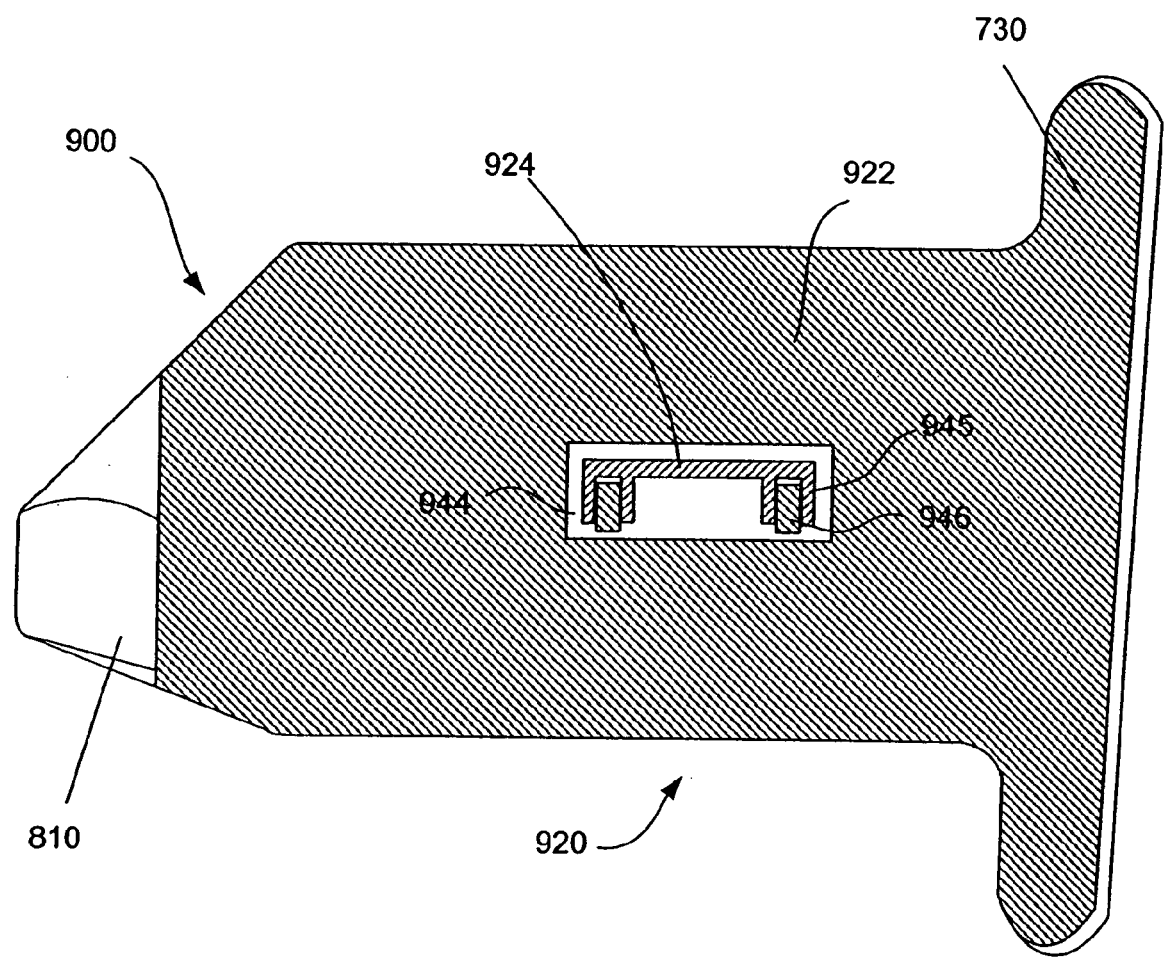
FIG. 22D is a cross-sectional top view of an implant in accordance with an alternative embodiment having tines for cojoining the expansion portion and main portion.

Referring to FIG. 22A, a partial cross-section of an embodiment of an expandable implant 800 in accordance with the present invention is shown. As can be seen, the main portion 822 includes a channel 840 having a bore 844 within which a stem 824 associated or connected with the expanded portion 826 is retained. During implantation, the expansion portion 826 is seated within the main portion 822 by an interference fit between holes 845 within a flange 823 of the stem 824 and a plurality of protrusions 846 of the main portion 822. FIG. 22C is a cross-sectional top view of the implant showing four protrusions 846 disposed within four holes 845 arranged about the flange 823. In other embodiments, the expansion portion 826 and main portion 822 need not be cojoined as shown. For example, as shown in the cross-sectional top view of FIG. 22D, the expansion portion can include a stem 924 having prongs 945 for engaging protrusions 946 of the main portion 922. The prongs 945 are sized so that the protrusions 946 force the prongs 945 apart as the expansion portion 926 is seated within a cavity 944 (in this case, a cavity), creating an interference fit. By using an interference fit to cojoin an expansion portion 826 and a main portion 822, manufacturing can be simplified by reducing the complexity of components. Further, where the expansion portion 826 can be completely separated from the main portion 822, a physician can optionally replace an expansion portion 826 with an expansion portion comprising, for example, a material having a different stiffness, or an expansion portion having a differently shaped contact surface more suitable to a patient's physiology. A physician can have a set of expansion portions, one of which can be selected to suit an individual patient's needs. In this sense, the expansion portion 826 can allow the implant to be customized for a patient.

Referring again to FIG. 22A, the expansion portion 826 can comprise a rigid or semi-rigid shell 892 associated, connected, or integrally formed with the stem 824. A grip 816 can be positioned within the shell 892 and held, for example, by adhesion, an interference fit, or some other mechanism. The grip 816 can be made of a deformable material, such as a polyketone or other thermoformable plastic, or the grip 816 can be made of a more pliant material, such as silicone. Such materials are described in greater detail below. As can be seen, a groove 850 is disposed at each of the corners of the shell 892. The grooves 850 are partially collapsed. Referring to FIG. 22B, as inserts 854 are forced into the grooves 850, force is applied to the shell 892. The expansion force overcomes the frictional resistance of the interference fit and the expansion portion 826 is urged away from the main portion 822. Where the grip 816 comprises a pliant material, the grip 816 at least partially reshapes as it contacts the corresponding spinous process and grips the spinous process, resisting relative movement between the implant 800 and the adjacent spinous processes. During expansion, the spinous processes can also be further distracted.

Figure 23A:
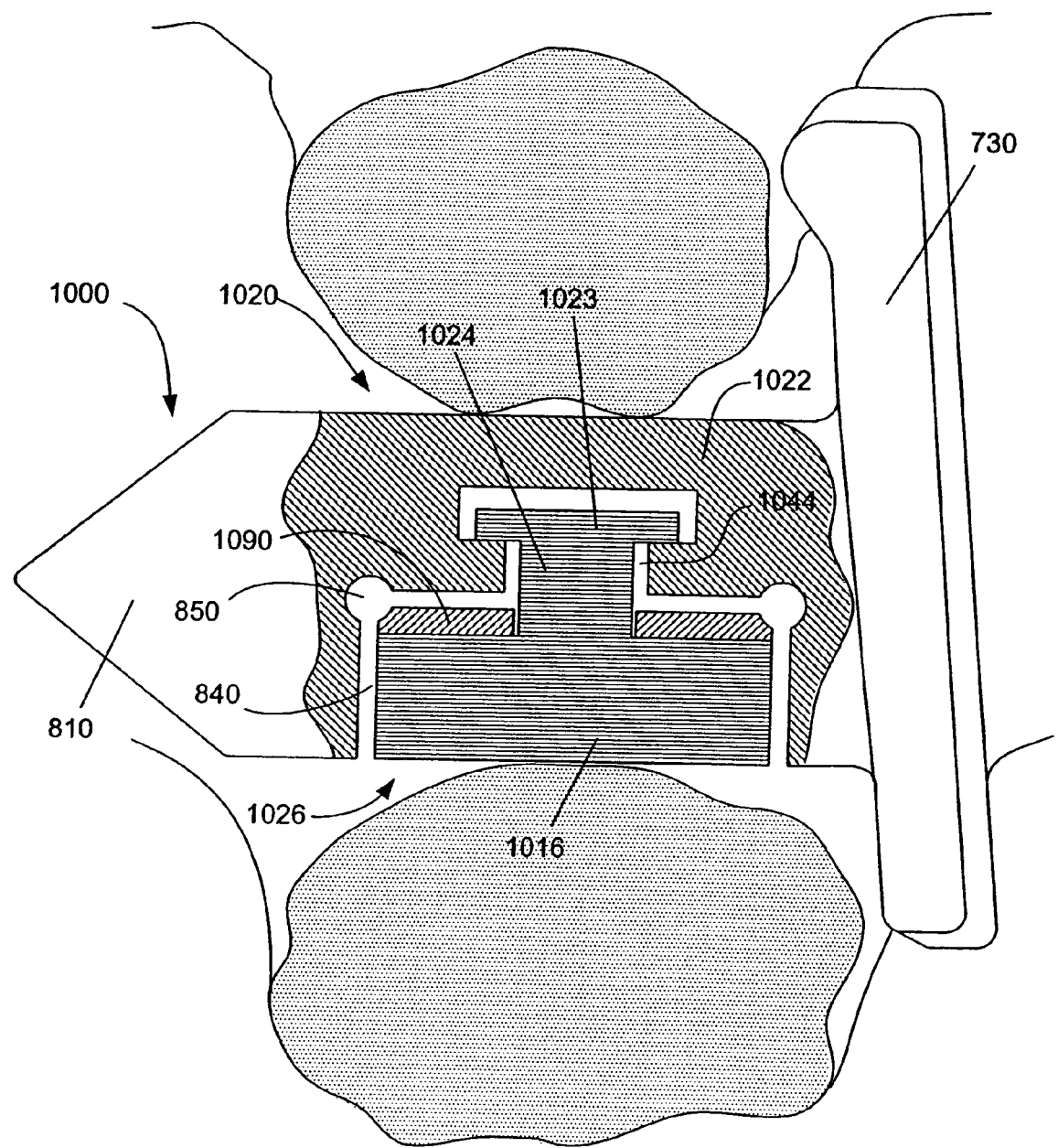
FIG. 23A is a partial cross-sectional posterior view of an alternative embodiment of an implant for use with systems and methods of the present invention positioned between spinous processes, the implant having a spacer including an expansion portion having a pliant stem.
Figure 23B:
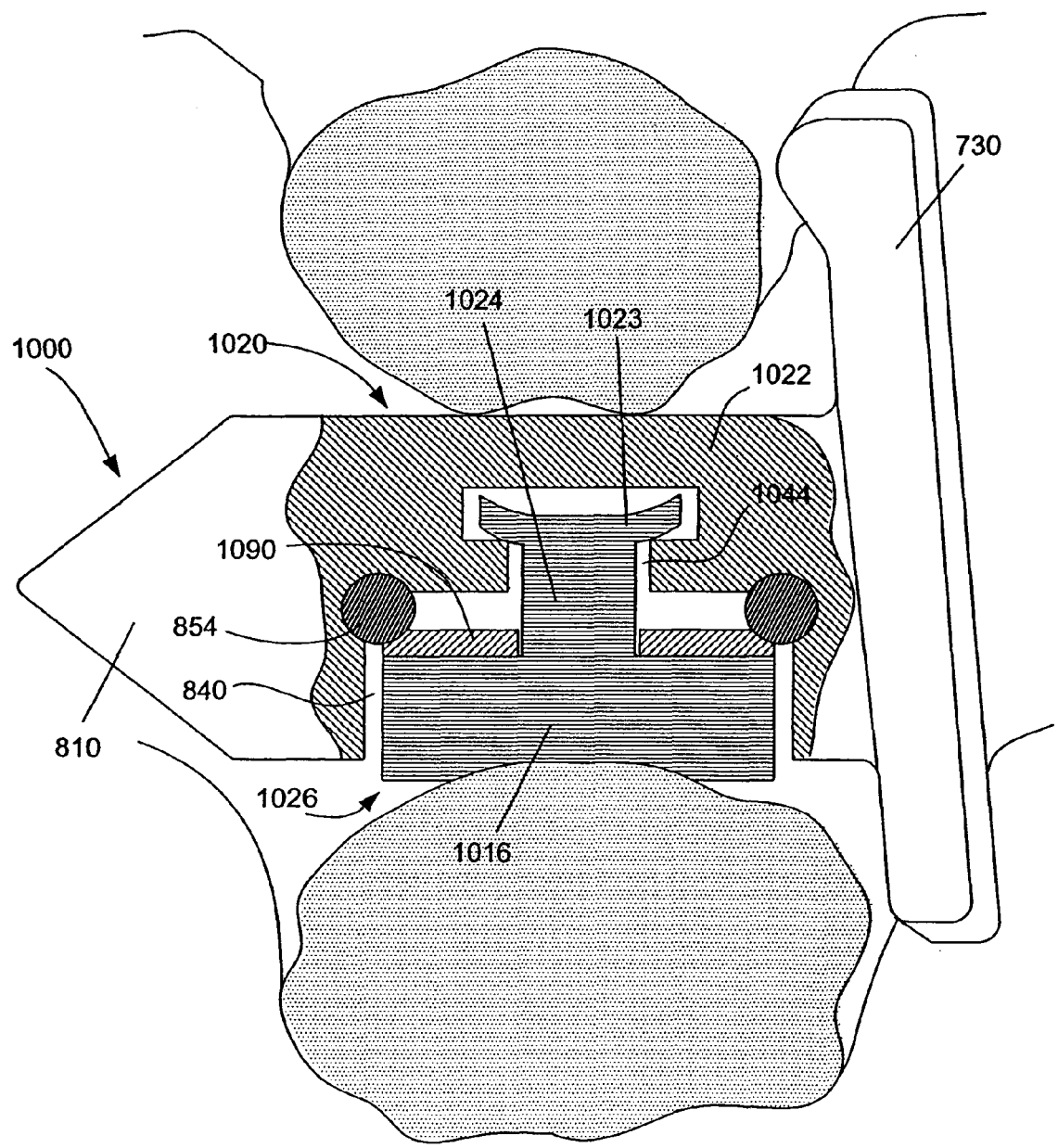
FIG. 23B is a partial cross-sectional posterior view of the implant of FIG. 23A wherein the expansion portion is urged away from a main portion of the spacer.

FIGS. 23A and 23B are partial cross-sections of an alternative embodiment of an expandable implant 1000 in accordance with the present invention. The main portion 1022 includes a channel 840 having a bore 1044. The bore 1044 is necked so that a portion of the bore 1044 narrows in diameter near the opening to the channel 840. The narrow portion can be used to retain a stem 1024 of an expansion portion 1026. The expansion portion 1026 in such embodiments can comprise a rigid (or semi-rigid) ring 1090 around which the stem 1024 and a grip 1016 is formed. The ring 1090 transfers a force applied by a pair of inserts 854 to the grip 1016 of the expansion portion 1026 so that the expansion portion 1026 distracts away from the inserts 854 rather than simply deforms around the inserts 854 (as may happen where the grip 1016 is made from a pliant material). The stem 1024 is positioned within the bore 1044, and is shaped so that a distal end of the stem 1024 includes a diameter wider than a diameter of the narrow portion of the bore 1044. When an expansion force is not applied, the stem 1024 retains the expansion portion 1026 within the main portion 1022. As above, a groove 850 is disposed on each side of the stem 1024 between the ring 1090 and the main portion 1022. The grooves 850 are partially collapsed. As the inserts 854 are mated and seated within the grooves 850, the ring 1090 is forced away from the inserts 854 and consequently away from the main portion 1022. The ring 1090 applies a force to the grip 1016 that causes the stem 1024 to be flexed, as shown in FIG. 23B, and the grip 1016 at least partially reshapes around the contact surface of the corresponding spinous process. The expansion portion 1026 grips the spinous process, resisting relative movement between the implant 1000 and the adjacent spinous processes. In such embodiments, the grip 1016 can be made of a pliant material to permit flexing, as described above and in further detail below.

Figure 24A:
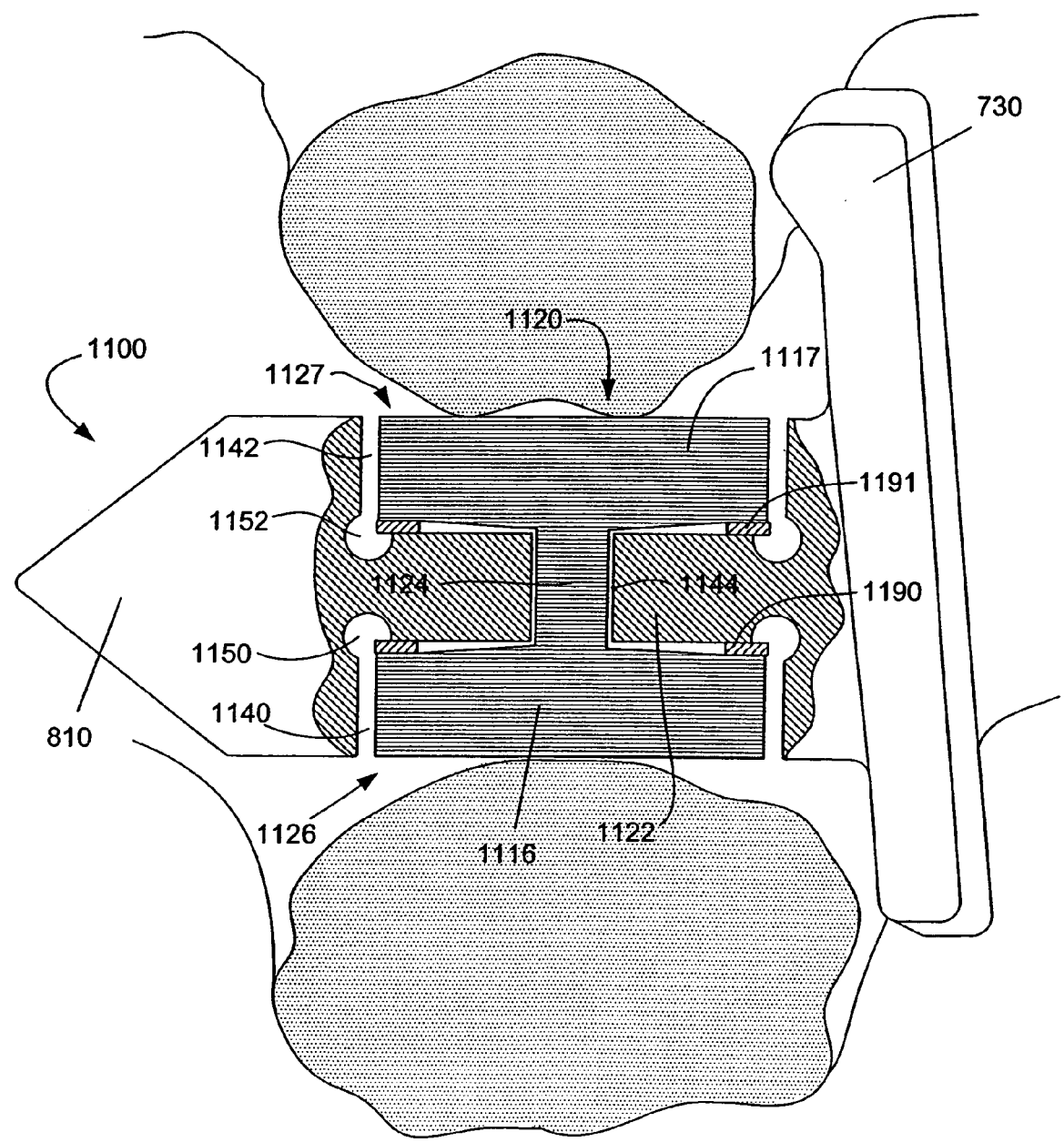
FIG. 24A is a partial cross-sectional posterior view of still another embodiment of an implant for use with systems and methods of the present invention positioned between spinous processes, the implant having a spacer including an expansion portion.
Figure 24B:
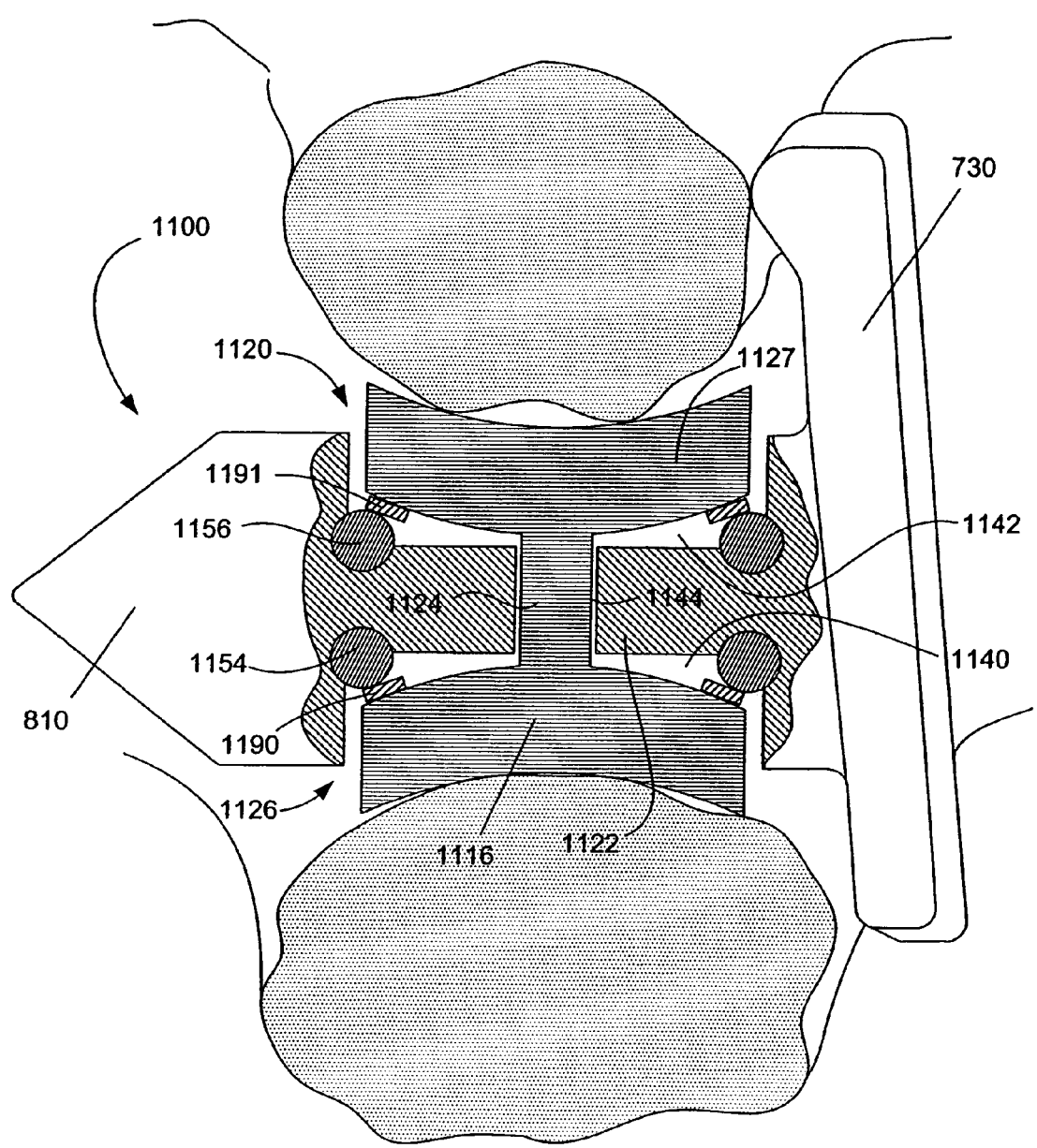
FIG. 24B is a partial cross-sectional posterior view of the implant of FIG. 24A wherein the expansion portion is urged away from a main portion of the spacer.

FIGS. 24A and 24B are partial cross-sections of still another embodiment of an expandable implant 1100 in accordance with the present invention. Such an embodiment includes two expansion portions 1126,1127, each expansion portion 1126,1127 being arranged to contact a respective spinous process. The expansion portions 1126,1127 each comprise a ring 1190,1191 and a grip 1116,1117. The ring 1190,1191 can be similar to the ring 1090 described with respect to FIGS. 23A and 23B, or the ring can be thinner to more easily flex (as shown in FIG. 24B). A main portion 1122 of the spacer 1120 includes two channels 1140,1142 formed within the spacer 1120 and a bore 1144 joining the channels 1140,1142. The expansion portions 1126,1127 are cojoined at the bore 1144 by a neck 1124 so that when no expansion force is applied, the expansion portions 1126,1127 have a contact surface substantially flush with an outer surface of the main portion 1122. A groove 1150,1152 or other cavity is positioned along each of the corners of the expansion portions 1126,1127, within the main portion 1122. In other embodiments, more or fewer grooves can be formed and arranged to forcibly distract the expansion portions 1126,1127 from the main portion 1122. As shown in FIG. 24B, as the inserts 1154,1156 are mated and seated within the grooves 1150, 1152, the ring 1190,1191 of each expansion portion 1126, 1127 is forced away from the inserts 1154,1156 and away from the main portion 1122. The expansion force causes the cojoined expansion portions 1126,1127 apart, and a neck 1124 cojoining the expansion portions 1126,1127 is stretched and thins. The grip 1116,1117 of the expansion portions 1126,1127 can at least partially reshape themselves to conform to the respective spinous processes, and can grip the spinous processes, preventing shifting of the implant 1100 relative to the spinous processes. As in the previous embodiment, the grip 1116,1117 can be made of a pliant material, as described above and in further detail below.

Figure 25A:
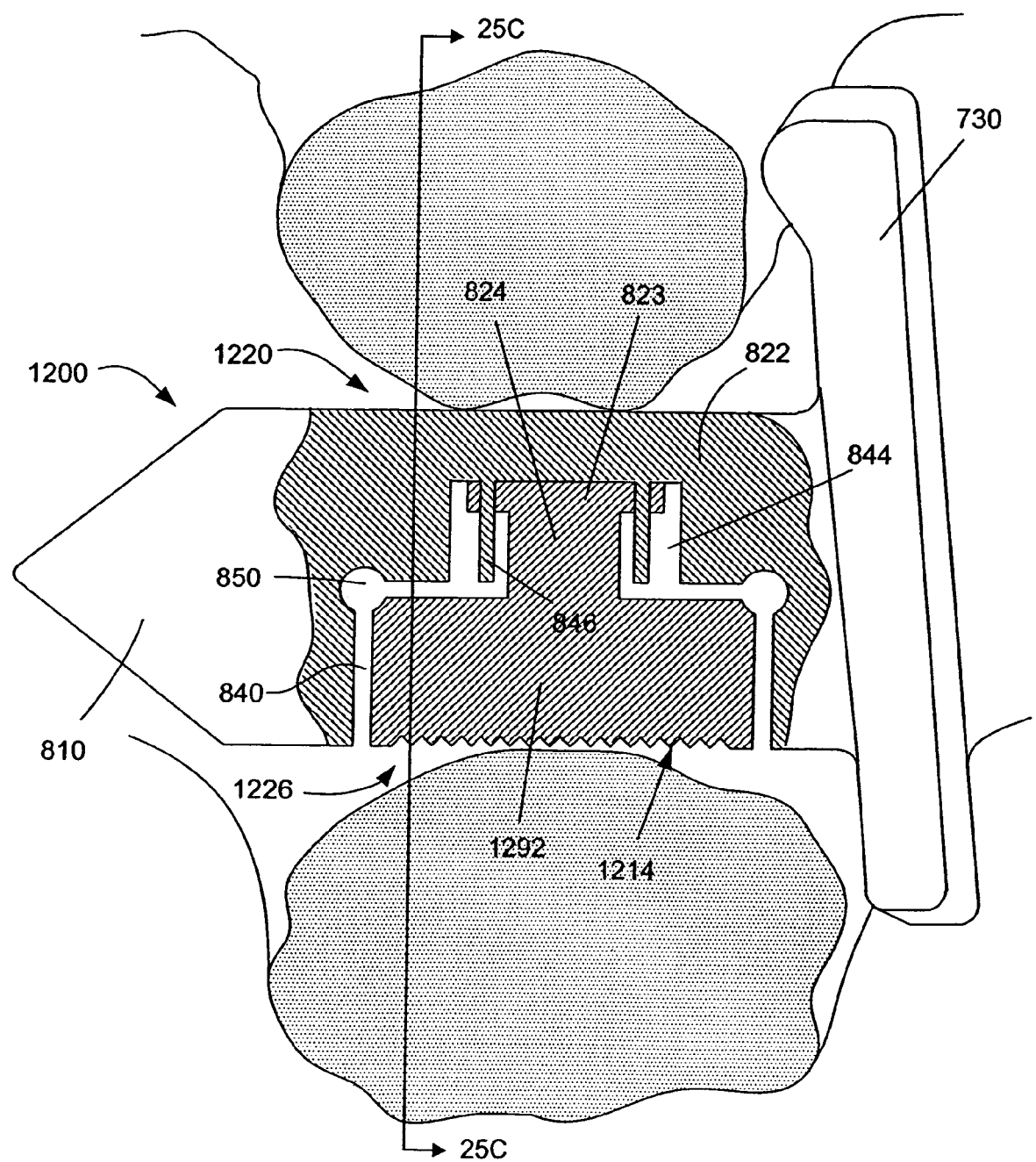
FIG. 25A is a partial cross-sectional posterior view of still another embodiment of an implant for use with systems and methods of the present invention positioned between spinous processes, the implant having a spacer including an expansion portion.
Figure 25B:
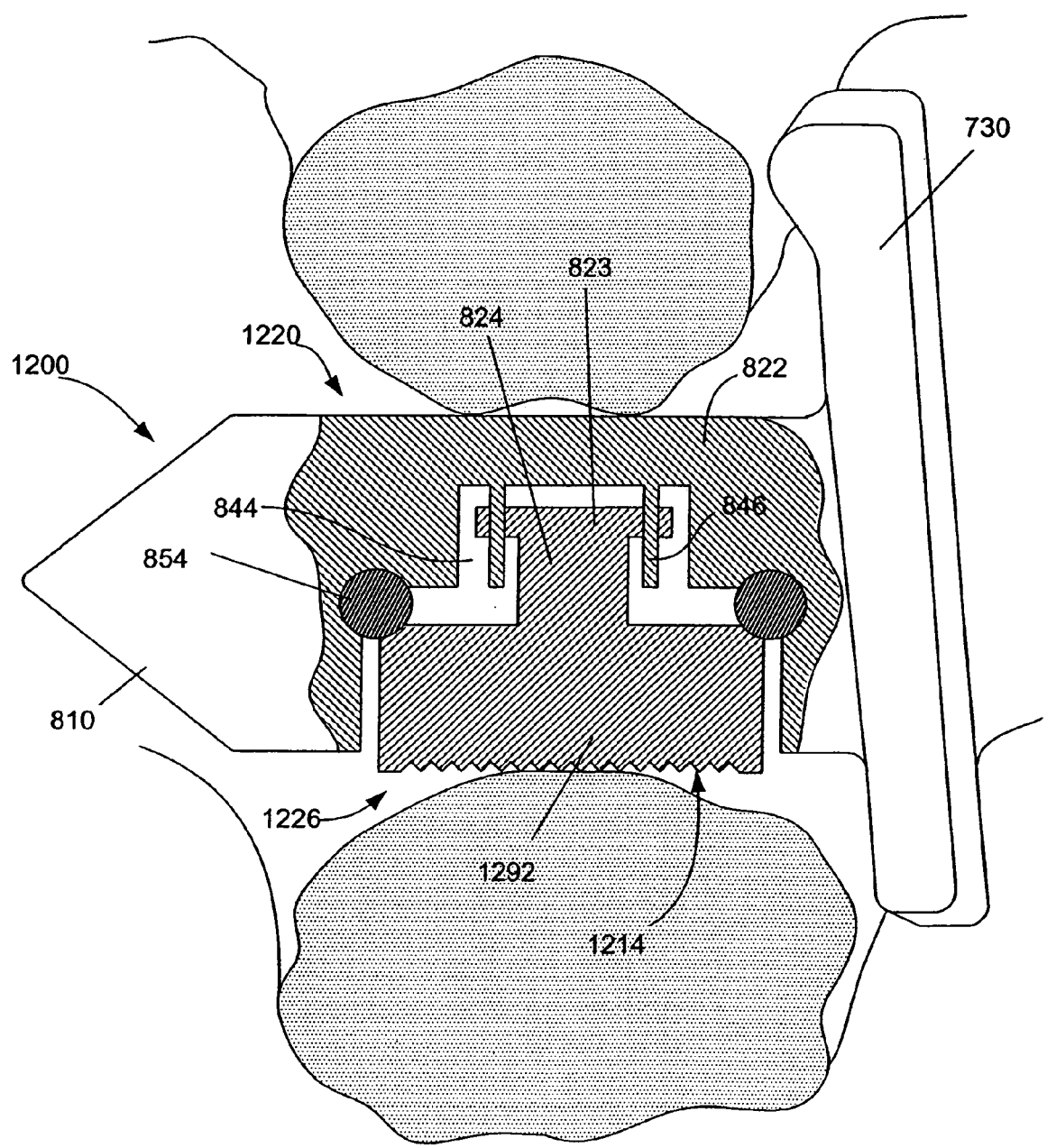
FIG. 25B is a partial cross-sectional posterior view of the implant of FIG. 25A showing an expansion portion of the spacer urged away from a main portion of the spacer.
Figure 25C:
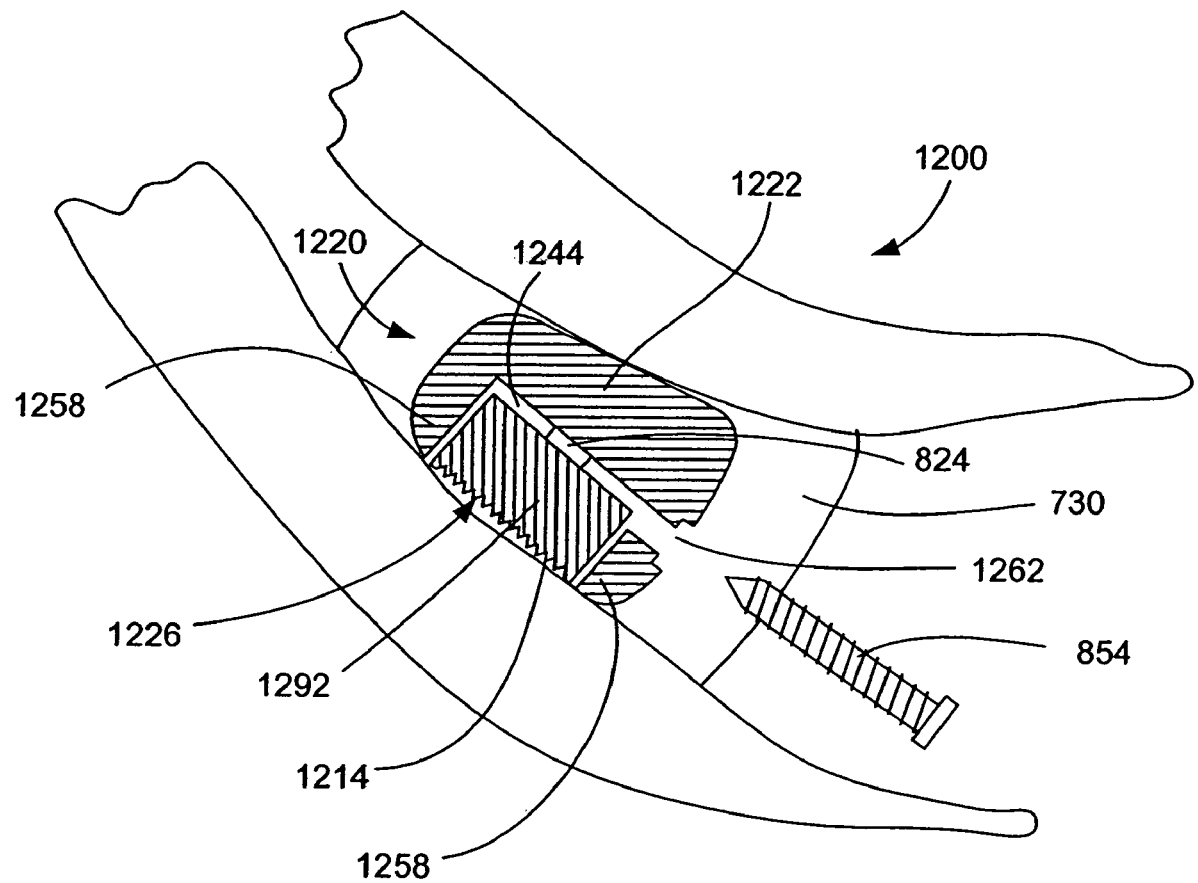
FIG. 25C is a cross-sectional end view of the implant of FIG. 25A including walls for slidably contacting adjacent spinous processes.

FIGS. 25A and 25B are partial cross-sections of a still further embodiment of an expandable implant 1200 in accordance with the present invention. The implant 1200 resembles the implant of FIGS. 22A-22D in that the main portion 822 includes a channel 840 and a bore 844 formed within the channel 840. One or more protrusions 846 extend from within the bore 844 for forming an interference fit with a stem 824 of the expansion portion 1226, as described above. The expansion portion 1226 can comprise a rigid or semi-rigid structure 1292 associated, connected, or integrally formed with the stem 824, and having a contact surface including a plurality of teeth 1214. As above, the main portion 822 includes grooves 850. As inserts 854 are positioned within the grooves 850, the teeth 1214 of the expansion portion 1226 can be embedded into, and/or can contactingly engage, a corresponding spinous process. The teeth 1214 grab the surface and prevent relative shifting between the implant 1200 and the spinous processes. As shown in FIG. 25C, it can be desirable that a main portion 1222 include a cavity 1240 rather than a channel 840, with the main portion 1222 including walls 1258 and with the expansion portion 1226 being slightly recessed within the cavity 1240. In such an arrangement, surfaces of the walls 1258 slide along the contact surface of both spinous processes, preventing impedance of movement by teeth 1214 of the expansion portion 1226. Once the implant 1200 is positioned, the expansion portion 1226 can be urged away from the main portion 1222. The walls 1258 of the main portion 1222 can include holes 1262 through which an insert 854 can pass to mate and seat within a corresponding groove 850. When the inserts 854 are fully seated, the expansion portion 1226 can extend beyond the walls 1258 of the main portion 1222, embedding (or contactingly engaging) the teeth 1214 of the expansion portion 1226 within the corresponding spinous process, thereby preventing shifting of the implant 1200 relative to the spinous processes.

Figure 26A:
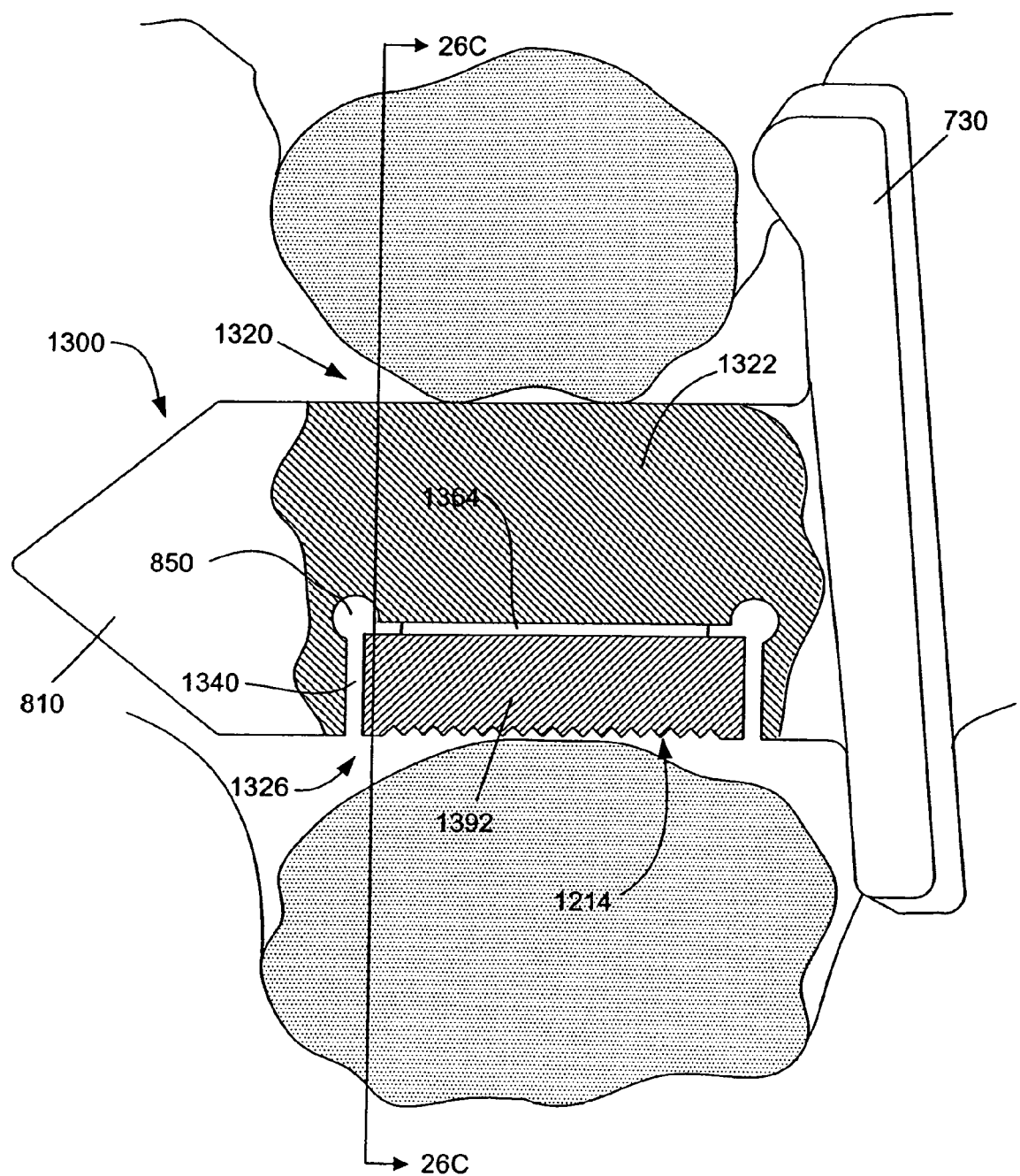
FIG. 26A is a partial cross-sectional posterior view of still another embodiment of an implant for use with systems and methods of the present invention positioned between spinous processes, the implant having a spacer including an expansion portion.
Figure 26B:
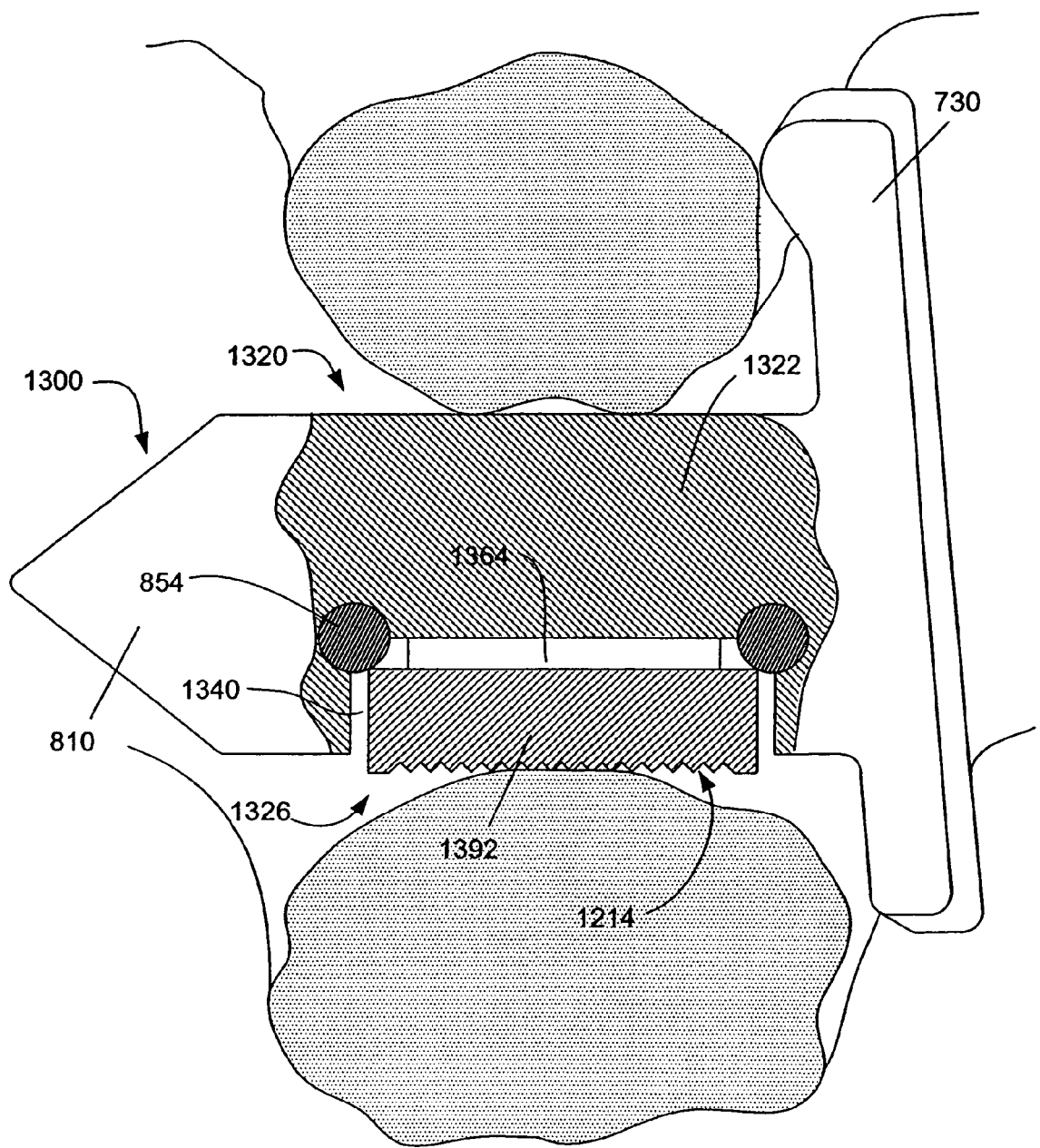
FIG. 26B is a partial cross-sectional posterior view of the implant of FIG. 26A wherein the expansion portion is urged away from a main portion of the spacer.
Figure 26C:
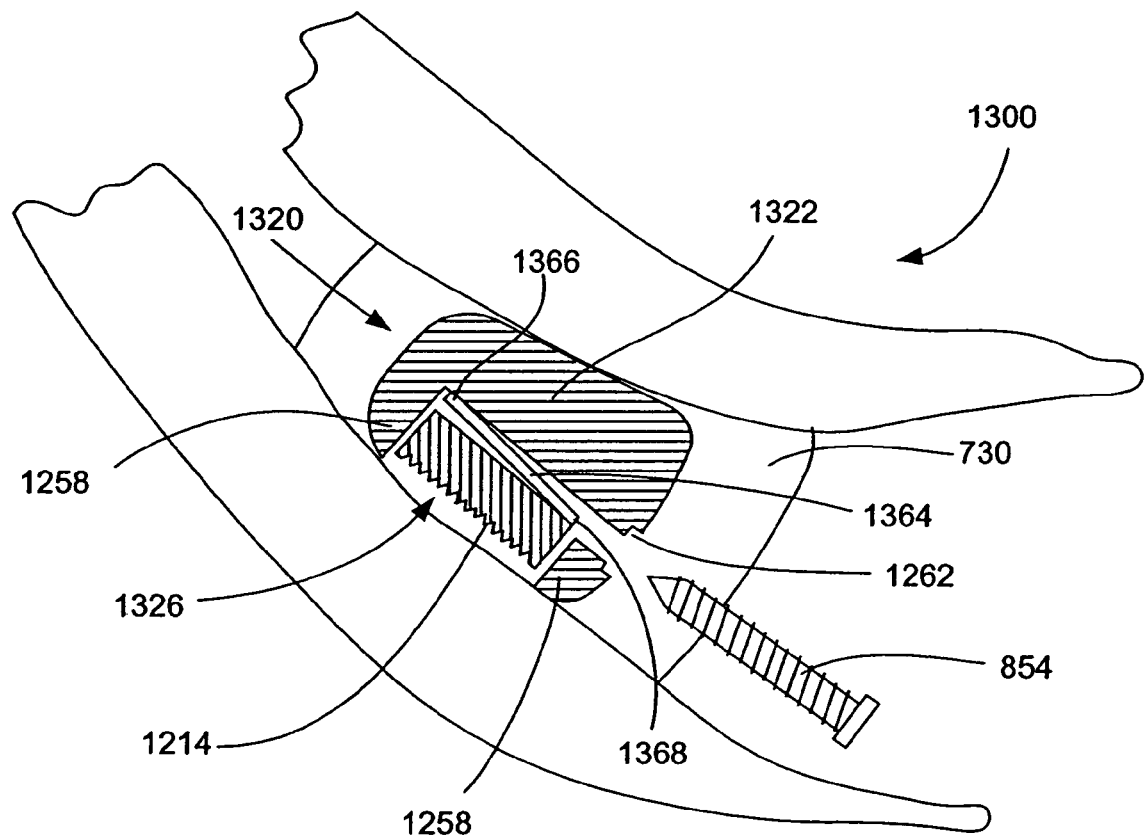
FIG. 26C is a cross-sectional end view of the implant of FIG. 26A.

FIGS. 26A-26C are partial cross-sections of still another embodiment of an expandable implant 1300 in accordance with the present invention. A main portion 1322 of the spacer 1320 can include a cavity 1340 within which is disposed an expansion portion 1326. The expansion portion 1326 can comprise a rigid or semi-rigid structure 1392 connected with the main portion 1322 by a hinge 1364. The contact surface of the expansion portion 1326 includes a plurality of teeth 1214. As above, the main portion 1322 includes grooves 850. As inserts 854 are positioned within the grooves 850, an expansion force urges the expansion portion 1326 away from the main portion 1322. The hinge 1364 can bend at two hinge points 1366,1368 to yield to the expansion force, as shown in FIG. 26C. As the expansion portion 1326 is urged away from the main protion 1322, the teeth 1214 of the expansion portion 1326 can be embedded into, or can contactingly engage, a corresponding spinous process. The teeth 1214 grab the contact surface to prevent relative shifting between the implant 1300 and the spinous processes. As with the previously described embodiment, the main portion 1322 can include a cavity 1340 rather than a channel, with the main portion 1322 including walls 1258 and with the expansion portion 1326 being slightly recessed within the cavity 1340, thereby preventing the teeth 1214 from possibly damaging the contact surface of the respective spinous process or associated tissues during implantation. An embodiment of a hinge 1364 can be seen in profile in FIG. 26C. The hinge 1364 as shown include two hinge points 1366,1368 but in other embodiments can include more hinge points, similar to an accordion or bellows. Although the hinge 1364 as shown and described is used with expansion portions 1326 including teeth 1214, in other embodiments, a hinge 1364 can alternatively be used with an expansion portion 826 including a grip 816, as described in previous embodiments. While stem arrangements and hinge arrangements have been described in detail, one of ordinary skill in the art will appreciate that other arrangements to urge a spacer to expand can be employed as well.

Figure 27A:
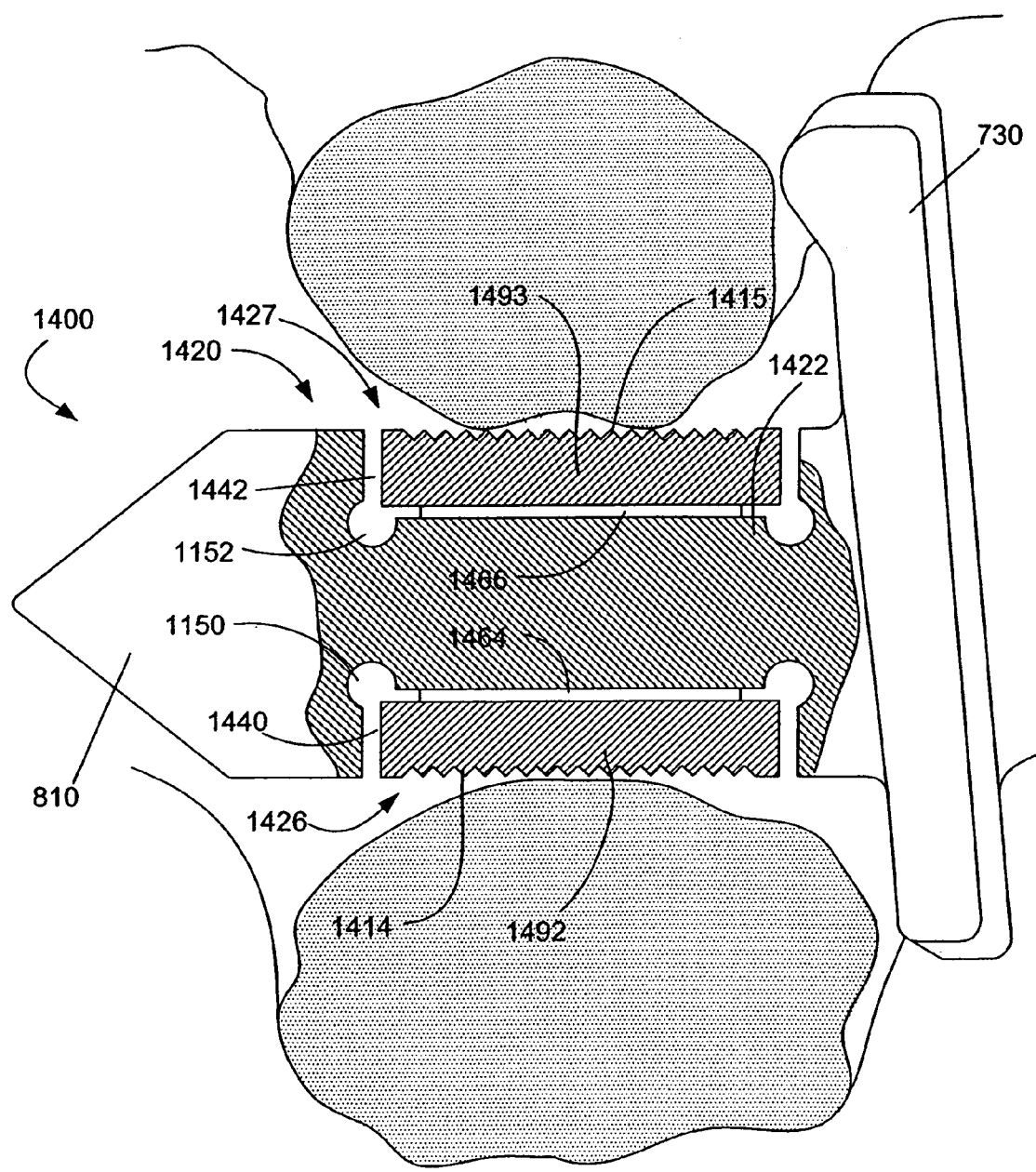
FIG. 27A is a partial cross-sectional posterior view of still another embodiment of an implant for use with systems and methods of the present invention positioned between spinous processes, the implant having a spacer including an expansion portion.
Figure 27B:
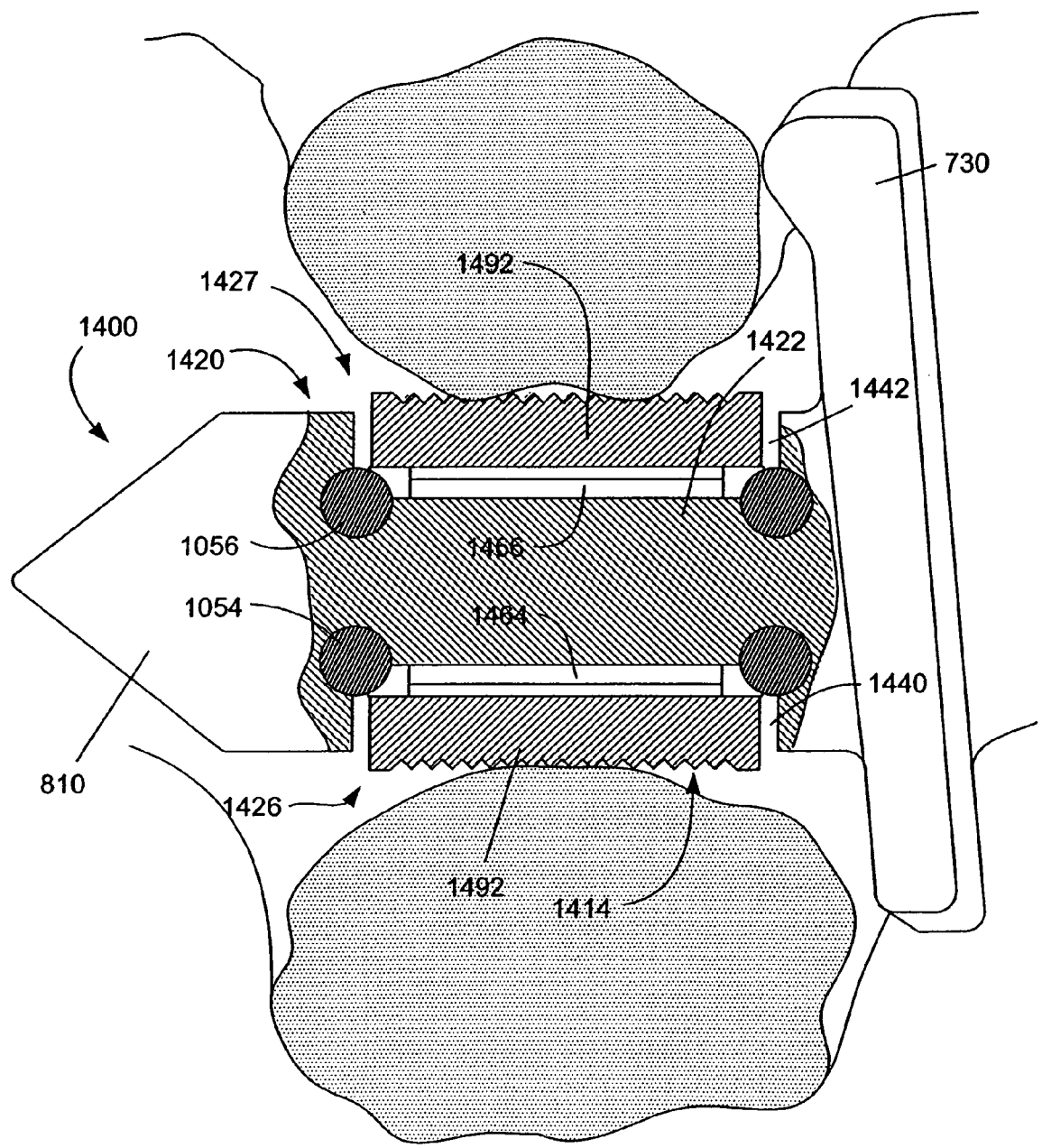
FIG. 27B is a partial cross-sectional posterior view of the implant of FIG. 27A wherein the expansion portion is urged away from a main portion of the spacer.

FIGS. 27A and 27B are cross-sections of a still further embodiment of an expandable implant 1400 in accordance with the present invention. A main portion 1422 of the spacer 1420 includes a first channel 1440 and a second channel 1441 within which are disposed a first expansion portion 1426 and a second expansion portion 1427, respectively. As in the previous embodiment, the expansion portion 1426,1427 can comprise a rigid or semi-rigid structure 1492,1493 connected with the main portion 1422 by a hinge 1464,1465. As in the previous embodiments, the contact surface of the first and second expansion portions 1426,1427 include a plurality of teeth 1414,1415. Two grooves 1150 are positioned between the first expansion 1426 and the main portion 1422 and two grooves 1152 are positioned between the second expansion portion 1427 and the main portion 1422. As inserts 1154,1156 are positioned within the grooves, the teeth 1414,1415 of the expansion portion 1426,1427 engage a corresponding spinous process. The teeth 1414,1415 provide a grip for preventing relative shifting between the implant and the spinous processes. As with the previously described embodiments, the main portion 1422 can include a cavity rather than a channel, with the main portion 1422 including walls and with the expansion portions 1426,1427 being slightly recessed within the cavity, thereby preventing the teeth 1414,1415 from possibly damaging the contact surface of the respective spinous process or associated tissues during implantation.

Figure 28:
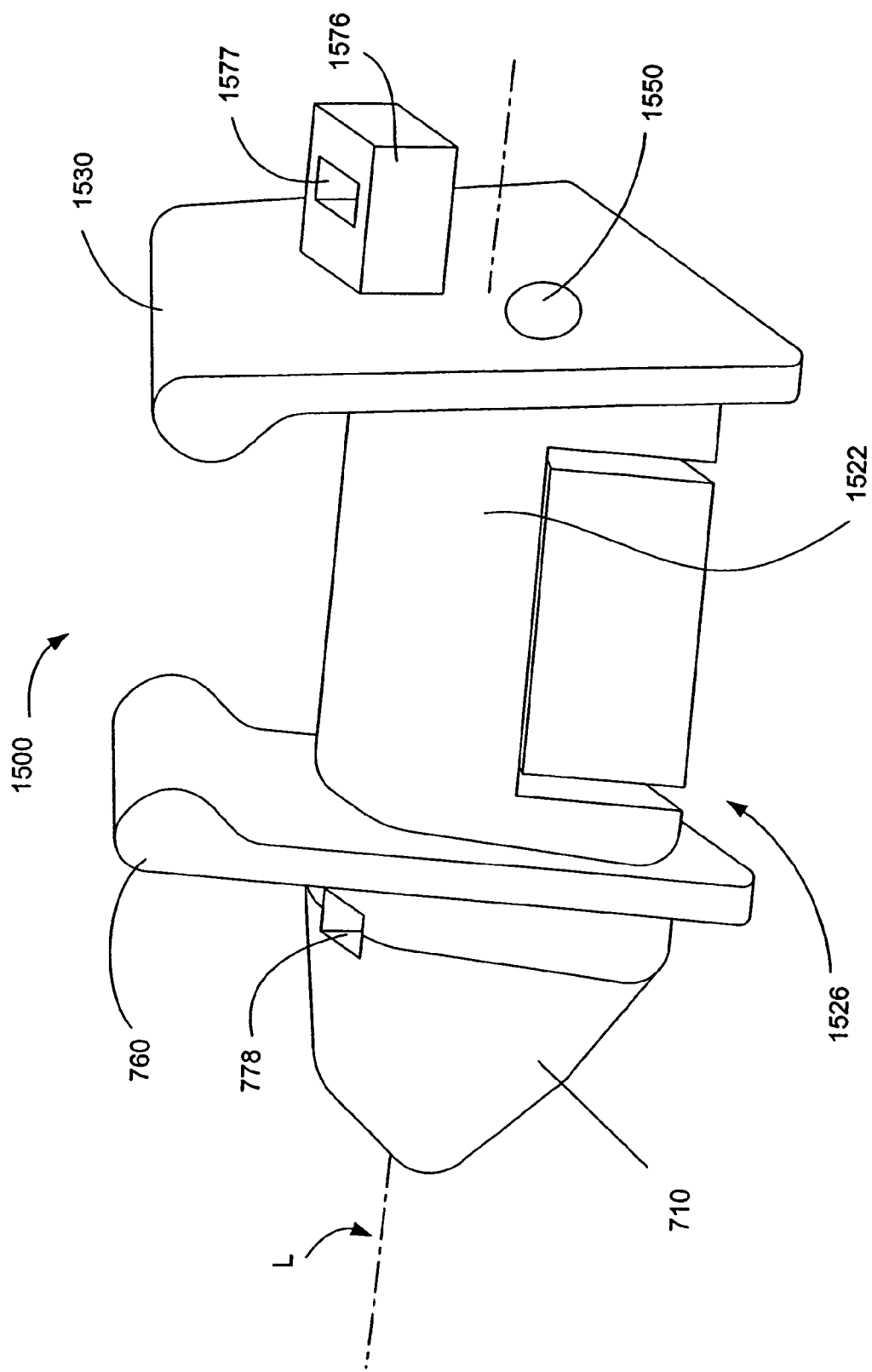
FIG. 28 is a perspective view of a still further embodiment of an implant for use with systems and methods of the present invention, wherein a cavity for receiving an insert is accessible through a wing.

While the embodiments described above include inserts positioned within grooves using a posterior approach, implants in accordance with the present invention should not be construed as being limited to such schemes. For example, as shown in FIG. 28, one or more grooves 1550 can be formed parallel to the longitudinal axis of the implant 1500, rather than perpendicular to the longitudinal axis L. An insert 1554 can be positioned to distract the expansion portion 1526 using a lateral approach, that is to say an approach that is about perpendicular to a poster-to-anterior direction. In such embodiments, a bore can be formed within the first wing 1530 having a diameter to accommodate the diameter of the insert 1554.

As shown in the perspective view of FIG. 28, implants in accordance with embodiments of FIGS. 22-27 can further include a binder to limit or block flexion of the adjacent vertebrae from which the spinous processes extend. In such embodiments the distraction guide 710 and/or the spacer 1520 can include a slot 778 through which the binder can be positioned. An anchor 1576 can extend from a proximal end of the implant 1500, the anchor 1576 including a slot 1577 for receiving the binder. The anchor 1576 of FIG. 28 is offset so as not to impede access to the groove 1550 by an insert 1554.

It is to be understood that the various features of the various embodiments can be combined with other embodiments of the invention and be within the spirit and scope of the invention. Thus, for example only, the embodiment of FIG. 18 can have truncated wings as depicted in previous embodiments.

Materials for use in Implants of the Present Invention

In some embodiments, the implant (except for the grip, where included) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryl ester ketones which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Referring now to FIGS. 22A-24B, various embodiments of an expansion portion of a spacer include a grip. FIGS. 22A and 22B include a shell associated, connected or integrally formed with a stem. As shown, the shell can provide a frame for retaining a grip, or a plate to which the grip can be adhesively, or otherwise attached. Likewise, FIGS. 23A-24B include rings surrounding a stem comprising a pliant material, and distributing a distraction force along the pliant material. The shell and rings can be fabricated from similar materials as described above for the interspinous implant. It is within the scope of the invention that the shell and rings can comprise other shapes, as well. The grip can be made of a pliant material, or in such embodiments where flexing is not required (e.g., FIGS. 22A-22D), the grip can alternatively be made of a flexible or deformable material, such as medical grade biocompatible polymers, copolymers, blends, and composites of polymers. Where the grip is made from a flexible or deformable material, the shell and/or ring can be made from a rigid material, such as a medical grade metal. Where the grip is made from a pliant material, the shell and/or ring can be made from a rigid material, or alternatively from a flexible or deformable material.

The pliant material can be selected to at least partially flex and/or deform when a tensile stress and/or compressive stress is applied to the pliant material. In an embodiment, the pliant material can comprise silicone. It is within the scope of the present invention to manufacture the pliant material from other biologically acceptable, pliant material such as another polymer. For example, the pliant material can comprise urethane-coated silicone and/or urethane co-formed with silicone so that the urethane will not be attacked by the body, or another ultra-high molecular weight polymer. Another preferred material is polycarbonate-urethane, a thermoplastic elastomer formed as the reaction product of a hydroxl terminated polycarbonate, an aromatic diisocyanate, and a low molecular weight glycol used as a chain extender. A preferred polycarbonate glycol intermediate, poly (1,6-hexyl 1,2-ethyl carbonate) diol, PHECD, is the condensation product of 1,6-hexanediol with cyclic ethylene carbonate. The polycarbonate macro-glycol is reacted with aromatic isocyanate, 4,4'-methylene bisphenyl diisocyanate (MDI), and chain extended with 1,4-butanediol. This material is preferable used at a hardness of 55 durometer. This material, as well as the other materials, can be used in the other embodiments of the invention.

The pliant material can further include a graduated stiffness to help gradually distribute the load when distraction of the shell or ring places a force upon the pliant material. For example, the hardness of the silicone can be at its lowest where the silicone contacts the spinous process, and the hardness of the silicone can be at its highest where the pliant material contacts the shell or ring.

Figure 29:
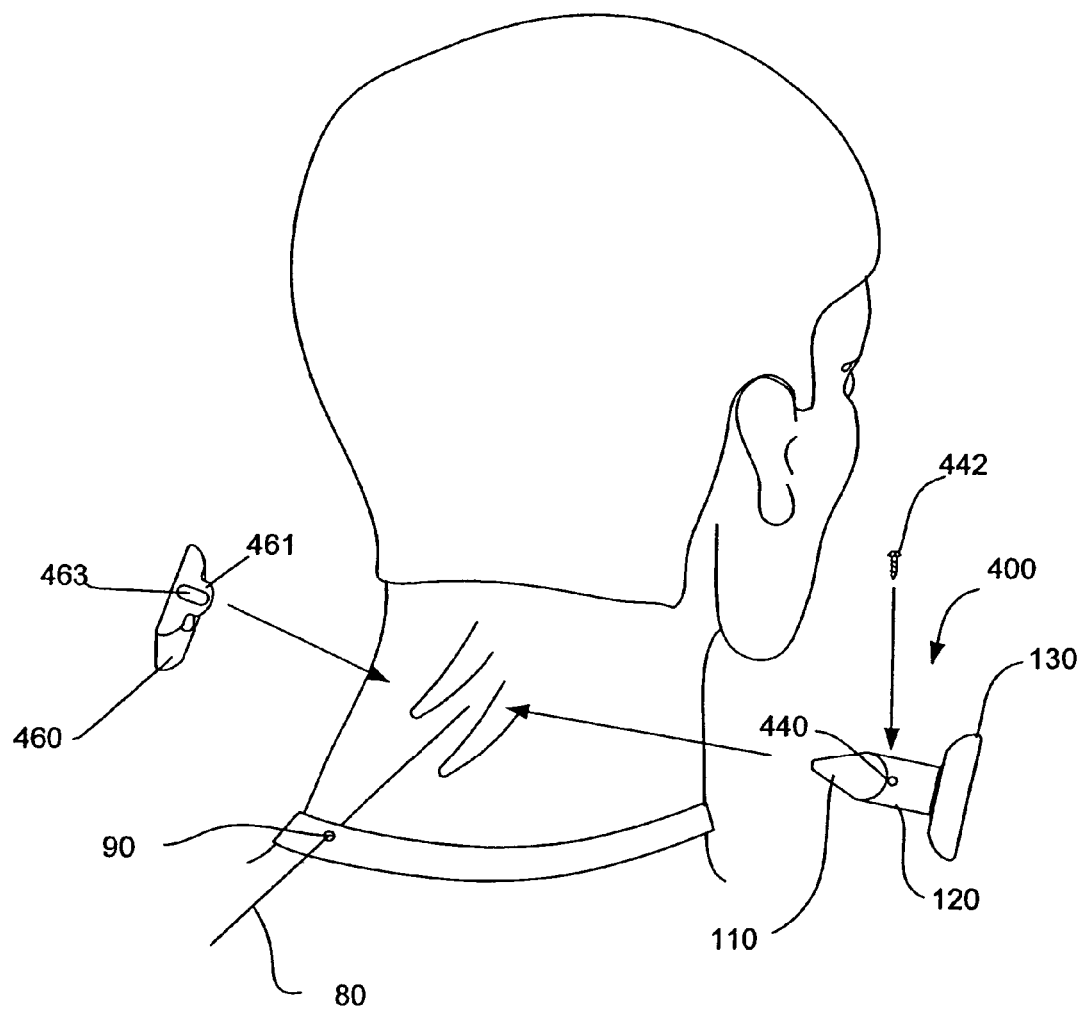
FIG. 29 illustrates an embodiment of a method for implanting an interspinous implant in accordance with the present invention.

It is to be understood that embodiments in accordance with the present invention can be constructed without a pliant material. It is also to be understood that the embodiments in accordance with the present invention can have other dimensions Methods for Implanting Interspinous Implants A minimally invasive surgical method for implanting an implant 400 in the cervical spine is disclosed and taught herein. In this method, as shown in FIG. 29, preferably a guide wire 80 is inserted through a placement network or guide 90 into the neck of the implant recipient. The guide wire 80 is used to locate where the implant is to be placed relative to the cervical spine, including the spinous processes. Once the guide wire 80 is positioned with the aid of imaging techniques, an incision is made on the side of the neck so that an implant in accordance with an embodiment of the present invention, can be positioned in the neck thorough an incision and along a line that is about perpendicular to the guide wire 80 and directed at the end of the guide wire 80. In one embodiment, the implant can be a sized implant 400 (i.e., having a body that is not distractable), such as described above in FIGS. 1-17 and including a distraction guide 110, a spacer 120, and a first wing 130. The implant 400 is inserted into the neck of the patient. Preferably during insertion, the distraction guide 110 pierces or separates the tissue without severing the tissue.

Once the implant 400 is satisfactorily positioned, a second wing 460 can be optionally inserted along a line that is generally colinear with the line over which the implant 400 is inserted but from the opposite side of the neck. The anatomy of the neck is such that it is most convenient and minimally invasive to enter the neck from the side with respect to the implant 400 and the second wing 460. The second wing 460 is mated to the implant and in this particular embodiment, the second wing 460 is attached to the implant 400 by the use of a fastener, for example by a screw 442. Where a screw is used, the screw 442 can be positioned using a screw driving mechanism that is directed along a posterior to anterior line somewhat parallel to the guide wire 80. This posterior to anterior line aids the physician in viewing and securing the second wing 460 to the implant. The second wing 460 is positioned so that a bore 463 formed in a lip 461 of the second wing 460 is aligned with a bore 440 of the implant 400, as described above. The screw 442 is positioned within both bores and secured, at least, to the bore 440 of the implant 400. In other embodiments, the second wing can be interference fit with the implant, as described above, or fastened using some other mechanism, such as a flexible hinge and protrusion.

Figure 30:
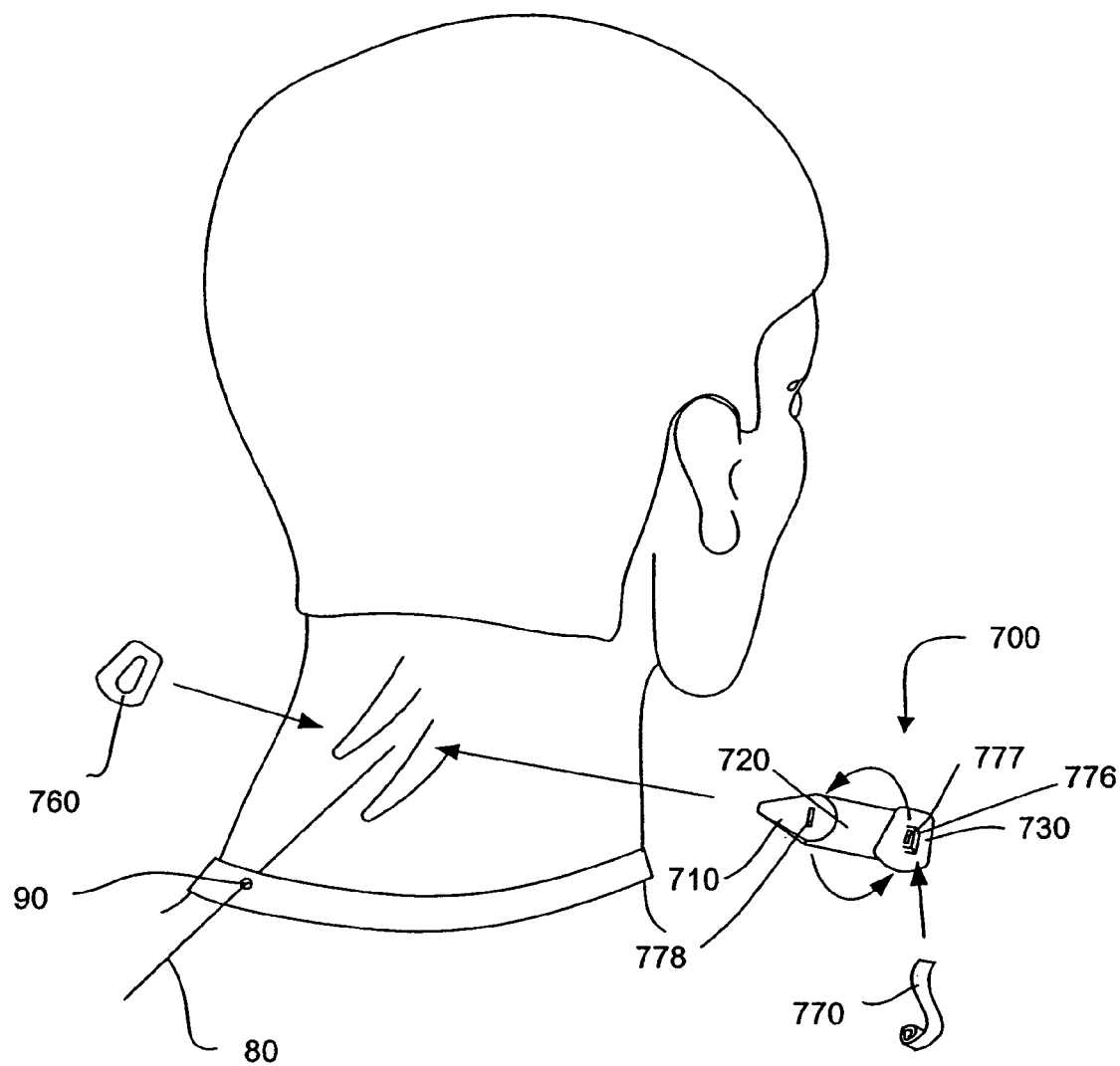
FIG. 30 illustrates an alternative embodiment of a method for implanting an interspinous implant including a binder in accordance with the present invention.

In other embodiments of methods in accordance with the present invention, the implant can include a binder, such as described above in FIGS. 18-19B. In such embodiments, as shown in FIG. 30, preferably a guide wire 80 is inserted through a placement network or guide 90 into the neck of the implant recipient (as shown and described above). Once the guide wire 80 is positioned with the aid of imaging techniques, an incision is made on the side of the neck so that an implant 700 in accordance with an embodiment of the present invention can be positioned in the neck thorough an incision and along a line that is about perpendicular to the guide wire 80 and directed at the end of the guide wire. The implant 700 can include a distraction guide 710, a spacer 720, and a first wing 730. The implant 700 is inserted into the neck of the patient, between adjacent spinous processes. Preferably during insertion, the distraction guide 710 pierces or separates the tissue without severing the tissue, and the implant 700 is positioned so that the spacer 720 is between the adjacent spinous processes.

Once the implant 700 is satisfactorily positioned and distracted, a second wing 760 can optionally be inserted along a line that is generally colinear with the line over which the implant 700 is inserted but from the opposite side of the neck. The anatomy of the neck is such that it is most convenient and minimally invasive to enter the neck from the side with respect to the implant 700 and the second wing 760. The second wing 760 can be mated to the implant 700 through an interference fit, or alternatively by attaching to one of the distraction guide 710 and the spacer 720 by the use of a fastener, or by some other device, as described above. For example, where a screw is employed, the screw can be positioned using a screw driving mechanism that is directed along a posterior to anterior line somewhat parallel to the guide wire. This posterior to anterior line aids the physician in viewing and securing the second wing 760 to the implant 700.

The implant 700 further includes an anchor 776 extending from the first wing 730. The anchor 776 includes or defines a slot 777. One or both of the distraction guide 710 and the spacer 720 includes a slot 778 as well. With the implant 700 properly positioned, and the second wing 760 secured, a binder 770 can be threaded through the anchor slot 777 and the slot 778. The binder 770 is threaded through the interspinous ligaments connected with surfaces of the adjacent spinous processes not contacting the implant 700 (i.e., the upper surface of the upper spinous process and the lower surface of the lower spinous process). A distal end of the binder 770 can be associated with a surgical needle which facilitates threading the binder 770, but which can be removed once the binder is properly arranged about the spinous processes. The distal end of the binder 770 can then be knotted, sutured, or otherwise fixed with a proximal end of the binder 770 so that the binder 770 is placed under tension. Alternatively, as described above, where the anchor 776 comprises a capture device, such as a rotatable cam, the binder 770 can be fixed to the capture device or first wing 730. The binder 770 limits flexion movement and can assists in maintaining the position of the implant 700 between the spinous processes.

Figure 31:
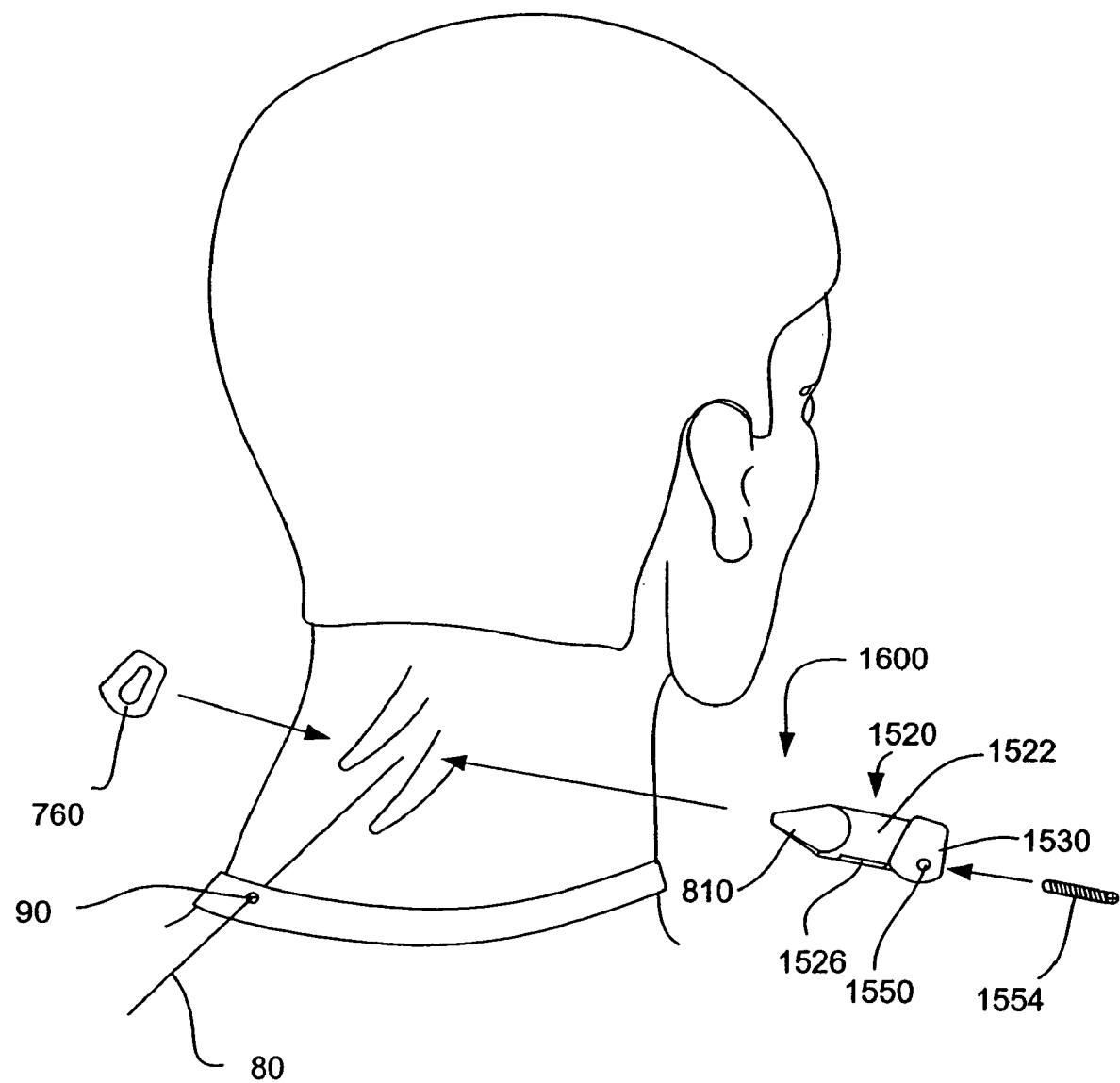
FIG. 31 illustrates an still another embodiment of a method for implanting an expandable interspinous implant in accordance with the present invention.

In still other embodiments of methods in accordance with the present invention, the implant can be an expandable implant 1500, such as described above in FIGS. 20-28. In such embodiments, as shown in FIG. 31, preferably a guide wire 80 is inserted through a placement network 90 into the neck of the implant recipient (as shown and described above). Once the guide wire 80 is positioned with the aid of imaging techniques, an incision is made on the side of the neck so that an expandable implant 1500 in accordance with an embodiment of the present invention, can be positioned in the neck thorough an incision and along a line that is about perpendicular to the guide wire 80 and directed at the end of the guide wire. The expandable implant 1500 can include a distraction guide 1510, a spacer 1520, and a first wing 1530. The implant 1500 is inserted into the neck of the patient, between adjacent spinous processes. Preferably during insertion, the distraction guide 1510 pierces or separates the tissue without severing the tissue, and the implant 1500 is positioned so that the spacer 1520 is between the adjacent spinous processes. An insert 1554 is then positioned within the incision and urged into a groove 1550 positioned between an expansion portion 1526 of the spacer 1520 and a main portion 1522 of the spacer 1520. The insert 1554 as shown in a threaded screw. As the insert 1554 engages threads of the groove 1550 and becomes seated within the groove 1550, the expansion portion 1526 is distracted away from the main portion 1522, thereby expanding the implant 1500.

Once the expandable implant 1500 is satisfactorily positioned and expanded, a second wing 1560 can optionally be inserted along a line that is generally colinear with the line over which the implant 1500 is inserted but from the opposite side of the neck. It is to be understood that the second wing 1560 can be implanted alternatively prior to the expansion step. The anatomy of the neck is such that it is most convenient and minimally invasive to enter the neck from the side with respect to the implant 1500 and the second wing 1560. The second wing 1560 can be mated to the implant 1500 through an interference fit, or alternatively by attaching to one of the distraction guide 1510 and the spacer 1520 by the use of a fastener, or by some other device, as described above. For example, where a screw is employed, the screw can be positioned using a screw driving mechanism that is directed along a posterior to anterior line somewhat parallel to the guide wire. This posterior to anterior line aids the physician in viewing and securing the second wing 1560 to the implant 1500. While the method has been described as including associating the second wing 1560 with the implant 1500 after the implant 1500 has been expanded, in other embodiments the second wing 1560 can be connected with the implant 1500 prior to expansion.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. An interspinous implant adapted to be inserted between spinous processes, the implant comprising:
    an interspinous spacer, including:
        a main portion having a recess;
        an expansion portion movable relative to the main portion between a retracted configuration relatively closer to the main portion and a deployed configuration relatively farther from the main portion, wherein the expansion portion is disposed at least partially in the recess in the retracted configuration;
        an insert-receiving cavity disposed between the expansion portion and the main portion;
    an insert selectively matable with the spacer;
    wherein, with the insert disposed in the insert-receiving cavity, the insert urges the expansion portion away from the main portion to the deployed configuration;
    wherein a larger amount of the expansion portion is disposed within the recess in the retracted configuration than in the deployed configuration.

2. The implant of claim 1 wherein the insert is distinct from the main portion and the expansion portion.

3. The implant of claim 2, wherein when the implant is inserted between spinous processes the insert-receiving cavity is accessible from a generally posterior direction.

4. The implant of claim 1, wherein the expansion portion comprises a compressible material.

5. The implant of claim 1, wherein the expansion portion comprises at least one of a biocompatible polymer and a surgical grade metal.

6. The implant of claim 1, further comprising a wing, slidably receivable over a portion of the spacer.

7. The implant of claim 1, wherein the main portion and the expansion portion are cojoined by a hinge.

8. An interspinous implant adapted to be inserted between spinous processes, the implant comprising:
    a distraction guide;
    an interspinous spacer, including:
        a main portion connected with the distraction guide; the main portion having a recess;
        an expansion portion associated with the main portion and moveable relative thereto between a retracted configuration and a deployed configuration; the expansion portion capable of being urged away from the main portion;
    a first wing connected with the main portion and disposed transverse to the main portion;
    wherein the main portion has a longitudinal axis and wherein the first wing and the distraction guide are disposed on opposing longitudinal sides of the main portion;
    wherein the expansion portion has lateral end surfaces extending transverse to the longitudinal axis of the main portion; the lateral end surfaces being longitudinally end-most portions of the expansion portion;
    wherein the lateral end surfaces are longitudinally bounded by the recess when the expansion portion is in the retracted configuration.

9. The implant of claim 8, further comprising:
    at least one groove disposed within the spacer, so that when an insert is positioned within the at least one groove, the at least one groove is expanded, thereby distracting the expansion portion away from the main portion.

10. The implant of claim 9, wherein when the implant is inserted between spinous processes the at least one groove is accessible from a generally posterior direction.

11. The implant of claim 8, wherein the expansion portion comprises a compressible material.

12. The implant of claim 8, wherein the expansion portion comprises one or both of a biocompatible polymer and a surgical grade metal.

13. The implant of claim 8, further comprising a second wing, slidably receivable over a portion of the spacer.

14. The implant of claim 8, wherein the main portion and the expansion portion are cojoined by a hinge.

15. The implant of claim 8:
wherein an external surface of the main portion facing away from the expansion portion is spaced from an external surface of the expansion portion facing away from the main portion by a first distance in a retracted configuration and a larger second distance in a deployed configuration.

16. An interspinous implant adapted to be inserted between spinous processes, the implant comprising:
an interspinous spacer, including:
a main portion having a recess;
an expansion portion movable relative to the main portion between a retracted configuration relatively closer to the main portion and a deployed configuration relatively farther from the main portion, wherein a portion of the expansion portion is disposed at least partially in the recess in the retracted configuration; the expansion portion having a bearing face facing away from the main portion;
an insert-receiving cavity disposed between the expansion portion and the main portion;
a longitudinal axis extending through a center of the spacer;
an insert selectively matable with the spacer;
wherein, with the insert disposed in the insert-receiving cavity, the insert urges the expansion portion away from the main portion to the deployed configuration;
wherein the bearing face of the expansion portion is disposed closer to the longitudinal axis in the retracted configuration than in the deployed configuration.

* * * * *